(12) United States Patent
Agnew et al.

(10) Patent No.: US 9,645,140 B2
(45) Date of Patent: May 9, 2017

(54) LABELING AND DETECTION OF POST TRANSLATIONALLY MODIFIED PROTEINS

(71) Applicant: LIFE TECHNOLOGIES CORPORATION, Carlsbad, CA (US)

(72) Inventors: Brian Agnew, Eugene, OR (US); Kyle Gee, Springfield, OR (US); Tamara Nyberg, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 83 days.

(21) Appl. No.: 14/330,727

(22) Filed: Jul. 14, 2014

(65) Prior Publication Data
US 2015/0051096 A1 Feb. 19, 2015

Related U.S. Application Data

(63) Continuation of application No. 11/674,140, filed on Feb. 12, 2007, now abandoned.
(Continued)

(51) Int. Cl.
*G01N 33/533* (2006.01)
*G01N 33/532* (2006.01)
(Continued)

(52) U.S. Cl.
CPC ..... *G01N 33/533* (2013.01); *A61K 47/48092* (2013.01); *C07K 16/00* (2013.01); *C12P 21/005* (2013.01); *G01N 33/5005* (2013.01); *G01N 33/531* (2013.01); *G01N 33/532* (2013.01); *G01N 33/581* (2013.01); *G01N 33/582* (2013.01); *G01N 33/583* (2013.01); *C07K 2317/41* (2013.01); *G01N 33/5008* (2013.01); *G01N 33/534* (2013.01); *Y10T 436/17* (2015.01)

(58) Field of Classification Search
CPC ............ A61K 47/48092; C12P 21/005; G01N 33/531; G01N 33/532; G01N 33/5005; G01N 33/533; G01N 33/583; G01N 33/581; G01N 33/582; G01N 33/534; G01N 33/5008; C07K 16/00; C07K 2317/41; Y10T 436/17
See application file for complete search history.

(56) References Cited

U.S. PATENT DOCUMENTS 4,196,265 A 4/1980 Koprowski et al.
4,384,042 A 5/1983 Miike et al.
(Continued)

FOREIGN PATENT DOCUMENTS

EP 171496 2/1986
EP 184187 6/1986
(Continued)

OTHER PUBLICATIONS 07756886.3, , "Extended EP Search Report mailed Nov. 28, 2012", Nov. 28, 2012, 1-6.
(Continued)

*Primary Examiner* — Shafiqul Haq

(57) ABSTRACT

Provided in certain embodiments are new methods for forming azido modified biomolecule conjugates of reporter molecules, carrier molecules or solid support. In other embodiments are provided methods for enzymatically labeling a biomolecules with an azide group.

8 Claims, 28 Drawing Sheets

COPPER CATALYZED AZIDE-ALKYNE [3+2] CYCLOADDITION

Related U.S. Application Data

(60) Provisional application No. 60/772,221, filed on Feb. 10, 2006, provisional application No. 60/804,640, filed on Jun. 13, 2006.

(51) Int. Cl.

| | | |
|---|---|---|
| *G01N 33/58* | (2006.01) | |
| *C12P 21/00* | (2006.01) | |
| *A61K 47/48* | (2006.01) | |
| *G01N 33/531* | (2006.01) | |
| *G01N 33/50* | (2006.01) | |
| *C07K 16/00* | (2006.01) | |
| *G01N 33/534* | (2006.01) | |

(56) References Cited

U.S. PATENT DOCUMENTS

| | | |
|---|---|---|
| 4,520,110 A | 5/1985 | Stryer et al. |
| 4,542,104 A | 9/1985 | Stryer et al. |
| 4,603,209 A | 7/1986 | Tsien et al. |
| 4,711,955 A | 12/1987 | Ward et al. |
| 4,714,763 A | 12/1987 | Theodoropulos |
| 4,774,339 A | 9/1988 | Haugland et al. |
| 4,810,636 A | 3/1989 | Corey et al. |
| 4,812,409 A | 3/1989 | Babb et al. |
| 4,816,567 A | 3/1989 | Cabilly et al. |
| 4,849,362 A | 7/1989 | Demarinis et al. |
| 4,859,582 A | 8/1989 | Stryer et al. |
| 4,945,171 A | 7/1990 | Haugland et al. |
| 4,981,977 A | 1/1991 | Southwick et al. |
| 5,047,519 A | 9/1991 | Hobbs et al. |
| 5,055,556 A | 10/1991 | Stryer et al. |
| 5,132,432 A | 7/1992 | Haugland et al. |
| 5,187,288 A | 2/1993 | Kang et al. |
| 5,196,306 A | 3/1993 | Bobrow et al. |
| 5,208,148 A | 5/1993 | Haugland et al. |
| 5,225,539 A | 7/1993 | Winter |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,133 A | 12/1993 | Narula |
| 5,279,954 A | 1/1994 | Wagner et al. |
| 5,316,906 A | 5/1994 | Haugland et al. |
| 5,362,628 A | 11/1994 | Haugland et al. |
| 5,442,045 A | 8/1995 | Haugland et al. |
| 5,443,986 A | 8/1995 | Haughland et al. |
| 5,451,343 A | 9/1995 | Neckers et al. |
| 5,459,276 A | 10/1995 | Kuhn et al. |
| 5,478,741 A | 12/1995 | Maret et al. |
| 5,486,616 A | 1/1996 | Waggoner et al. |
| 5,501,980 A | 3/1996 | Katerinopoulos et al. |
| 5,545,806 A | 8/1996 | Lonberg et al. |
| 5,569,587 A | 10/1996 | Waggoner |
| 5,569,766 A | 10/1996 | Waggoner et al. |
| 5,569,825 A | 10/1996 | Lonberg et al. |
| 5,576,424 A | 11/1996 | Mao et al. |
| 5,583,001 A | 12/1996 | Bobrow et al. |
| 5,625,126 A | 4/1997 | Lonberg et al. |
| 5,627,027 A | 5/1997 | Waggoner |
| 5,633,425 A | 5/1997 | Lonberg et al. |
| 5,639,947 A | 6/1997 | Hiatt et al. |
| 5,648,465 A | 7/1997 | Margolis et al. |
| 5,661,016 A | 8/1997 | Lonberg et al. |
| 5,696,157 A | 12/1997 | Wang et al. |
| 5,731,158 A | 3/1998 | Bobrow et al. |
| 5,773,236 A | 6/1998 | Diwu et al. |
| 5,798,276 A | 8/1998 | Haugland et al. |
| 5,808,044 A | 9/1998 | Brush et al. |
| 5,830,912 A | 11/1998 | Gee et al. |
| 5,846,737 A | 12/1998 | Kang |
| 5,858,731 A | 1/1999 | Sorge et al. |
| 5,877,310 A | 3/1999 | Reddington et al. |
| 5,948,386 A | 9/1999 | Katti et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,162,931 A | 12/2000 | Gee et al. |
| 6,255,475 B1 | 7/2001 | Kwiatkowski |
| 6,339,392 B1 | 1/2002 | Ashihara et al. |
| 6,562,632 B1 | 5/2003 | Szalecki et al. |
| 6,570,040 B2 | 5/2003 | Saxon et al. |
| 6,664,047 B1 | 12/2003 | Haugland et al. |
| 6,716,979 B2 | 4/2004 | Diwu et al. |
| 6,737,236 B1 | 5/2004 | Pieken et al. |
| 6,861,254 B1 | 3/2005 | Rosenberg et al. |
| 6,936,701 B2 | 8/2005 | Bertozzi |
| 6,974,873 B2 | 12/2005 | Leung et al. |
| 6,977,305 B2 | 12/2005 | Leung et al. |
| 7,052,843 B2 | 5/2006 | Li et al. |
| 7,070,941 B2 | 7/2006 | Zhao et al. |
| 7,122,703 B2 | 10/2006 | Saxon et al. |
| 7,265,085 B2 | 9/2007 | DeFrees et al. |
| 7,282,567 B2 | 10/2007 | Goldenberg et al. |
| 7,332,355 B2 | 2/2008 | Hsieh-Wilson et al. |
| 7,375,234 B2 | 5/2008 | Sharpless et al. |
| 7,427,678 B2 | 9/2008 | Pieken et al. |
| 7,763,736 B2 | 7/2010 | Sharpless |
| 8,114,636 B2 | 2/2012 | Agnew et al. |
| 8,716,033 B2 | 5/2014 | Agnew et al. |
| 8,785,212 B2 | 7/2014 | Agnew et al. |
| 2002/0012989 A1 | 1/2002 | Ledbetter et al. |
| 2003/0049721 A1 | 3/2003 | Bertozzi et al. |
| 2003/0073149 A1 | 4/2003 | Archer et al. |
| 2003/0211579 A1 | 11/2003 | Van Ness et al. |
| 2003/0219876 A1 | 11/2003 | Ledbetter et al. |
| 2004/0067497 A1 | 4/2004 | Li et al. |
| 2004/0142856 A1 | 7/2004 | DeFrees et al. |
| 2004/0235076 A1 | 11/2004 | Liu et al. |
| 2005/0032081 A1 | 2/2005 | Ju et al. |
| 2005/0106627 A1 | 5/2005 | Zhao et al. |
| 2005/0130235 A1 | 6/2005 | Hsieh-Wilson |
| 2005/0222427 A1 | 10/2005 | Sharpless et al. |
| 2006/0147963 A1 | 7/2006 | Barone et al. |
| 2006/0205041 A1 | 9/2006 | Frye et al. |
| 2006/0276658 A1 | 12/2006 | Saxon et al. |
| 2007/0249014 A1 | 10/2007 | Agnew et al. |
| 2008/0050731 A1 | 2/2008 | Agnew et al. |
| 2008/0108557 A1 | 5/2008 | Behrens et al. |
| 2009/0215635 A1 | 8/2009 | Carell et al. |
| 2009/0240030 A1 | 9/2009 | Ju et al. |
| 2011/0065907 A1* | 3/2011 | Salic ............... C12Q 1/68 536/23.1 |
| 2014/0206848 A1 | 7/2014 | Agnew et al. |
| 2014/0336079 A1 | 11/2014 | Agnew et al. |
| 2014/0377837 A1 | 12/2014 | Agnew et al. |
| 2015/0051096 A1 | 2/2015 | Agnew |

FOREIGN PATENT DOCUMENTS

| | | |
|---|---|---|
| EP | 125023 | 6/1991 |
| EP | 1065250 | 12/2004 |
| JP | 2005-314382 | 11/2005 |
| WO | WO-86/01533 | 3/1986 |
| WO | WO-96/09316 | 3/1996 |
| WO | WO-96/20289 | 7/1996 |
| WO | WO-96/34984 | 11/1996 |
| WO | WO-97/40104 | 10/1997 |
| WO | WO-98/30575 | 7/1998 |
| WO | WO99/51702 | 10/1999 |
| WO | WO-01/21624 | 3/2001 |
| WO | WO-01/68565 | 9/2001 |
| WO | WO-02/26891 | 4/2002 |
| WO | WO-02/29003 | 4/2002 |
| WO | WO-03/017311 | 2/2003 |
| WO | WO-03/101972 | 12/2003 |
| WO | WO-2004/018497 | 3/2004 |
| WO | WO-2004/033651 | 4/2004 |
| WO | WO-2004/063344 | 7/2004 |

(56) References Cited

FOREIGN PATENT DOCUMENTS

| | | |
|---|---|---|
| WO | WO-2005/042504 | 5/2005 |
| WO | WO-2005/050226 A1 | 6/2005 |
| WO | WO-2005/075993 A1 | 8/2005 |
| WO | WO-2006/038184 | 4/2006 |
| WO | WO-2006/0117161 | 11/2006 |
| WO | WO-2007/050811 | 5/2007 |
| WO | WO-2007095506 A1 | 8/2007 |
| WO | WO-2007095506 C1 | 8/2007 |
| WO | WO-2008/029281 A3 | 3/2008 |
| WO | WO-2008029281 A2 | 3/2008 |

OTHER PUBLICATIONS 07825657.5, , "Extended European Search Report Recd mailed Aug. 23, 2010".

13162088.2, , "European Search Report", 2013, pp. 1-12.

13162096.5, , "European Search Report", 2013, pp. 1-13.

Agard, N et al., "A Strain-Promoted [3 + 2]Azide-Alkyne Cycloaddition for Covalent Modification of Biomolecules in Living Systems", *J. Am. Chem Soc*, vol. 126(46), 2004, pp. 15046-15047.

Antos, J. M. et al., "Transition metal catalyzed methods for site-selective protein modification", *Current Opinion in Chemical Biology*, vol. 10(3), Jun. 1, 2006, 253-262.

Anumula, et al., "Advances in fluorescence derivatization methods for high-performance liquid chromatographic analysis of glycoprotein carbohydrates", *Analytical Biochemistry, Academic Press*, vol. 350, 2006, pp. 1-23.

Beidler, et al., "Cloning and High Level Expression of a Chimeric Antibody with Specificity for Human Carcinoembryonic Antigen", *J. Immunol.*, 141, 1988, 4053-4060.

Berliner, Lawrence J. et al., "Structure-Function Relationships in Lactose Synthase. Structural Requirements of the Uridine 5'-Diphosphate Galactose Binding Site", *Biochemistry*, vol. 21, No. 25, 1982, 6340-6343.

Bertozzi, et al., "A Strain-Promoted [3+2] Azide-Alkyne Cycloaddition for Covalent Modification of Biomolecules in Living Systems.", *J. Am. Chem. Soc.*, 126, 2004, 15046-15047.

Better, M. et al., "*Escherichia coli* secretion of an active chimeric antibody fragment", *Science*, vol. 240, 1988, 1041-1043.

Bouizar, et al., "Purification and Characterization of Calcitonin Receptors in Rat Kidney Membranes by Covalent Cross-Linking Techniques.", *European Journal of Biochemistry*, vol. 155, No. 1, 1986, 141-147.

Breinbauer, et al., "Azide-Alkyne coupling : A powerful reaction for bioconjugate chemistry", *ChemBioChem*, vol. 4, 2003,1147-1149.

Browning, et al., "Studies on the Differing Effects of the Tumor Necrosis Factor and Lymphotoxin on the Growth of Several Human Tumor Lines", *Journal of Immunology*, vol. 143, No. 6, 1989, 1859-1867.

Camarero, J A. , "New developments for the site-specific attachment of protein to surfaces", *Biophysical Reviews and Letters*, 2005, 1-28.

Capila, Ishan et al., "Heparin-Protein Interactions", *Angewandte Chemie International Edition in English*, vol. 41, 2002, 390-412.

Chan, T. et al., "Polytriazoles as Copper(I)-Stabilizing Ligands in Catalysis", *Organic Letters*, vol. 6, No. 17, 2004, pp. 2853-2855.

Comer, Frank I. et al., "Characterization of a Mouse Monoclonal Antibody Specific for O-Linked N-Acetylglucosamine", *Analytical Biochemistry*, vol. 293, 2001, 169-177.

Do, Ki-Young et al., "a-Lactalbumin Induces Bovine Milk B1,4-Galactosyltransferase to Utilize UDP-GalNAc*", *J. Biol. Chem.*, vol. 270, No. 31, 1995, 18447-18451.

Dube, Danielle H. et al., "Metabolic Oligosaccharide Engineering as a Tool for Glycobiology.", *Current Opinion in Chemical Biology*, vol. 7, 2003, 616-625.

EP 13162103.9, , "Extended European Search Report", 2013, pp. 1-9.

Gastinel, Louis N. et al., "Crystal structures of the bovine B4galactosyltransferase catalytic domain and its complex with uridine diphosphogalactose", *The EMBO Journal*, vol. 18, No. 13, 1999, 3546-3557.

Gorevic, Peter D. et al., "Immunoglobulin G (IgG)", *Methods in Enzymology*, vol. 116, 1985, 3-25.

Green, K. D. et al., "Kinase-Catalyzed Biotinylation for Phosphoprotein Detection", *Department of Chemistry, Wayne State University*, 2007, pp. 10-11.

Gupta, S. S. et al., "Virus-glycopolymer conjugates by copper(I) catalysis of atom transfer radical polymerization and azide-alkyne cycloaddition", *Chemical Communications*,34, Jan. 1, 2005, 4315-4317.

Gupta, Sayam S. et al., "Accelerated Bioorthogonal Conjugation: A Practical Method for the Ligation of Diverse Functional Molecules to a Polyvalent Virus Scaffold", *Bioconjugate Chemistry*, vol. 16, No. 6, 2005, 1572-1579.

Hang, H. C. et al., "A metabolic labeling approach toward proteomic analysis of mucin-type O-linked glycosylation", *Proceedings of the National Academy*,100(25), Dec. 9, 2003, 14846-14851.

Hang, H. C. et al., "Ketone Isosteres of 2-N-Acetamidosugars as Substrates for Metabolic Cell Surface Engineering", *J. Am. Chem. Soc.*, vol. 123, 2001, 1242-1243.

Hang, Howard et al., "Chemical Probes for the Rapid Detection of Fatty-Acylated Proteins in Mammalian Cells", *J. Am. Chem. Soc.* 129 (10), 2007, 2744-2745.

Hang, Howard et al., "The chemistry and biology of mucin-type 0-linked glycosylation", *Bioorganic & Medicinal Chemistry*,13(7), XP005045012, Sep. 1, 2005, 5021-5034.

Hang, Howard C. et al., "Probing Glycosyltransferase Activities with the Staudinger Ligation", *Journal of the American Chemical Society*, vol. 126, No. 1, 2004, 6-7.

Hassane, Fatouma S. et al., "Targeted Liposomes: Convenient coupling of ligands to preformed vesicles using click chemistry", *Bioconjugate Chemistry*,17(3), May 6-Jun. 6, 849-854.

Haugland, , "The Handbook; A Guide to Fluorescent Probes and Labeling Technologies", *Tenth Edition, CD-ROM*, Invitrogen / Molecular Probes Invitrogen Detection Technologies, 2005, 1-1126.

Haugland, R. , "The Molecular Probes Handbook: A Guide to Fluorescent Probes and Labeling Technologies", *Eleventh Edition*, Molecular Probes, Inc. (CD-ROM: ISBN 978-0-9829279-0-8), Jun. 3, 2011, 2010.

Haugland, Richard P. , "Molecular Probes Handbook of Fluorescent Probes and Research Products", *Ninth Edition, CD ROM, Table of Contents*, Molecular Probes, Inc., 2002, 1-6.

Helenius, Ari et al., "Intracellular Functions of N-Linked Glycans", *Science*, vol. 291, 2001, 2364-2369.

Henderson, R. A. , "Human Tumor Antigens are Ready to Fly", *Advances in Immunology*, 62, 1996, 217-256.

Jespers, L. et al., "Guiding the selection of human antibodies from phage display repertoires to a single epitode of an antigen", *Nature Biotechnology*, vol. 12, No. 9, 1994, 899-903.

Jones, Peter T. et al., "Replacing the complementarity-determining regions in a human antibody with those from a mouse", vol. 321, *Nature*, 1986, 522-525.

Joshi, et al., "ATP Synthase Complex from Bovine Heart Mitochondria", *Journal of Biological Chemistry*, vol. 265, No. 24, 1990, 14518-14525.

Jung, et al., "Crosslinking of platelet glycoprotein Ib by N-succinimidyl(4- azidophenyldithio)propionate and 3,3'-dithiobis-(sulfosuccinimidyl propionate)", *Biochimica et Biophysica Acta*, vol. 761, No. 2, 1983, 152-162.

Khidekel, Nelly et al., "A Chemoenzymatic Approach Toward the Rapid and Sensitive Detection of O-GlcNAc Posttranslational Modifications", *Journal of the American Chemical Society*, vol. 125, 2003, 16162-16163, S2-S14.

Kiick, K. L. et al., "Incorporation of azides into recombinant proteins for chemoselective modification by the Staudinger ligation.", *Proceedings of the National academy of Sciences* , vol. 99 (1), 2002, 19-24.

(56) References Cited

OTHER PUBLICATIONS

Kolb, H. C. et al., "Click Chemistry: Diverse Chemical Function from a Few Good Reactions", *Angewandte Chemie International Edition in English*, 40, 2001, 2004-2021.

Kwon, S. et al., "Selective Enrichment of Thiophosphorylated Polypeptides as a Tool for the Analysis of Protein Phosphorylation", *Molecular & Cellular Proteomics*, vol. 2 (4), May 6, 2003, 242-247.

Langenhan, J. M. et al., "Recent Carbohydrate-based chemoeslective ligation applications", *Current organics systhesis*, 2(1), Jan. 2005, 59-81.

Lasky, Laurence A. et al., "Selectin-Carbohydrate Interactions and the Initiation of the Inflammatory Response", *Annual Review Biochemistry*, vol. 64, 1995, 113-139.

Laughlin, S. et al., "Metabolic Labeling of Glycans with Azido Sugars for Visualization and Glycoproteomics", *Methods in Enzymology, Academic Press, US*, vol. 415, 2006, pp. 230-250.

Lazarevic, et al., "Syntheses of unnatural N-substituted UDP-galactosamines as alternative substrates for N-acetylgalactosarninyl transfereses", *Carbohydrate Research* vol. 337, 2002, 2187-2194.

Lee, S. et al., "Synthesis and reactivity of novel y-phosphate modified ATP analogues", *Bioorganic & Medicinal Chemistry Letters*, vol. 19, Apr. 14, 2009, 3804-3807.

Lee., B. et al., "Interaction of Psoralen-Derivatized Oligodeoxyribonucleoside Methylphosphonates with single-Stranded DNA", *Biochemistry*, 27, 1988, 3197-3203.

Lewis, W. G. et al., "Click chemistry in Situ: Acetylcholinesterase as a Reaction Vessel for the Selectivity Assembly of a Femtomolar Inhibitor from an Array of building Blocks", *Angewandte Chemie International Edition in English*, 41(6), 2002, 1053-1057.

Lewis, Warren G. et al., "Discovery and Characterization of Catalysts for Azide-Alkyne Cycloaddition by Fluorescence Quenching", *Journal of the American Chemical Society*, vol. 126, No. 30, 2004, 9152-9153.

Liu, et al., "Production of a mouse-human chimeric monoclonal antibody to CD20 with potent Fc-dependent biologic activity", *J. Immunol.*, 139, 1987, 3521-3526.

Liu, Alvin Y. et al., "Chimeric mouse-human IgG1 antibody that can mediate lysis of cancer cells", *Proceedings of the National Academy of Sciences (PNAS)*, vol. 84, No. 10, May 15, 1987, 3439-3433.

Lonberg, N. et al., "Human antibodies from transgenic mice.", *Int. Rev. Immunol.*, vol. 13(1), 1995, 65-93.

Losey, et al., "Incorporation of glucose analogs by GtfE and GtfD from the vancomycin biosynthesis pathway to generate varient glycopeptides", *Chemistry & Biology* vol. 9, 2002, 1305-1314.

Luchansky, et al., "Metabolic functionalization of recombinant glycoproteins", *Biochemistry* 2004; vol. 43, 2004, 12358-12366.

Luchansky, S. et al., "Constructing Azide-Labeled Cell Surfaces Using Polysaccharide Biosynthetic Pathways", *Methods in Enzymology*, vol. 362, 2003, pp. 249-272.

Maciej, A. et al., "Identification of phosphopeptides by chemical modification with an isotopic tag and ion trap mass spectrometry", *Rapid Communications in Mass Spectrometry*, vol. 16, 2002, pp. 999-1001.

Martin, Maria J. et al., "Human Embryonic Stem Cells Express an Immunogenic Non-Human Sialic Acid.", *Nature Medicine*, vol. 11, Jan. 30, 2005, 228-232.

Mattila, K. et al., "Derivatization of phosphopeptides with mercapto- and amino-functionalized conjugate groups by phosphate elimination and subsequent Michael addition", *Org. Biomol. Chem.*, vol. 3, 2005, pp. 3039-3044.

Morrison, S. L. , "Transfectomas Provide Novel Chimeric Antibodies", *Science*, 229, 1985, 1202-1207.

Murakami, N. et al., "Studies on Cardiac lngrediets of Plants. VII: Chemical Transformation of Proscillaridin by Means of the Diels-Alder Reaction and Biological Activities of its Derivatives", *Chem. Pharm. Bull.* 39(8), 1991, 1962-1966.

Nishimura, et al., "Recombinant Human-Mouse Chimeric Monoclonal Antibody Specific for Common Acute Lymphocytic Leukemia Antigen", *Canc. Res.*, 47, 1987, 999-1005.

Oi, et al., "Chimeric Antibodies", *BioTechniques*, 4, 1986, 214-221.

Park, et al., "Characterization of the Cell Surface Receptor for a Multi-Lineage Colony-Stimulating Factor (CSF-2alpha)", *Journal of Biological Chemistry*, vol. 261, No. 1, 1986, 205-210.

Pauling, Linus et al., "The Adjacent Charge Rule and the Structure of Methyl Azide, Methyl Nitrate, and Fluorine Nitrate", *J. Am. Chem. Soc.*, vol. 59, No. 1, 1937, 13-20.

PCT/IB07/003472, , "International Search Report mailed Dec. 2, 2009", 13.

PCT/IB07/03472, , "International Search report mailed on Jul. 29, 2009", 17 pgs.

PCT/US07/62006, , "International Preliminary Report on Patentability mailed Jul. 5, 2007", Jul. 5, 2007.

PCT/US07/62006, , "International Search Report mailed Jul. 5, 2007", Jul. 5, 2007.

PCT/U507/62006, , "Written Opinion mailed Jul. 5, 2007", Jul. 5, 2007.

Pei, Y. et al., "Post-Modification of Peptoid Side Chains: [3+2] Cycloaddition of Nitrole Oxides with Alkenes and Alkynes on the Solid-Phase", *Tetrahedron Letters*, vol. 35, No. 32, 1994, 5825-5828.

Pohl, et al., "Cellular Addresses: Step One in Creating a Glycocode", *Chemistry and Biology*, 11(7), Jul. 1, 2004, 891-892.

Qian, W. et al., "Highlights in Organic Chemistry Advances in 1,3-Dipolar Cycloaddition Reaction of Azides and Alkynes—A Prototype of Click Chemistry", *Letters in Organic Chemistry*, vol. 2, 2005, pp. 293-301.

Ramakrishnan, Boopathy et al., "Structure-based Design of B1,4-Galactosyltransferase I (B4Gal-T1) with Equally Efficient N-Acetylgalactosaminyltransferase Activity", *J. Biol. Chem.*, vol. 277, No. 23, 2002, 20833-20839.

Ramakrishnan, Boopathy et al., "α-Lactalbumin (LA) Stimulates Milk β-1,4-Galactosyltransferase I (β4Gal-T1) to Transfer Glucose from UDP-glucose to N-Acetylglucosamine", *J. Biol. Chem.*, vol. 276, No. 40, 2001, 37665-37671.

Rodionov, V. et al., "Mechanism of the Ligand-Free Cu-Catalyzed Azide-Alkyne Cycloaddition Reaction", *Andew. Chem. Int. Ed.*, vol. 44, 2005, 2210-2215.

Roquemore, Elizabeth P. et al., "Detection of O-Linked N-Acetylglucosamine (O-GlcNAc) on Cytoplasmic and Nuclear Proteins", *Methods in Enzymology*, vol. 230, 1994, 443-460.

Rudd, Pauline M. et al., "Glycosylation and the Immune System", *Science*, vol. 291, Mar. 23, 2001, 2370-2376.

Saxon, et al., "Investigating Cellular Metabolism of Synthetic Azidosugars Using the Staudinger Ligation", *J. Am. Chem. Soc.*, 124(50), 2002, 14893-14902.

Saxon, Eliana et al., "Cell Surface Engineering by a Modified Staudinger Reaction.", *Science*, vol. 287, No. 5460, Mar. 17, 2000, 2007-2010.

Shaw, et al., "Mouse/Human Chimeric Antibodies to a Tumor-Associated Antigen: Biologic Activity of the Four Human IgG Subclasses", *J. natl. Cancer Inst.*, 80, 1988, 1553-1559.

Snow, Claudette M. et al., "Monoclonal Antibodies Identify a Group of Nuclear Pore Complex Glycoproteins", *The Journal of Cell Biology*, vol. 104, May 1987, 1143-1156.

Soellner, Matthew B. et al., "Site-Specific Protein Immobilization by Staudinger Ligation", *J. Amer. Chem. Soc.*, vol. 125, 2003, 11790-11791.

Speers, A. , "Profiling Enzyme Activities In Vivo Using Click Chemistry Methods", *Chemistry & Biology*, vol. 11, 2004, pp. 535-546.

Staudinger, et al., "Uber neue organische Phosphorverbindunge III. Phosphinmethylenderivate und Phosphinime", *Helv. Chim. Acta.*, 2, 1919, 635-646.

Sun, et al., "Chimeric antibody with human constant regions and mouse variable regions directed against carcinoma-associated antigen 17-1A", *Proceedings of the National Academy of Sciences (PNAS)*, 84, 1987, 214-218.

Sun, X. et al., "Carbohydrate and Protein Immobilization onto Solid Surfaces by Sequential Diels-Alder and Azide-Alkyne Cycloadditions", *American Chemical Society*, Bioconjugate Chem., vol. 17, 2006, pp. 52-57.

(56) References Cited

OTHER PUBLICATIONS

Takeuchi, Makoto et al., "Role of sugar chains in the in vitro biological activity of human erythropoietin produced in recombinant Chinese hamster ovary cells", *J. of Bio. chem*, vol. 265 (21), 1990, 12127-12130.

Tamura, Toshiaki et al., "Reducing-End Modification of N-Linked Oligosaccharides with Tyrosine", *Analytical Biochemistry*, vol. 216, No. 2, 1994, 335-344.

Vandest, P. et al., "Photoaffinity Labelling of Arginine Kinase and Creatine Kinase with a y-P-Substituted Arylazido Analogue of ATP", *Eur. J. Biochem.*, vol. 104, 1980, 433-442.

Varki, , "Biological roles of oligosaccharides: All of the theories are correct", *Glycobiology*, vol. 3, No. 2, 1993, 97-130.

Verhoeyen, et al., "Reshaping human antibodies: grafting an antilysozyme activity", *Science*, 239, 1988, 1534-1536.

Vocadlo, D. J. et al., "A Strategy for Functional Proteomic Analysis of Glycosidase Activity from Cell Lysates", *Angew. Chem. Int. Ed.*, vol. 43, 2004, pp. 5338-5342.

Wang, Charles et al., "Site-Specific Fluorescent Labeling of DNA Using Staudinger Ligation", *Bioconjugate Chem.*, 14, 2003, 697-701.

Wang, Q. et al., "Advances in 1,3-Dipolar Cycloaddition Reaction of Azides and Alkynes—A Prototype of "Click" Chemistry", *Letters in Organic Chemistry, Highlights in Organic Chemistry*, vol. 2, 2005, pp. 293-301.

Wang, Qian et al., "Bioconjugation by Copper(I)-Catalyzed Azide-Alkyne [3+2] Cycloaddition", *Journal of the American Chemical Society*, vol. 125, No. 11, 2003, 3192-3193.

Wang, Z. et al., "Microarray-Based Detection of Protein Binding and Functionality by Gold Nanoparticles Probes", *Anal. Chem*, vol. 77, Sep. 1, 2005, 5770-5774.

Weckwerth, W. et al., "Comparative quantification and identification of phosphoproteins using stable isotope labeling and liquid chromatography/mass spectrometry", *Rapid Communications in Mass Spectrometry*, vol. 14, 2000, pp. 1677-1681.

Wells, Lance et al., "Glycosylation of Nucleocyptoplasmic Proteins: Signal Transduction and O-GlcNAc", *Science*, vol. 291, Mar. 23, 2001, 2376-2378.

Wood, Clive R. et al., "The synthesis and in vivo assembly of functional antibodies in yeast.", *Nature*, vol. 314, Apr. 4, 1985, 446-449.

Wright and Morrison, Effect of glycosylation on antibody functions: implication for genetic engineering, TIBTECH, vol. 15, 1997, pp. 26-32.

Zachara, Natasha E. et al., "The Emerging Significance of O-GlcNAc in Cellular Regulation", *Chemical Reviews*, vol. 102, No. 2, 2002, 431-438.

Zarling, et al., "Mapping of Lymphocyte Surface Polypeptide Antigens by Chemical Cross-Linking with BSOCOES", *Journal of Immunology*, vol. 124, No. 2, 1980, 913-920.

Speers, A. E. et al., "Activity-Based Protein Profiing (ABPP) and Click Chemistry (CC)-ABPP by MudPIT Mass Spectrometry", *Current Protocols in Chemical Biology*, vol. 1, Dec. 1, 2009, 29-41.

Rodwell, J. et al., "Site-specific covalent modification of monoclonal antibodies: In vitro and in vivo evaluations", 1986, 2632-2636.

Vocadlo, et al., "A chemical approach for identifying O-GlcNAc-modified proteins in cells", *PNAS* 2003; vol. 100(16), 2003, 9116-9121.

\* cited by examiner

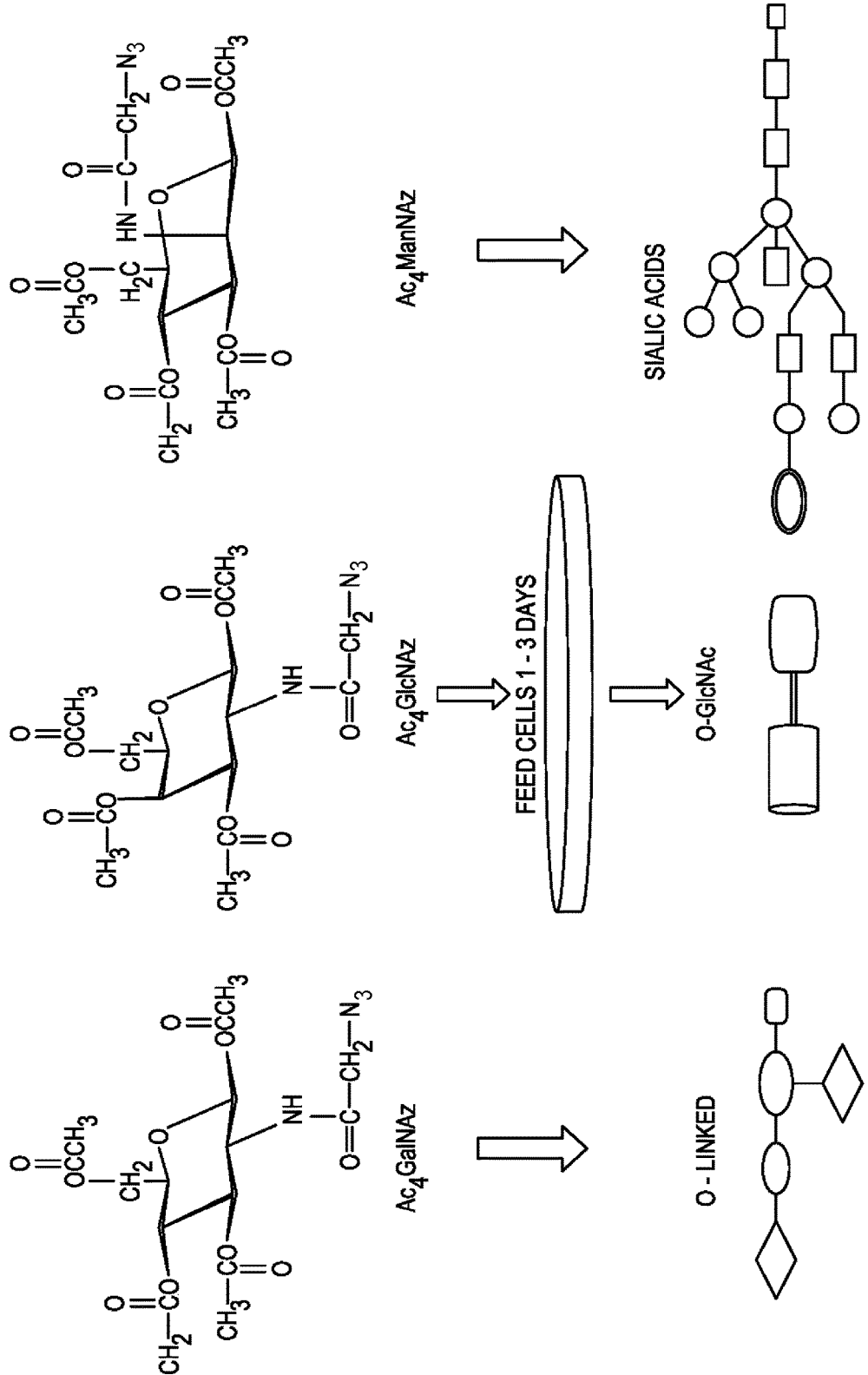

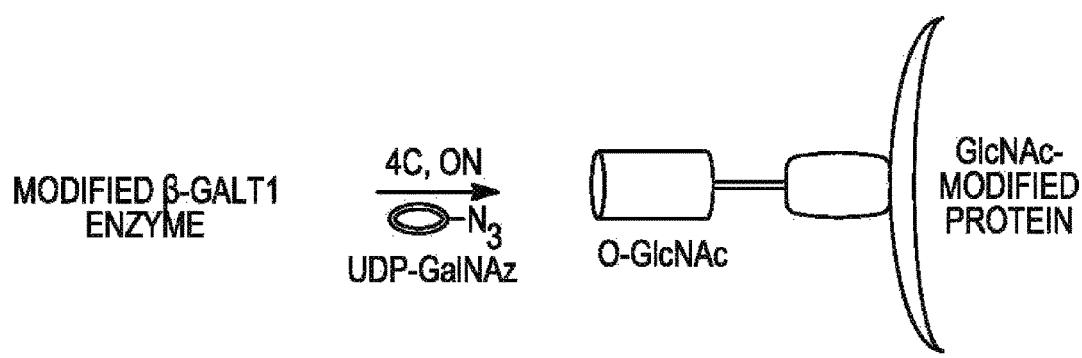
FIG. 6A1
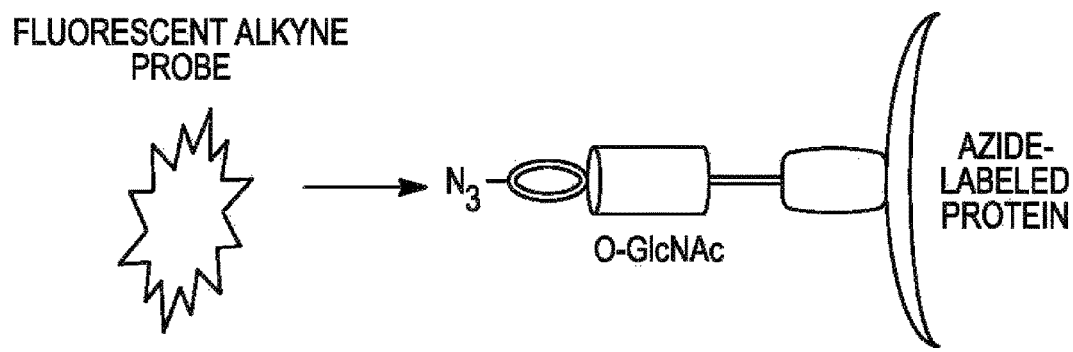
FIG. 6A2

FLUORESCENT ALKYNE
PROBE
pmol 40　10　2.5　0.6　0.16
　　40　20　5　1.3　0.3　0.08
FIG. 6B1
SYPRO RUBY STAIN
pmol 40　10　2.5　0.6　0.16
　　40　20　5　1.3　0.3　0.08
FIG. 6B2

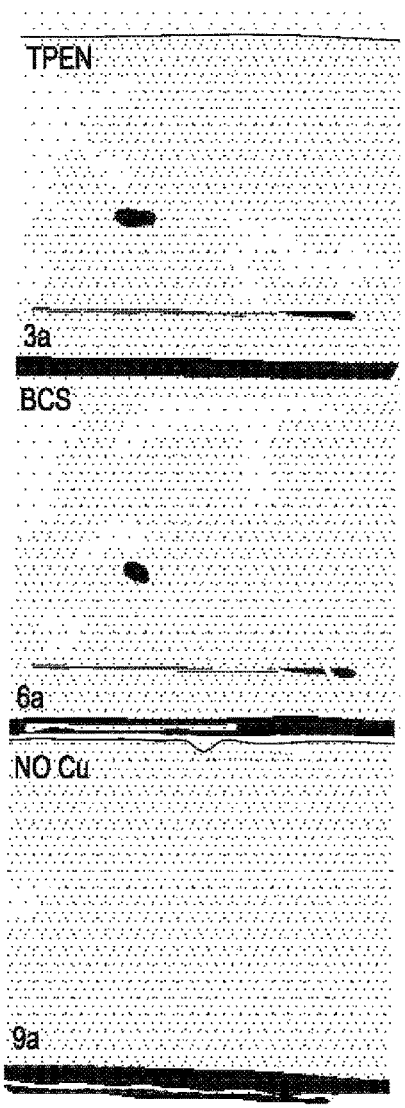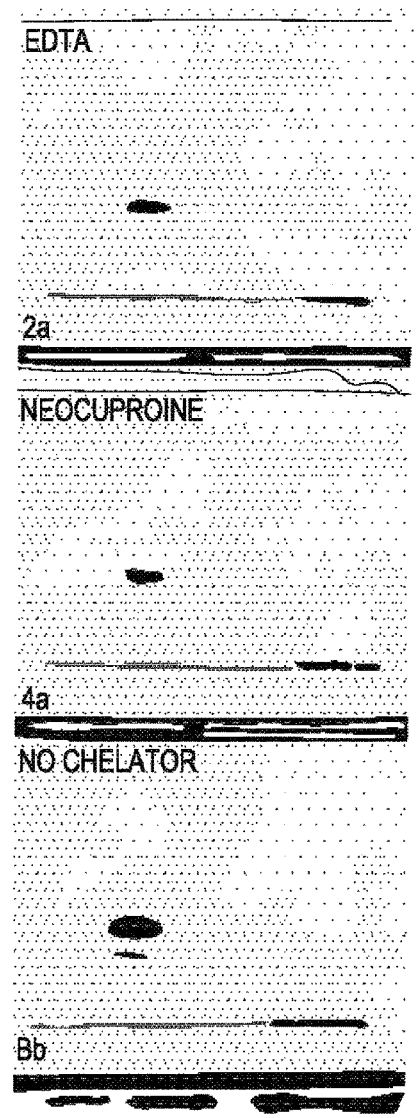
FIG. 14A1                    FIG. 14A2

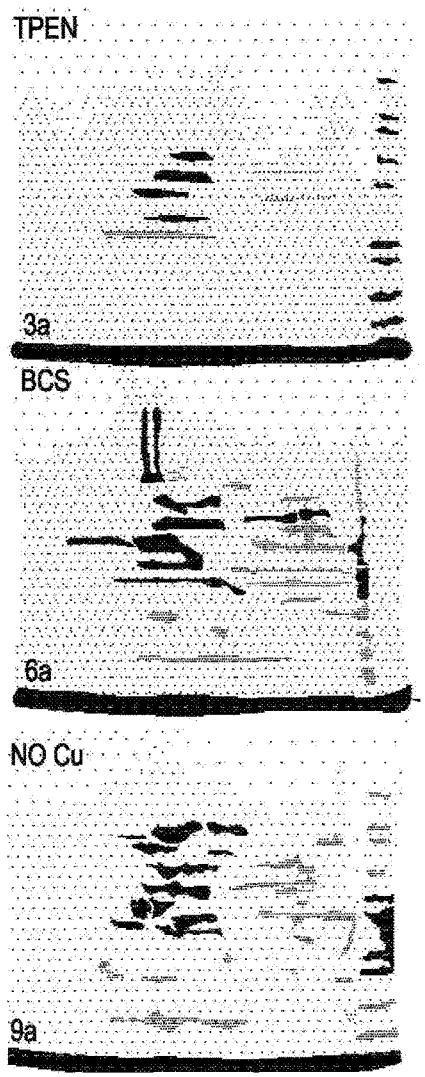
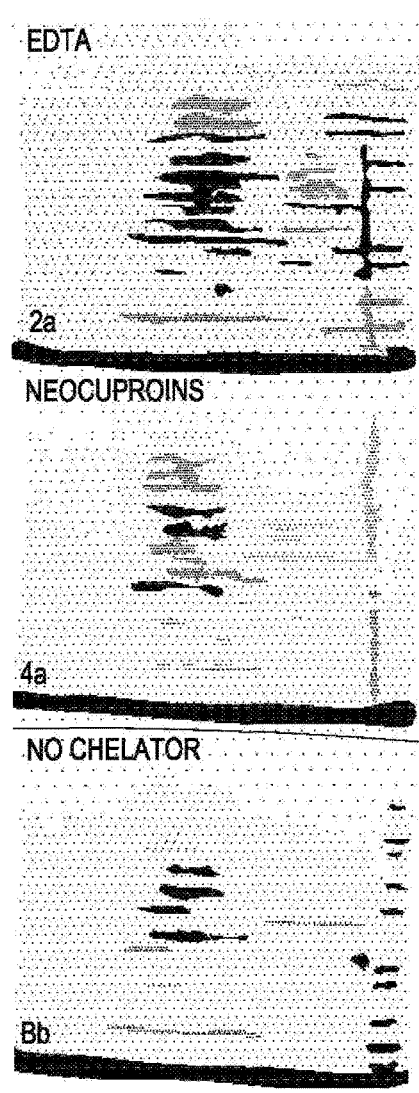
FIG. 14B1    FIG. 14B2

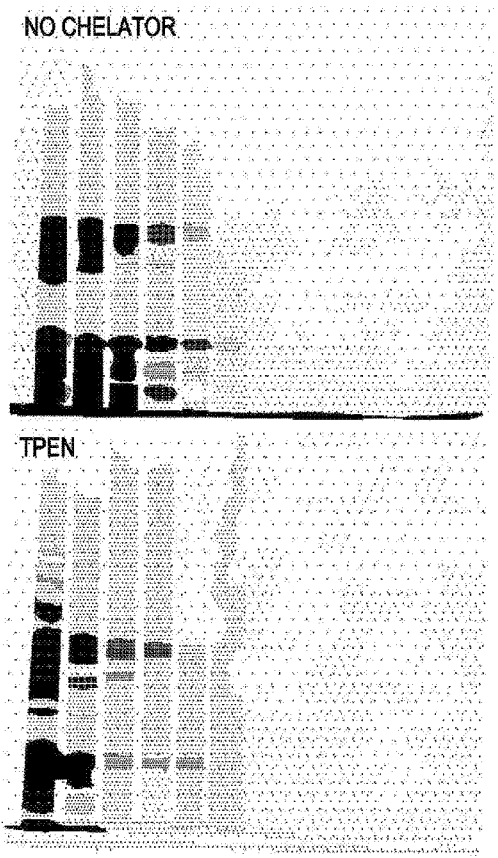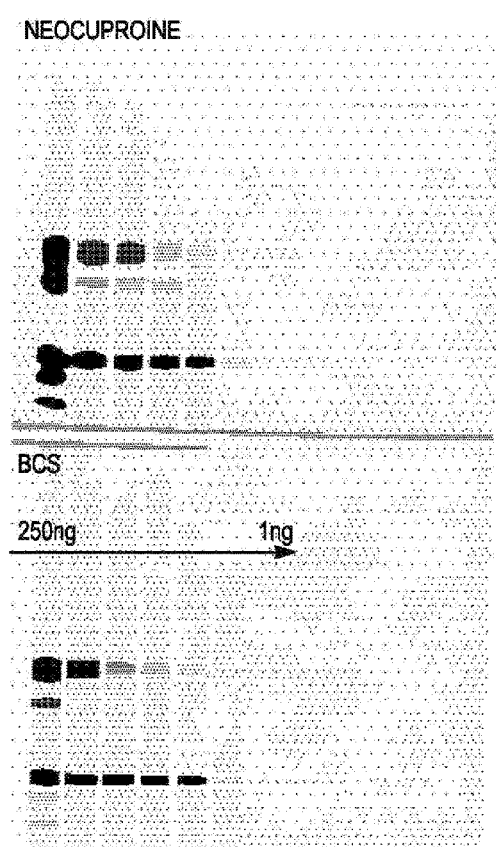
FIG. 15A1          FIG. 15A2

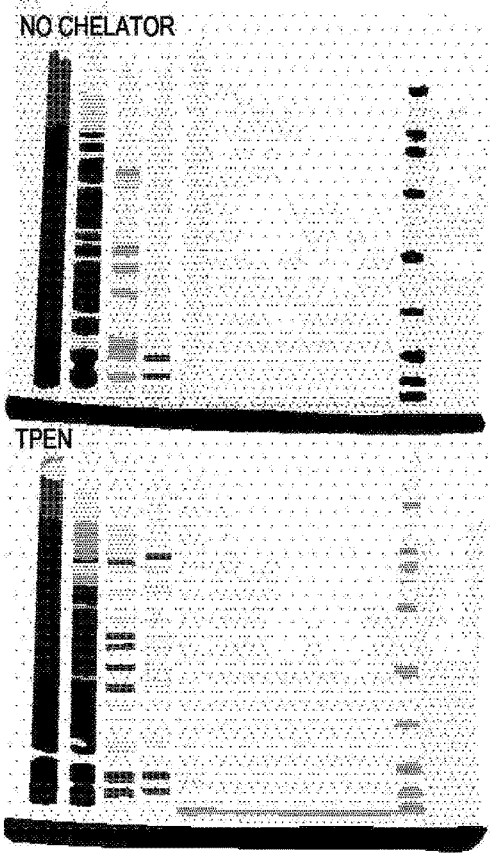 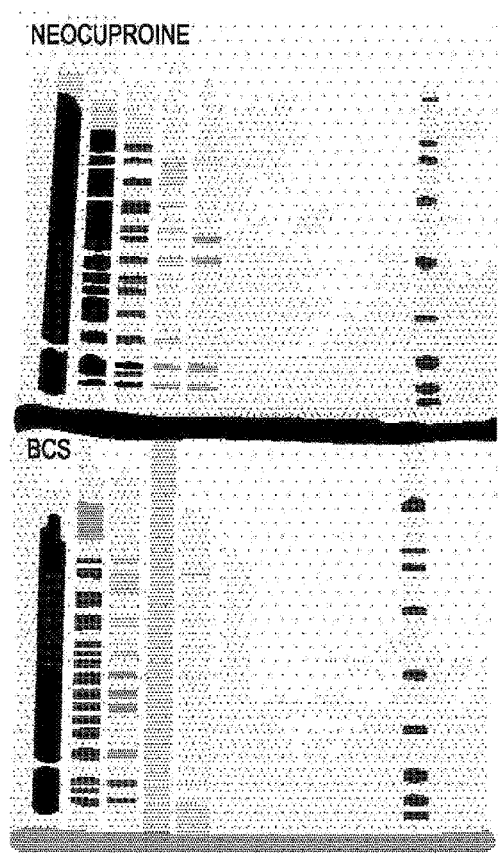
FIG. 15B1　　　　　FIG. 15B2

LANES 1 AND 4: CONTROL UNFED
LANES 2: GalNAz FED, SURFACE LABELED LIVE CELLS, NO PERM
LANES 3: GalNAz FED, TOTAL CELL LYSATES LABELED
LANES 3: ManNAz FED, SURFACE LABELED LIVE CELLS, NO PERM
LANES 3: ManNAz FED, TOTAL CELL LYSATES LABELED

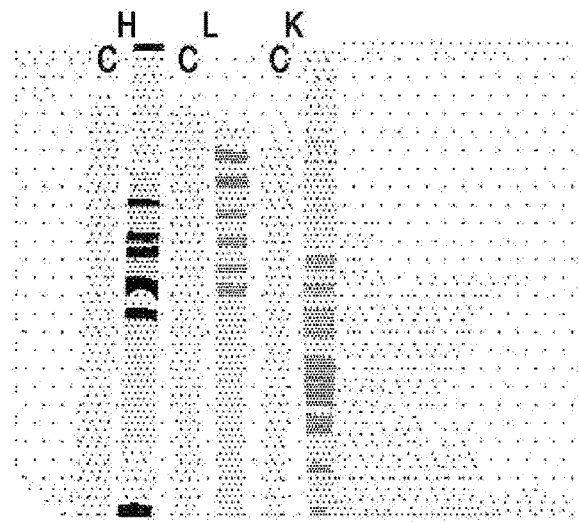
FIG. 21A1
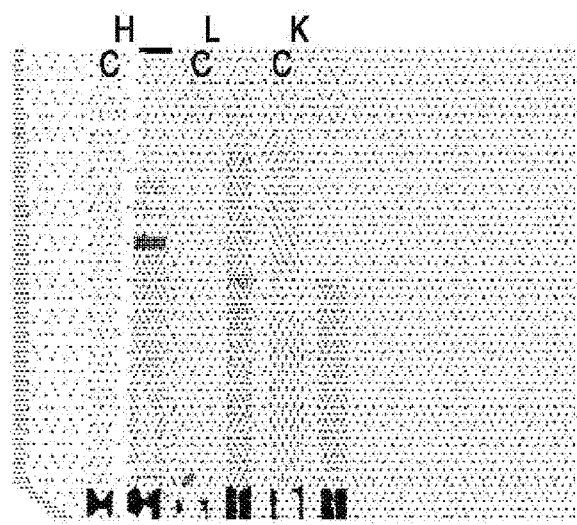
FIG. 21A2

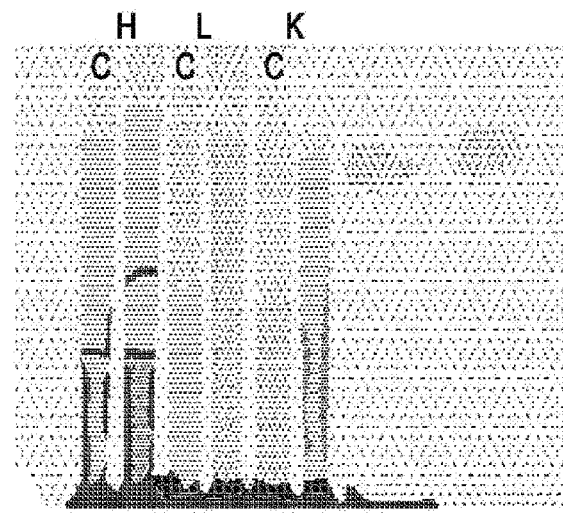
FIG. 21B1
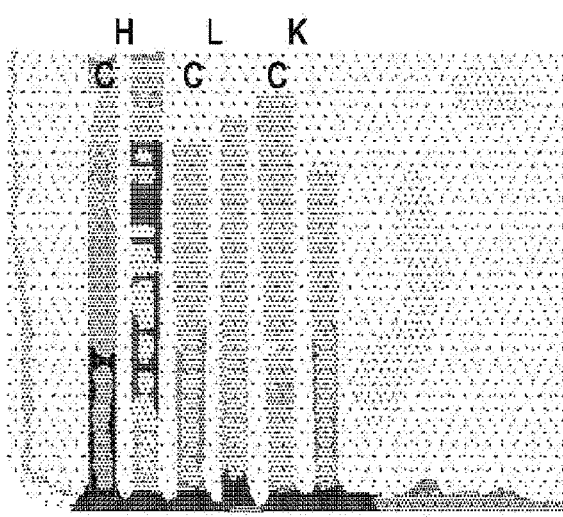
FIG. 21B2

LABELING AND DETECTION OF POST TRANSLATIONALLY MODIFIED PROTEINS

CROSS REFERENCE TO RELATED APPLICATION(S)

This application claims is a Continuation of U.S. application Ser. No. 11/674,140, filed Feb. 12, 2007, which claims the benefit of priority to U.S. Provisional Application No. 60/772,221, filed Feb. 10, 2006 and U.S. Provisional Application No. 60/804,640, filed Jun. 13, 2006, the contents of which are incorporated by reference as if set forth fully herein.

FIELD OF THE INVENTION

The invention generally relates to methods of labeling post translationally modified biomolecules using metabolic, enzymatic, or chemical incorporation of azide or alkyne-labeled macromolecules followed by chemical conjugation with paired azide, alkyne, activated alkyne, or triarylphosphine reporter molecules appended to proteins post translation.

BACKGROUND INFORMATION

Protein glycosylation is one of the most abundant post-translational modifications and plays a fundamental role in the control of biological systems. For example, carbohydrate modifications are important for host-pathogen interactions, inflammation, development, and malignancy (Varki, A. *Glycobiology* 1993, 3, 97-130; Lasky, L. A. *Annu. Rev. Biochem.* 1995, 64, 113-139. (c) Capila, I.; Linhardt, R. J. *Angew. Chem., Int. Ed.* 2002, 41, 391-412; Rudd, P. M.; Elliott, T.; Cresswell, P.; Wilson, I. A.; Dwek, R. A. *Science* 2001, 291, 2370-2376.) One such covalent modification is O-GlcNAc glycosylation, which is the covalent modification of serine and threonine residues by D-N-acetylglucosamine (Wells, L.; Vosseller, K.; Hart, G. W. *Science* 2001, 291, 2376-2378; Zachara, N. E.; Hart, G. W. *Chem. Rev.* 2002, 102, 431). The O-GlcNAc modification is found in all higher eukaryotic organisms from *C. elegans* to man and has been shown to be ubiquitous, inducible and highly dynamic, suggesting a regulatory role analogous to phosphorylation. However, the regulatory nature of the modification (i.e., dynamic, low cellular abundance) also represents a central challenge in its detection and study.

A common method to observe O-GlcNAc involves labeling proteins with β-1,4-galactosyltransferase (GalT), an enzyme that catalyzes the transfer of [$^3$H]-Gal from UDP-[$^3$H]galactose to terminal GlcNAc groups (Roquemore, E. P.; Chou, T. Y.; Hart, G. W. *Methods Enzymol.* 1994, 230, 443-460). Unfortunately, this approach is expensive, involves handling of radioactive material, and requires exposure times of days to months. Antibodies and lectins offer alternative means of detection, but they can suffer from weak binding affinity and limited specificity (Snow, C. M.; Senior, A.; Gerace, L. *J. Cell Biol.* 1987, 104, 1143-1156; Corner, F. I.; Vosseller, K.; Wells, L.; Accavitti, M. A.; Hart, G. W. *Anal. Biochem.* 2001, 293, 169-177).

Isolated or synthesized antibodies, such as IgGs, are used therapeutically and for diagnostic and research purposes. By labeling antibodies with detectable labels, such as, for example, fluorophores, antibodies can be used to specifically detect target biological molecules or cells. Antibodies may also be tagged with binding reagents, such as, for example, biotin, so that they may be used to specifically bind target biological molecules or cells, followed by purification of the biological molecule or cell by using a reagent that binds to the tagged antibody, for example, streptavidin. Antibodies have generally been labeled at cysteine or lysine residues, which may often be present in the Fab, or binding portion of the antibody. Adding tags or labels in this region may disrupt or at least alter the binding properties of the antibody. Further, it is often difficult to quantitate the number of labeled molecules attached to each antibody.

One important class of glycoproteins is antibodies. Therapeutic monoclonal antibodies (Mabs) have become indispensable drugs to combat cancer, rheumatoid arthritis, macular degeneration, and other diseases or conditions. However, antibodies generated in non-human cell lines may have antigenic features recognized as foreign by the human immune system, limiting the antibodies' half-life and efficacy. Incorporating human IgG sequences into transgenic mice has reduced, but not eliminated, immunogenicity problems. Besides the protein sequence, the nature of the oligosaccharides attached to the IgG has a profound effect on immune-system recognition. Because glycosylation is cell type specific, IgGs produced in different host cells contain different patterns of oligosaccharides, which could affect the biological functions. Even where cells, such as human embryonic stem cells, are grown on mouse feeder layers in the presence of animal-derived serum replacements, the cells incorporated a nonhuman, and immunogenic, sialic acid, and the sialic acid was then found on the cell surface. (Martin, M. J., et al., Nature Medicine, 2005, 11:228-232). Although the therapeutic antibody industry has tried to avoid these problems by producing less antigenic IgG with defucosylated oligosaccharides, defucosylated antibodies are not equivalent to humanized antibodies, and may still have immunogenecity issues, as well as having different half-lives than natural human antibodies.

Metabolic oligosaccharide engineering refers to the introduction of subtle modifications into monosaccharide residues within cellular glycans. Researchers have used metabolic engineering to disrupt glycan biosynthesis, chemically modify cell surfaces, probe metabolic flux inside cells, and to identify specific glycoprotein subtypes from the proteome. (reviewed in Dube, D. H., and Bertozzi, C. R., Current Opinion in Chemical Biology, 2003, 7:616-625).

There is a need for antibodies that have tags or labels at sites other than the binding region, and for antibodies that may be easily labeled using simple and efficient chemical reactions. There is also a need for antibodies that have post-translational modifications that are more like human antibodies.

SUMMARY OF THE INVENTION

Provided in certain embodiments are methods for enzymatically labeling a glycoprotein with an azide moiety. In one aspect a glycoprotein is contacted with UDP-GalNAz in the presence of an appropriate enzyme. In one aspect the enzyme is Gal T. In another aspect the enzyme is a modified Gal T enzyme. These azido modified glycoproteins can then be conjugated t a wide variety of reporter molecules, carrier molecules or solid supports provided that they contain an azide reactive group. In one aspect the azide reactive group is a terminal alkyne such that the conjugation reaction utilizes copper (I) catalyzed cycloaddition chemistry. In another aspect the azide reactive group is a phosphine such that the conjugation reaction performed is a Staudinger ligation type reaction.

In another embodiment is provided a method for forming a reporter molecule-glycoprotein conjugate with an immobilized azido modified glycoprotein. Glycoproteins are modified with azido sugars either metabolically or enzymatically and then immobilized on a solid or semi-solid matrix. In one embodiment the solid or semi-solid matrix is a slide, an array, polymeric particle or a gel matrix. In a particular aspect the azido modified glycoproteins are separated by gel electrophoresis or capillary electrophoresis. The immobilized azido modified glycoprotein is contacted with an azide reactive reporter molecule wherein the conjugate is formed either in a click chemistry type reaction or a Staudinger ligation type reaction. Subsequently the glycoprotein conjugate is detected after illumination with an appropriate wavelength.

The azide-alkyne [3+2] cycloaddition is a chemoselective ligation reaction that is catalyzed by the addition of copper (I). Although the reaction has been applied to a variety of different bioconjugation reactions over the past several years, it has never been applied to the in-gel fluorescence detection of modified proteins. The procedure involves the selective tagging of proteins with reactive probes containing either azide or alkyne groups. The reactive probes can be toward total proteins, such as those that label specific amino acids like lysines or cysteines, or they can label (or derivatize) post-translationally modified amino acids within the proteins, such as phosphoamino acids or glycosylated amino acids. Additionally, protein modification can take place in vivo by metabolic labeling. This involves feeding cultured cells, bacteria, plants, or animals tagged metabolic precursors that are incorporated into specific molecules by the intracellular enzymatic machinery. Primary protein labeling can be performed with an azide or alkyne probe as long as the detection is carried out with the alternate of the pair. Once the primary protein labeling step is completed, cellular extracts (or fractions) are separated by 1-D or 2-D gel electrophoresis.

The methods described for detection of proteins in gels can be completed within 3-4 hours, or less. The method is devoid of the typical problems encountered with antibody detection on blots including the requirement to optimize primary and secondary antibody concentrations and issues of non-specific binding of the antibodies. Finally, it is well-documented in-gel digested proteins are more compatible with detection by mass spectrometry than are electroblotted proteins.

BRIEF DESCRIPTION OF THE DRAWINGS

FIG. 1: FIGS. 1A, 1B and 1C show certain embodiments of metabolic labeling with unnatural azido-containing sugars.

FIG. 6: Shows the Enzymatic Labeling and Detection of α-crystallin O-GlcNAc: schematically (FIGS. 6A1 and 6A2) and detection after separation on a gel (FIGS. 6B1 and 6B2).

FIG. 10.

FIG. 14 depicts gels showing the results of separating proteins labeled using the click reaction with different chelators. 2.5 μg each of azido-ovalbumin and azido-myoglobin spiked into 80 ug of unlabeled Jurkat lysate was labeled with TAMRA alkyne for 2 hrs. The reaction contained 50 mM TRIS pH8, 25% propylene glycol, 1 mM CuSO$_4$, 5 mM sodium ascorbate, 20 uM TAMRA alkyne. The reactions were performed with and without chelator (10 mM TPEN [FIG. 14A1, upper gel], EDTA [FIG. 14A2, upper gel], bathocuproine disulfonic acid (BCS) [FIG. 14A1, middle gel] or neocuproine [FIG. 14A2, middle gel]). Control reactions were performed without CuSO$_4$ [FIG. 41A1, lower gel] or without chelator [FIG. 14A2, lower gel]. After labeling, the samples were precipitated, resolubilized in 7 mM urea/2 mM thiourea/65 mM DTT/2% CHAPS/and approximately 30 μg was analyzed on 2-D gels (pH 4-7 IEF strips, 4-12% BIS-TRIS gels with MOPS buffer). The TAMRA signal was imaged at 532 nm excitation, 580 long pass emission on a Fuji FLA3000 (14A) then the gels were post-stained with Sypro® Ruby total protein gel stain (FIGS. 14B1 and 14B2).

FIG. 15 depicts gels showing the results of separating proteins labeled using the click reaction with different chelators. The samples and click labeling conditions are the same as for FIG. 14, except that chelator treatments include addition of either 5 mM TPEN, BCS or Neocuproine at the beginning of the reaction. After labeling, the samples were precipitated, resolubilized in LDS buffer+5 mM TCEP and serial 2-fold dilutions were performed. Dilutions were loaded onto 4-12% BIS-TRIS gels with MOPS running buffer (250 ng each of ovalbumin and myglobin in lane 1). FIGS. 15A1 and 15A2 show that the chelators reduce the background of the image for the TAMRA signal without compromising sensitivity. In FIGS. 15B1 and 15B2, post-staining with Sypro® Ruby total protein gel stain shows that the band resolution is much better for the samples with chelator.

FIG. 19.

FIG. 21: shows the results of gel analysis of labeled glycoproteins in live animals. The upper panels (FIGS. 21A1 and 21B1) show 1-D gels of labeled tissue proteins from heart muscle (H), liver (L), or kidney (K). Lower panels (FIGS. 21A2 and 21B2) show same gels after post-staining with SYPRO Ruby.

DETAILED DESCRIPTION OF THE INVENTION

Definitions and Abbreviations

Figure 2A:
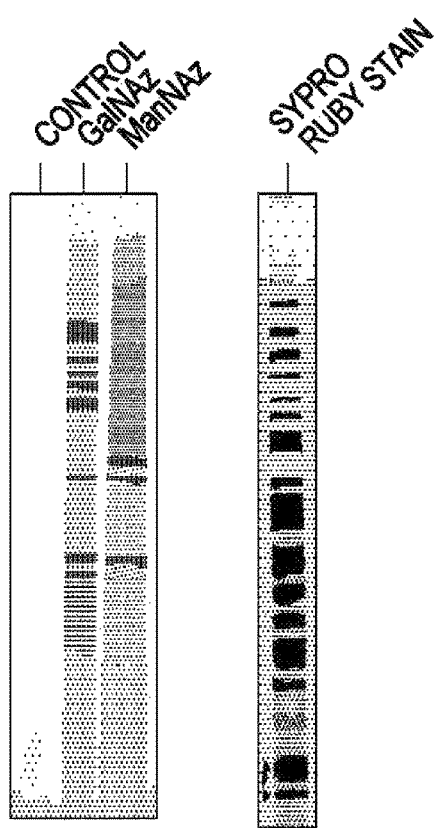
FIG. 2: Shows metabolic labeling and "click" detection of glycoprotein subclasses schematically (FIG. 2C) and detection after separation on a gel (FIGS. 2A and 2B).

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms and abbreviations (Table 1) are defined for purposes of the invention as described herein.

TABLE 1

| List of Abbreviations | |
|---|---|
| Abbreviation | Term. |
| GalNAz | N-alpha-azidoacetylgalactosamine. |
| GlcNAz | N-alpha-azidoacetylglucosamine. |
| GalNAc | N-acetylgalactosamine. |
| GlcNAc | N-acetylglucosamine |
| LOS | Lipooligosaccharide. |
| ManLev | N-levulinoylmannosamine. |
| ManNAc | N-acetylmannosamine. |
| ManNAz | N-alpha-azidoacetylmannosamine. |
| ManNBut | N-butanoylmannosamine. |
| ManNProp | N-propanoylmannosamine. |
| NCAM | neural cell adhesion molecule. |
| PSA | Polysialic acid. |
| Endo H | Endoglycosidase H |
| Endo M | Endoglycosidase M |

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.) VOGEL'S ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R''' and R'''' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P), silicon (Si), and selenium (Se).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "Carboxyalkyl" as used herein refers to a group having the general formula —(CH$_2$)$_n$COOH wherein n is 1-18.

The term "activated alkyne," as used herein, refers to a chemical moiety that selectively reacts with an azide reactive group on another molecule to form a covalent chemical bond between the activated alkyne group and the alkyne reactive group. Examples of alkyne-reactive groups include azides. "Alkyne-reactive" can also refer to a molecule that contains a chemical moiety that selectively reacts with an alkyne group.

The term "affinity," as used herein, refers to the strength of the binding interaction of two molecules, such as an antibody and an antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "High affinity" refers to a ligand that binds to an antibody having an affinity constant (K$_a$) greater than 10$^4$ M$^{-1}$, typically 10$^5$-10$^{11}$ M$^{-1}$; as determined by inhibition ELISA or an equivalent affinity determined by comparable techniques such as, for example, Scatchard plots or using K$_d$/dissociation constant, which is the reciprocal of the K$_a$.

The term "alkyne reactive," as used herein, refers to a chemical moiety that selectively reacts with an alkyne modified group on another molecule to form a covalent chemical bond between the alkyne modified group and the alkyne reactive group. Examples of alkyne-reactive groups include azides. "Alkyne-reactive" can also refer to a molecule that contains a chemical moiety that selectively reacts with an alkyne group.

The term "antibody," as used herein, refers to a protein of the immunoglobulin (Ig) superfamily that binds noncovalently to certain substances (e.g. antigens and immunogens) to form an antibody-antigen complex. Antibodies can be endogenous, or polyclonal wherein an animal is immunized to elicit a polyclonal antibody response or by recombinant methods resulting in monoclonal antibodies produced from hybridoma cells or other cell lines. It is understood that the term "antibody" as used herein includes within its scope any of the various classes or sub-classes of immunoglobulin derived from any of the animals conventionally used.

The term "antibody fragments," as used herein, refers to fragments of antibodies that retain the principal selective binding characteristics of the whole antibody. Particular fragments are well-known in the art, for example, Fab, Fab', and F(ab')$_2$, which are obtained by digestion with various proteases, pepsin or papain, and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

The term "antigen," as used herein, refers to a molecule that induces, or is capable of inducing, the formation of an antibody or to which an antibody binds selectively, including but not limited to a biological material. Antigen also refers to "immunogen". The target-binding antibodies selectively bind an antigen, as such the term can be used herein interchangeably with the term "target".

The term "anti-region antibody," as used herein, refers to an antibody that was produced by immunizing an animal with a select region that is a fragment of a foreign antibody wherein only the fragment is used as the immunogen. Regions of antibodies include the Fc region, hinge region, Fab region, etc. Anti-region antibodies include monoclonal and polyclonal antibodies. The term "anti-region fragment" as used herein refers to a monovalent fragment that was generated from an anti-region antibody of the present invention by enzymatic cleavage.

The term "aqueous solution," as used herein, refers to a solution that is predominantly water and retains the solution characteristics of water. Where the aqueous solution contains solvents in addition to water, water is typically the predominant solvent.

The term "azide reactive," as used herein, refers to a chemical moiety that selectively reacts with an azido modified group on another molecule to form a covalent chemical bond between the azido modified group and the azide reactive group. Examples of azide-reactive groups include alkynes and phosphines (e.g. triaryl phosphine). "Azide-reactive" can also refer to a molecule that contains a chemical moiety that selectively reacts with an azido group.

The term "biomolecule," as used herein, refers to proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides, polysaccharides, which having characteristics typical of molecules found in living organisms and may be naturally occurring or may be artificial (not found in nature and not identical to a molecule found in nature).

The term "buffer," as used herein, refers to a system that acts to minimize the change in acidity or basicity of the solution against addition or depletion of chemical substances.

The term "carrier molecule," as used herein, refers to a biological or a non-biological component that is covalently bonded to compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term, "chemical handle" as used herein refers to a specific functional group, such as an azide, alkyne, activated alkyne, phosphite, phosphine, and the like. The chemical handle is distinct from the reactive group, defined below, in that the chemical handle are moieties that are rarely found in naturally-occurring biomolecules and are chemically inert towards biomolecules (e.g, native cellular components), but when reacted with an azide- or alkyne-reactive group the reaction can take place efficiently under biologically relevant conditions (e.g., cell culture conditions, such as in the absence of excess heat or harsh reactants).

The term "click chemistry," as used herein, refers to the Huisgen cycloaddition or the 1,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

The term "cycloaddition" as used herein refers to a chemical reaction in which two or more $\pi$ (pi)-electron systems (e.g., unsaturated molecules or unsaturated parts of the same molecule) combine to form a cyclic product in which there is a net reduction of the bond multiplicity. In a cycloaddition, the $\pi$ (pi) electrons are used to form new $\pi$ (pi) bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 1,3-dipolar cycloadditions, occur between a 1,3-dipole and a dipolarophile and are typically used for the construction of five-membered heterocyclic rings. The term "[3+2] cycloaddition" also encompasses "copperless" [3+2] cycloadditions between azides and cyclooctynes and difluorocyclooctynes described by Bertozzi et al. J. Am. Chem. Soc., 2004, 126:15046-15047.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "directly detectable" as used herein refers to the presence of a material or the signal generated from the material is immediately detectable by observation, instrumentation, or film without requiring chemical modifications or additional substances.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($10^{th}$ edition, CD-ROM, September 2005), which is herein incorporated by reference in its entirety.

The term "glycoprotein," as used herein, refers to a protein that has been glycosylated and those that have been enzymatically modified, in vivo or in vitro, to comprise a sugar group.

The term "kit," as used herein, refers to a packaged set of related components, typically one or more compounds or compositions.

The term "label," as used herein, refers to a chemical moiety or protein that is directly or indirectly detectable (e.g. due to its spectral properties, conformation or activity) when attached to a target or compound and used in the present methods, including reporter molecules, solid supports and carrier molecules. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidate (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($9^{th}$ edition, CD-ROM, September 2002), supra.

The term "linker" or "L", as used herein, refers to a single covalent bond or a series of stable covalent bonds incorporating 1-30 nonhydrogen atoms selected from the group consisting of C, N, O, S and P. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid. In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available. An exemplary cleavable group, an ester, is cleavable group that may be cleaved by a reagent, e.g. sodium hydroxide, resulting in a carboxylate-containing fragment and a hydroxyl-containing product.

The term "post translational moiety" as used herein refers to any moiety that is naturally appended to a protein post translationally by a recombinant or naturally occurring enzyme. Examples include, but are not limited to, acetate, phosphate, various lipids and carbohydrates. As used herein "azido or alkyne modified post translational moiety" means any post translational moiety that comprises an azido or alkyne group, which are groups rarely round in naturally occurring biological systems.

The terms "protein" and "polypeptide" are used herein in a generic sense to include polymers of amino acid residues of any length. The term "peptide" is used herein to refer to polypeptides having less than 100 amino acid residues, typically less than 10 amino acid residues. The terms apply to amino acid polymers in which one or more amino acid residues are an artificial chemical analogue of a corresponding naturally occurring amino acid, as well as to naturally occurring amino acid polymers.

The term "purified" as used herein refers to a preparation of a glycoprotein that is essentially free from contaminating proteins that normally would be present in association with the glycoprotein, e.g., in a cellular mixture or milieu in which the protein or complex is found endogenously such as serum proteins or cellular lysate.

The term "reactive group" as used herein refers to a group that is capable of reacting with another chemical group to form a covalent bond, i.e. is covalently reactive under suitable reaction conditions, and generally represents a point of attachment for another substance. As used herein, reactive groups refer to chemical moieties generally found in biological systems and that react under normal biological conditions, these are herein distinguished from the chemical handle, defined above, the azido and activated alkyne moieties of the present invention. As referred to herein the reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

The term "reporter molecule" refers to any moiety capable of being attached to a modified post translationally modified protein of the present invention, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

The term "sample" as used herein refers to any material that may contain an analyte for detection or quantification or a modified post translationally modified protein of the present invention. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected one or more compounds described herein to be bound to the solid support.

The term "Staudinger ligation" as used herein refers to a chemical reaction developed by Saxon and Bertozzi (E. Saxon and C. Bertozzi, Science, 2000, 287: 2007-2010) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on the aryl group of a triarylphosphine (usually ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

The terms "structural integrity of the [biomolecule] is not reduced" or "preservation of the structural integrity of the [biomolecule]", as used herein, means that either: 1) when analyzed by gel electrophoresis and detection (such as staining), a band or spot arising from the labeled biomolecule is not reduced in intensity by more than 20%, and preferably not reduced by more than 10%, with respect to the corresponding band or spot arising from the same amount of the electrophoresed unlabeled biomolecule, arising from the labeled biomolecule analyzed; or 2) when analyzed by gel electrophoresis, a band or spot arising from the labeled biomolecule is not observed to be significantly less sharp than the corresponding band or spot arising from the same amount of the electrophoresed unlabeled biomolecule, where "significantly less sharp" (synonymous with "significantly more diffuse") means the detectable band or spot takes up at least 5% more, preferably 10% more, more preferably 20% more area on the gel than the corresponding unlabeled biomolecule. Other reproducible tests for structural integrity of labeled biomolecules include, without limitation detection of released amino acids or peptides, or mass spectrometry.

In general, for ease of understanding the present invention, the metabolic and enzymatic labeling of biomolecules with azide moieties, alkyne moieties or phosphine, and the chemical labeling of such moieties with azide reactive moieties, alkyne reactive moieties or phosphine reactive moieties will first be described in detail. This will be followed by some embodiments in which such labeled biomolecules can be detected, isolated and/or analyzed. Exemplified methods are then disclosed.

Modification of Biomolecules

The tagging/labeling of biomolecules, including glycoproteins, phosphoproteins, isoprenylated proteins, can utilize various post-translation modifications to incorporate a bioorthoganol moiety into a biomolecule followed by chemical attachment of a label (reporter molecule, solid support, and carrier molecule). An alternative approach is to incorporate a bioorthoganol moiety into the biomolecule using cellular biosynthetic pathways, or metabolic modifications. These bioorthogonol moieties are non-native, non-perturbing chemical handles possessing unique chemical functionality that can be modified through highly selective reactions. Examples of such moieties include, but are not limited to hyrazide and aminooxy derivatives, azides that can be selectively modified with phosphines (Staudinger ligation), azides that can be selectively modified with activated alkynes, and azides that can be selectively modified with terminal alkynes ("click" chemistry).

Post-translational modification is alteration of a primary structure of the protein after the protein has been translated. After translation, the post-translational modification of amino acids extends the range of functions of the protein by attaching to it other biochemical functional groups such as acetate, phosphate, various lipids and carbohydrates. In addition, the range of functions of proteins can be extended by post-translational modifications that change the chemical nature of an amino acid or by making structural changes such as disulfide bridges formation. Other post-translational modifications involve enzymes that remove amino acids from the amino end (N-terminus) of the protein, or cut the protein chain. Post-translational modifications act on individual residues either by cleavage at specific points, deletions, additions or by converting or modifying side chains.

The various post-translational modifications that can be used with the methods and compositions described herein include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a gla residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). In certain embodiments, selenoproteins are used in the methods and compositions described herein.

Glycoproteins are biomolecules composed of proteins covalently linked to carbohydrates. Certain post-translational modifications append a sugar moiety (carbohydrate or oligosaccharide) onto a protein, thereby forming a glycoprotein. The common monosaccharides found in glycoproteins include, but are not limited to, glucose, galactose, mannose, fucose, xylose, N-acetylgalactosamine (GalNAc), N-acetylglucosamine (GlcNAc) and N-acetylneuraminic acid (NANA, also known as sialic acid). In addition the sugar moiety can be a glycosyl group. In glycoproteins the carbohydrates can be linked to the protein component by either N-glycosylation or O-glycosylation. N-glycosylation commonly occurs through asparagine forming an N-glycosidic linkage via an amide group. O-glycosylation commonly occurs at hydroxylysine, hydroxyproline, serine, or threonine, forming an O-glycosidic linkage.

The metabolic labeling of glycoproteins with azido sugars has been described, however these currently known methods lack sufficient methodology for detecting and isolating such azido modified glycoproteins. Provided herein are methods and compositions for the detection, isolation and/or analysis of glycosylated proteins facilitated by the incorporation and use of unnatural azido sugars into glycoproteins rather than natural sugars. In particular, presented are a novel methods for A) labeling azido modified biomolecules in solution followed by separation using methods known in the art for separating biomolecules based on size, weight and/or charge, B) labeling immobilized azido modified biomolecules and C) novel methods for enzymatically labeling a biomolecule with an azide group. These azido modified biomolecules can form conjugates with reporter molecules, carrier molecules or solid supports, provided an azide reactive group is present, using either methods known in the art or the current methods provided herein.

Also provided herein are methods and compositions for the detection, isolation and/or analysis of glycosylated proteins facilitated by the incorporation and use of unnatural alkyne containing sugars into glycoproteins rather than natural sugars. In particular, presented are a novel methods for A) labeling alkyne modified biomolecules in solution followed by separation using methods known in the art for separating biomolecules based on size, weight and/or charge, B) labeling immobilized alkyne modified biomolecules and C) novel methods for enzymatically labeling a biomolecule with an alkyne group. These alkyne modified biomolecules can form conjugates with reporter molecules, carrier molecules or solid supports, that have azide groups, using either methods known in the art or the current methods provided herein.

The methods described herein can be used for metabolic and enzymatic selective labeling of different subclasses of glycoproteins, including cell surface N- and O-linked glycoproteins and intracellular O-GlcNAc-modified proteins. Such labeling enables highly-sensitive detection of labeled glycoproteins using chromatographic and electrophoretic techniques including, but not limited to, gel electrophoresis and western blot analysis. (Dube D. H., Bertozzi C. R. (2003). *Curr Opin Chem. Biol.* October; 7(5):616-25; Boeggeman E. E., Ramakrishnan B., Qasba P. K. (2003). *Protein Expr Purif* August; 30(2):219-29; Khidekel N., Arndt S., Lamarre-Vincent N., Lippert A., Poulin-Kirstien K. G., Ramakrishnan B., Qasba P. K., Hsieh-Wilson L. C. (2003). *J Am Chem Soc* December 31; 125(52):16162-3). In certain embodiments, glycoproteins are "labeled" with azide modified sugar moieties, while in other embodiments glycoproteins are "labeled" with alkyne modified sugar moieties. This can be accomplished either metabolically, wherein cells are fed either unnatural azide containing sugars or alkyne containing sugars, or it is accomplished in vitro by enzymatic methods. In a specific embodiment of such enzymatic methods, the galactose-1-phosphate uridyl transferase (GalT) enzyme is used to incorporate a UDP-GalNAz moiety to a protein.

Phosphoproteins are biomolecules composed of proteins having a phosphate group covalently linked to one or more serine, threonine, or tyrosine residues. Phosphate groups are added to proteins post translationally by kinases and removed by phoshphorylases; changes in the phosphorylation state of a protein can have a significant effect on its structure and function.

Phosphoproteins and phosphopeptides can also be modified by the addition of an azide or alkyne group. For example, a one or more phosphate groups on a phosphoprotein can be converted to an azido or alkyne, by using base treatment to remove the phosphate group of phosphoserine, converting it to dehydroamino-2-butyric acid, or to remove the phosphate group of threonine to convert it to dehydroalanine. The dephosphorylated protein can then be reacted with a thiol or amine-containing compound that also comprises an azide or terminal alkyne to form an azido or alkyne labeled (phospho)protein. A phosphoprotein so modified is referred to herein as a modified phosphoproteins, although all phosphate groups of the modified phosphoprotein may have been removed.

The invention thus includes a method of modifying a phosphoprotein to include an alkyne or azido group, in which the method includes: contacting a phosphoprotein that includes at least one phosphoserine residue or at least one phosphothreonine residue with a base solution that removes phosphates from threonine and serine residues of the phosphorylated protein to form a protein comprising at least one dehydroalanine or at least one dehydroamino-2-butyric acid; contacting the dehydroalanine or dehydroamino-2-butyric acid with a compound that includes a thio or amine group and has an azide or terminal alkyne to form an azido or alkyne modified protein; and contacting the azido or terminal alkyne-modified protein with a reporter molecule, carrier molecule, or solid support that comprises an azido moiety, where the phosphoprotein is labeled with a terminal alkyne, or a reporter molecule, carrier molecule, or solid support that comprises an alkyne, where the phosphoprotein is modified to have an azido group. The modified phosphoproteins comprising azido or alkyne groups can be used in the labeling methods provided herein.

Metabolic Modification

The modified proteins used in the methods and compostions described herein can be formed by in vivo metabolic modification. Such in vivo metabolic modification of proteins can be accomplished using the methods described in U.S. Pat. No. 6,936,701. In general, cells are fed non-natural sugars having a desired functional group including, but not limited to, azide moieties and alkyne moieties and phosphine moieties. These non-natural sugars are then attached to the protein forming a glycoprotein conjugate which is then expressed by the cell. The modified proteins are either naturally secreted and isolated, or they can be present, for example, in a cell lysate, extracellular milieu, cell fraction, or isolated from a complex protein mixture. The resulting modified protein is then used in the methods and compositions described herein.

In certain embodiments, such non-natural sugars contain a moiety that facilitates entry into the cell including, but not limited to, a tetraacetyl moiety. Thus, non-natural sugar substrates, used in the metabolic labeling of proteins used in the methods and compositions described herein, include small groups that the cellular machinery would be more likely to incorporate, and not recognize as being foreign. The cellular metabolic machinery incorporates the substrates into N- or O-linked glycans attached to the proteins.

Figure 2B:
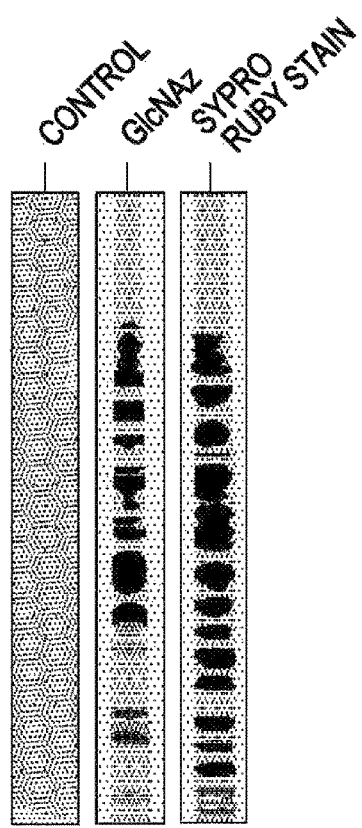
Figure 2C:
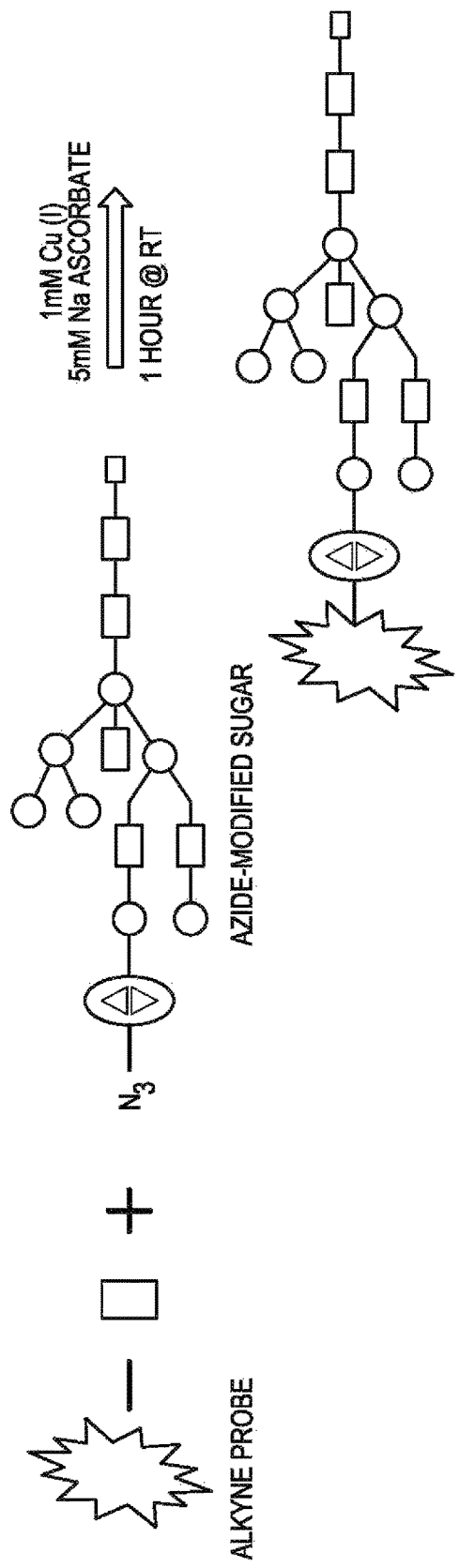
Figure 3A:
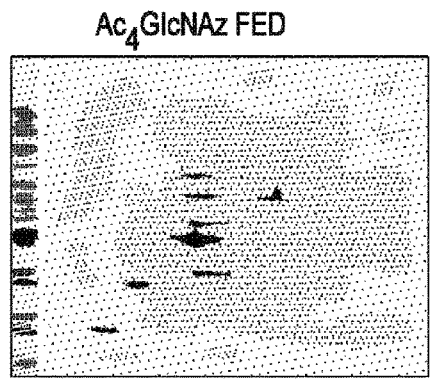
FIG. 3: Shows separation of Ac$_4$GlcNAz-treated soluble Jurkat cell proteins by 2-D gels (FIGS. 3A and 3B) and controls (FIGS. 3C and 3D) compared to the same gel stained with SYPRO® Ruby total protein stain.
Figure 3B:
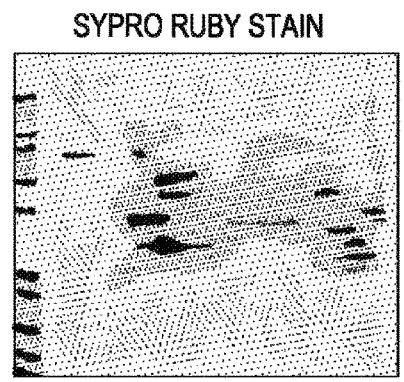
Figure 3C:
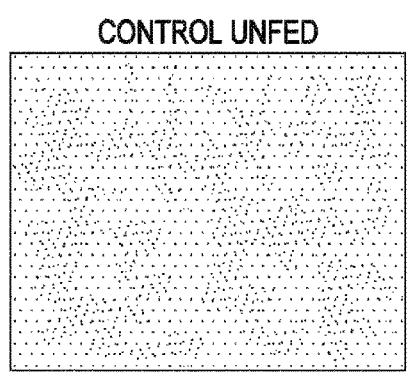
Figure 3D:
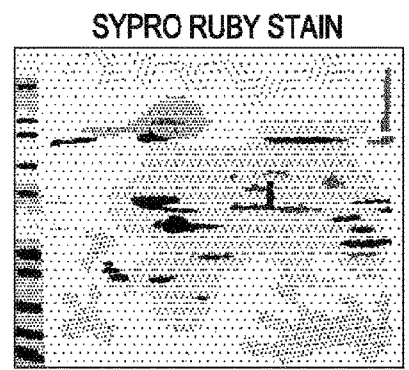

One aspect of the methods provided herein involves metabolically labelling proteins with non-natural sugar substrates that have azido groups or alkyne groups that may be used for "click" chemistry as described herein. Another aspect of the methods provided herein involves metabolically labelling proteins with non-natural sugar substrates that have azido groups or phosphine groups that may be used in a Staudinger ligation as described herein. Such non-natural sugars can be synthesized using methods known in the art. In certain embodiments, the non-natural sugars used to metabolically label proteins are non-natural azido-containing sugars including, but are not limited to, GlcNAz, GalNAz and ManNAz, or tetraacetylated non-natural azido-containing sugars including, but not limited to, GlcNAz, ManNAz, and GalNAz. In certain embodiments, the non-natural sugars used to metabolically label glycoproteins or specific subsets of cellular glycoproteins in cultured cells are non-natural azido-containing sugars including, but are not limited to, GlcNAz, GalNAz and ManNAz, or tetraacetylated non-natural azido-containing sugars including, but not limited to, GlcNAz, ManNAz, and GalNAz. Certain embodiments of metabolic labeling with non-natural azido-containing sugars is shown in FIG. 1, and described in Example 1, wherein cells are fed non-natural azido-containing sugars to obtain modified proteins, including modified glycoproteins, used in the methods and compositions described herein. FIG. 2 shows gel images of modified proteins obtained from Jurkat cells which were fed $Ac_4ManNAz$ or $Ac_4GalNAz$ for 3 days (FIG. 2A) or $Ac_4GlcNAz$ overnight (FIG. 2B). The modified proteins were obtained from harvested cells and labeled with a fluorescent alkyne probe using "click" chemistry (FIG. 2C). The gels were then stained with a protein stain that has different excitation/emission properties than the alkyne probe, thereby demonstrating the selectivity of "click" chemistry for glycoprotein labeling.

Proteins metabolically labeled with non-natural sugars, followed by labeling using "click" chemistry or Staudinger ligation, can be detected using 2-D gel electrophoresis. FIG. 3 shows a 2-D gel separation of proteins obtained from soluble Jurkat cell treated with $Ac_4GlcNAz$ and labeled with a fluorescent alkyne probe using click chemistry. The control cell culture was not fed $Ac_4GlcNAz$ and therefore does not show the presence of the fluorescent alkyne probe. However, staining with a protein stain shows the presence of protein in both gels.

The unnatural sugars described herein can be incorporated into various glycoproteins and subclasses of glycoproteins. In certain embodiments, the glycoproteins are antibodies from antibody-producing cells such as, by way of example only, hybridoma cells, and any other cell that produces antibodies or recombinant antibodies. Once the in vivo labeled antibodies are released and isolated from the cells, the labeled antibodies may be directly labeled using an azide reactive reporter molecule, solid support or carrier molecule, as described herein. The reporter molecules can include, but are not limited to labels, while the solid supports can include, but are not limited to, solid support resins, microtiter plates and microarray slides. The carrier molecules can include, but are not limited to, affinity tags, nucleotides, oligonucleotides and polymers.

Enzymatic Modification

The modified proteins used in the methods and compositions described herein can be modified in vitro using enzymatic post-translational modification. In certain embodiments the post-translational modifications used in the methods and compostions described herein include, but are not limited to, glycosylation, isoprenylation, lipoylation and phosphorylation. In certain embodiments, such post-translational modifications are used to modify proteins with azide moieties, alkyne moieties, or phosphine moieties. Such phosphine moieties include, but are not limited to, triaryl phosphines. Certain embodiments utilize β-1,4-galactosyltransferase(GalT), or a mutant thereof, to modify glycosylated proteins with azide moieties, alkyne moieties, or phosphine moieties. β-1,4-galactosyltransferase (GalT) is an enzyme that can catalyze the transfer of galactose from uridine diphosphate-GalNAz (UDP-GalNAz) to terminal GlcNAc groups. Thus, glycoproteins are enzymatically labeled in vitro with azide modified sugar moieties, alkyne modified sugar moieties, or phosphine modifier sugar moieties. In another embodiment, GalT has been mutated, such as with a single Y289L mutation, to enlarge the binding pocket and to enhance the catalytic activity toward substrates. Other mutations to GalT are contemplated such that the mutation provide enlargement of the binding pocket and enhancement of the catalytic activity toward substrates. As shown in FIGS. 6A1, 6A2, 6B1 and 6B2, a mutant of β-GalT enzyme (β-GalT1) can be used to enzymatically label an O-GlcNAc containing protein with azide (UDP-GalNAz). In addition FIGS. 6A1, 6A2, 6B1 and 6B2 show that UDP-GalNAz is also a suitable substrate for the mutant of β-1,4-galactosyltransferase (GalT1) resulting in the ability to enzymatically attach an non-natural azido-containing sugar to a glycoprotein.

The methods and compositions described herein for enzymatically labeling glycoproteins with azido-containing sugars, alkyne-containing sugars or phosphine-containing sugars provide for the rapid, selective and sensitive detection of post-translationally modified proteins, including, but not limited to, those with post-translational glycosylations. Such detection methods utilize labeling using the selective reactivity of "click" chemistry, or Staudinger ligation, as described herein. Such labeling methods can be used to detect post-translational modifications on proteins in which such modifications were undetectable using other techniques. In certain embodiments, such labeling methods can be used to detect O-GlcNAc post-translational modifications on proteins in which such modifications are undetectable using other techniques.

In certain embodiments, enzymatic post-translational modification methods are used to selectively transfer azido, alkyne of phosphine functionality onto proteins using azido-containing substrates, alkyne-containing substrates or phosphine-containing substrates. Once transferred the modified protein can then be conjugated to a reporter molecule, solid support or carrier, molecule using a "click" chemistry, Staudinger ligation, or activated alkyne based reactions, thereby enabling detection, isolation and/or analysis of the modified protein. Thus, in certain embodiments, the in vitro enzymatic labeling allows for sensitive detection of modified proteins from cells or tissues.

In certain embodiments, such methods are used to exploit the ability of an engineered mutant of β-1,4-galactosyltransferase to selectively transfer azido functionality onto O-GlcNAc glycosylated proteins using non-natural azido-containing sugars, alkyne functionality onto O-GlcNAc glycosylated proteins using non-natural alkyne-containing sugars, or phosphine functionality onto O-GlcNAc glycosylated proteins using non-natural phosphine-containing sugars. Once transferred the azido modified glycoprotein, alkyne modified glycoprotein or phosphine modified glycoprotein can then be conjugated to a reporter molecule, solid support or carrier molecule using a "click" chemistry, Staudinger ligation or activated alkyne based reactions, thereby enabling detection, isolation and/or analysis of the modified protein. Thus, in certain embodiments, the in vitro labeling with the modified β-GalTI enzyme allows for sensitive detection of O-GlcNAc-modified proteins from cells or tissues and enables the characterization of inverse relationships between cellular O-GlcNAc modification and phosphorylation on the same proteins.

Figure 11A:
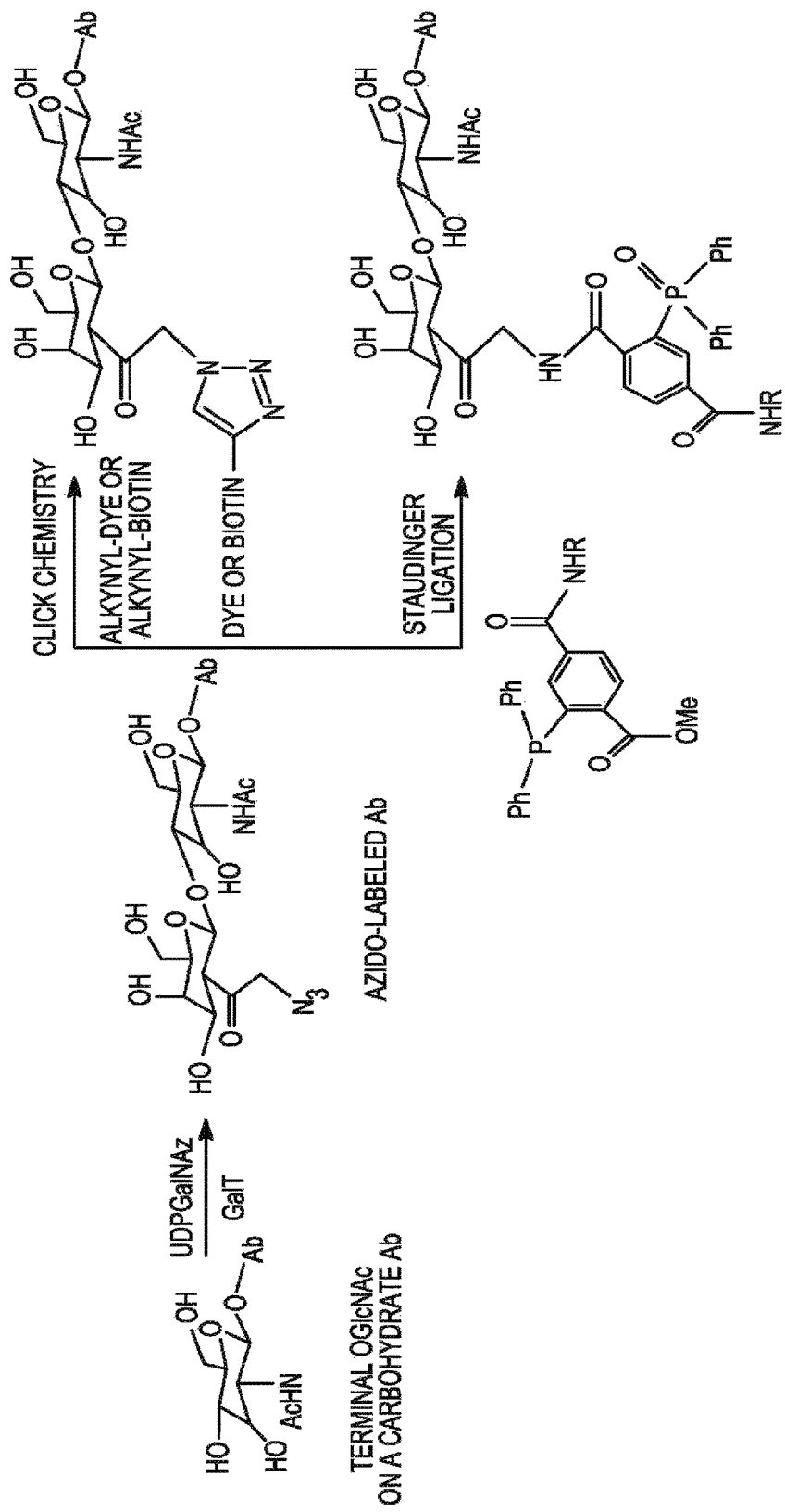
FIG. 11: Shows the (FIG. 11A) UDPGalNAz in conjunction with GalT as a novel method for labeling antibodies via reaction of the terminal OGlcNAc molecules present on antibody carbohydrates (Scheme 2) and (FIG. 11B) if no OGlcNAc sugars are present on an antibody, then use of the Endo-H (endo-β-N-acetylglucosaminidase H) enzyme will be used to generate a truncated chain which terminates with one N-acetylglucosamine residue.
Figure 11B:
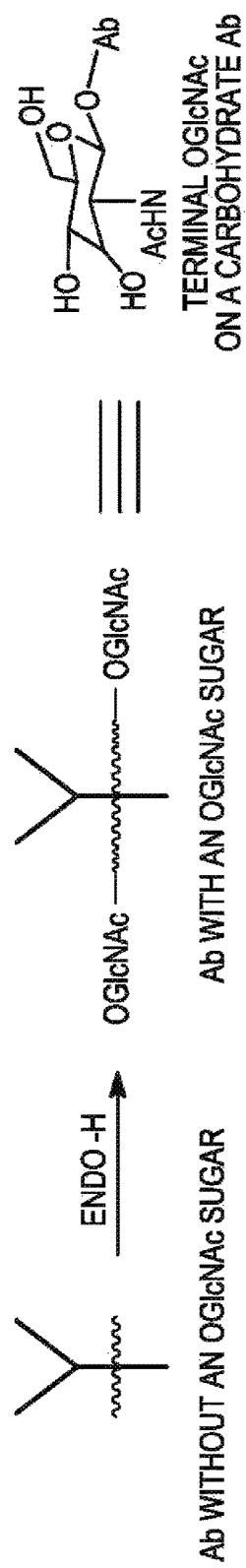
Figure 12A:
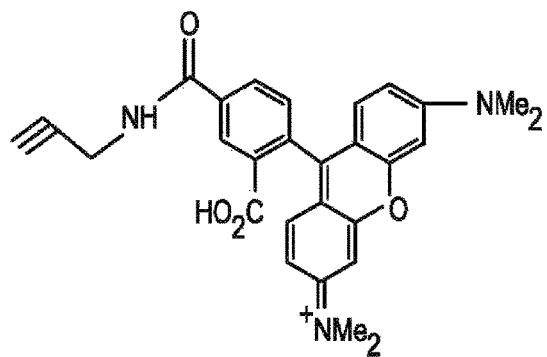
FIG. 12A) TAMRA-alkyne.
Figure 12B:
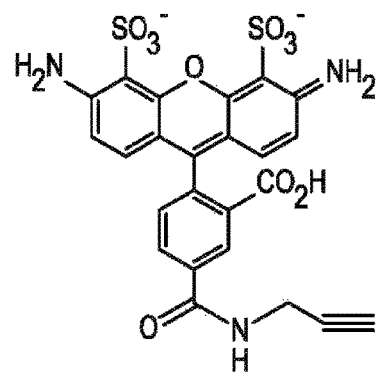
FIG. 12B) Alexa 488-Alkyne.
Figure 12C:
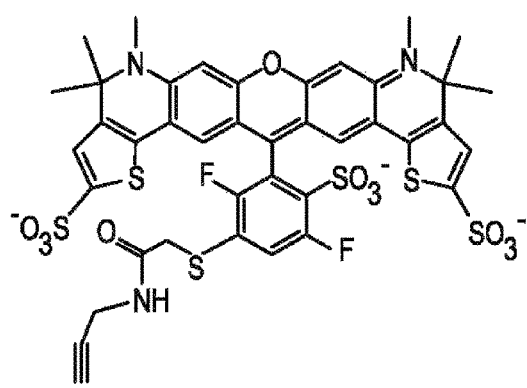
FIG. 12C) Alexa 633-Alkyne.
Figure 12D:
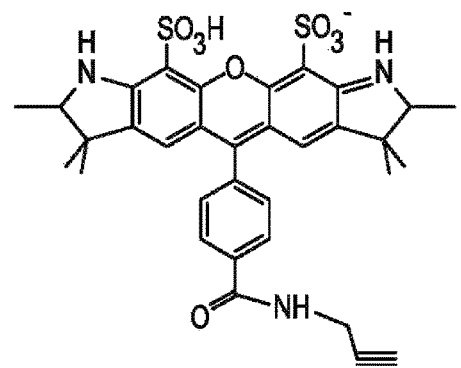
FIG. 12D) Alexa 532-Alkyne, FIG. 12E) a potential fluorogenic alkyne.
Figure 12E:
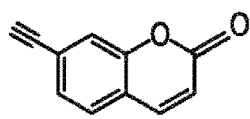
FIG. 12: Shows structures of four present (FIGS. 12A-12D) and two potential (FIGS. 12E, 12F) alkyne fluorophores that can be used to label biomolecules using the methods of the invention.
FIG. 12F) a potential fluorogenic alkyne.
Figure 12F:
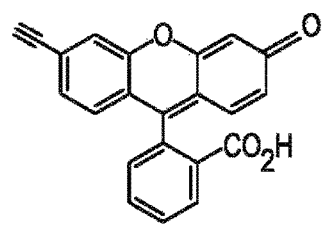
Figure 17A:
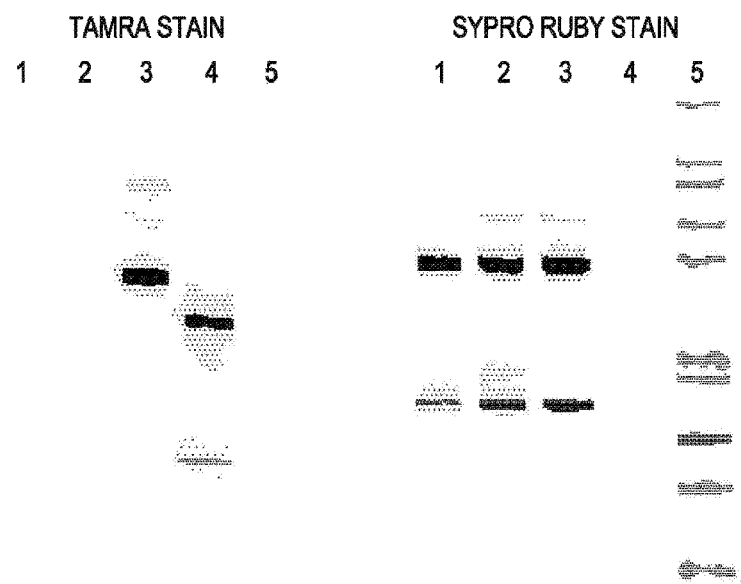
FIG. 17A) Lane 1—Goat antibody only (GAb); Lane 2—GAb with GalT1 enzyme but without UDP-GalNAz Control; Lane 3—GAb with enzyme and UDP-GalNAz. Lane 4—azide-labeled ovalbumin and myoglobin control proteins; Lane 5—MW markers unlabeled and FIG. 17B) Azide-labeled goat antibodies (from above) were run as a dilution series. Nanograms of antibodies were calculated for the heavy chains only. Gels were run, stained, and imaged as described above.
Figure 17B:
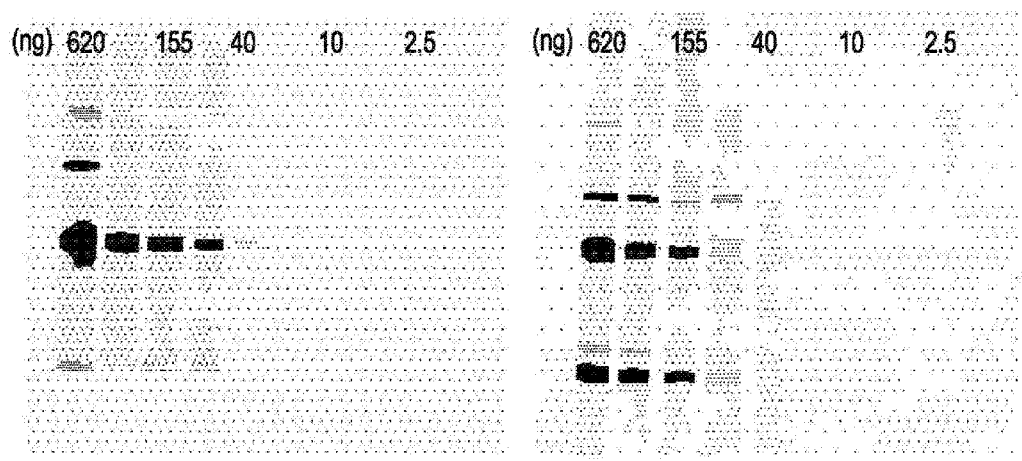
FIG. 17: Shows the enzymatic labeling of antibodies using click chemistry.

The methods and compositions described herein can be used to enzymatically label antibodies in vitro with azido-containing sugars, alkyne-containing sugars or phosphine-containing sugars can be used to label antibodies. Once the in vitro labeled antibodies are obtained, the labeled antibodies may be directly labeled using either an azide reactive, alkyne reactive or phosphine reaction reporter molecule, solid support or carrier molecule, as described herein. In certain embodiments, as shown in FIG. 11, antibodies can be enzymatically labeled with UDPGalNAz using GalT via reaction of the terminal OGlcNAc molecules present on antibody carbohydrates. "Click" chemistry or Staudinger ligation can then be used to conjugate a dye or a hapten, such as biotin, (or other reporter molecules, solid supports or carrier molecules) to the attached azide moiety. In certain embodiments, if no OGlcNAc sugars are present on an antibody, then use of the Endo-H (endo-β-N-acetylglucosaminidase H) enzyme will be used to generate a truncated chain which terminates with one N-acetylglucosamine residue (FIG. 11B). FIG. 17 shows the enzymatic labeling of Goat antibody with UDP-GalNAz followed by conjugation with an alkyne-TAMRA dye using "click: chemistry. The selectivity and specificity of such conjugations is shown from the controls and general protein staining with a SYPRO® Ruby protein stain.

The invention also includes methods for enzymatically labeling proteins via attachment of an azido or alkyne modified phosphate to the protein. Kinases that phosphorylate serine, threonine, and also tyrosine residues are known in the art and can be used for the attachment of azido or alkyne groups to a protein. Included herein is a method for forming a phosphoprotein comprising a terminal alkyne modified phosphate that includes contacting a protein with a terminal alkyne modified phosphate in the presence of an enzyme that will transfer the terminal alkyne modified phosphate to the protein to form a terminal alkyne modified phosphoprotein. In some embodiments, the protein has at least one serine, threonine, or tyrosine residue. The invention also includes methods for forming a phosphoprotein conjugate, in which the phosphoprotein conjugate is attached to a reporter molecule, solid support, or carrier molecule, in which the method includes contacting a protein with a terminal alkyne modified phosphate in the presence of an enzyme that will transfer the terminal alkyne modified phosphate to the protein to form a terminal alkyne modified phosphoprotein; and contacting the terminal alkyne modified phosphoprotein with a reporter molecule, carrier molecule or solid support that comprises an azido moiety to form phosphoprotein reporter molecule, carrier molecule or solid support conjugate.

Also included herein is a method for forming a phosphoprotein comprising a terminal azido modified phosphate that includes contacting a protein with an azido modified phosphate in the presence of an enzyme that will transfer the azido modified phosphate to the protein to form an azido modified phosphoprotein. In some embodiments, the protein has at least one serine, threonine, or tyrosine residue. The invention also includes methods for forming a phosphoprotein conjugate, in which the phosphoprotein conjugate is attached to a reporter molecule, solid support, or carrier molecule, in which the method includes contacting a protein with an azido modified phosphate in the presence of an enzyme that will transfer the azido modified phosphate to the protein to form an azido modified phosphoprotein; and contacting the azido modified phosphoprotein with a reporter molecule, carrier molecule or solid support that comprises a terminal alkyne moiety to form phosphoprotein reporter molecule, carrier molecule or solid support conjugate.

The methods described herein can also be used to label proteins which have been modified with lipids by post-translational lipoylation including, but not limited to, palmitoylation and myristolation. In such post-translational modifications azide-containing lipids, alkyne-containing lipids or phosphine-containing lipids are used to transfer azide moieties, alkyne moieties or phosphine moieties to proteins, whereupon such moieties are used to label the modified protein with a reporter molecule, carrier molecule and/or solid substrate using the methods described herein. An example of such labeling of proteins is given in Example 32 and Example 33.

The methods described herein can be used to label proteins which have been modified with isoprenoid groups by post-translational isoprenylation including, but not limited to, farnesylation and geranylgeranylation. In such post-translational modifications azide-containing isoprenoids, alkyne-containing isoprenoids or phosphine-containing isoprenoids are used to transfer azide moieties, alkyne moieties or phosphine moieties to proteins, whereupon such moieties are used to label the modified protein with a reporter molecule, carrier molecule and/or solid substrate using the methods described herein. An example of such labeling of proteins is given in Example 31.

Chemical Modification of Biomolecules Containing Azide, Alkyne or Phosphine Moieties Biomolecules that can be chemically modified using the methods described herein include, but are not limited to, proteins, peptides, amino acids, glycoproteins, nucleic acids, nucleotides, nucleosides, oligonucleotides, sugars, oligosaccharides, lipids, hormones, proteoglycans, carbohydrates, polypeptides, polynucleotides and polysaccharides. Such biomolecules can contain azide moieties, alkyne moieties or phosphine moieties that are incorporated into biomolecules using post-translational modifications via cellular biosynthetic pathways (metabolic labeling) or enzymatic labeling as described herein. Alternatively, azide moieties, alkyne moieties or phosphine moieties can be incorporated into biomolecules using chemical synthetic procedures as described herein. These azide moieties, alkyne moieties and phosphine moieties are non-native, non-perturbing bioorthogonol chemical moieties that possess unique chemical functionality that can be modified through highly selective reactions. Such reactions used in the methods described herein, wherein the chemical modification of biomolecules that contain azide moieties or alkyne moieties utilize Copper (I)-catalyzed Azide-Alkyne Cycloaddition, also referred to herein as "click" chemistry, the chemical modification of biomolecules that contain azide moieties or phosphine moieties utilize Staudinger ligation, and the chemical modification of biomolecules that contain activated-alkyne moieties or activated-alkyne reactive moieties.

In certain embodiments, the biomolecules used in the methods and compositions described herein can be labeled chemically, enzymatically (for example, by enzymatic in vitro incorporation into the biomolecule of a moiety that includes an azido group or terminal alkyne), or by supplying cells with alkyne or azido-containing molecular precursors (e.g., amino acids or sugars) that can be incorporated into biomolecules in vivo. Such methods are described herein.

"Click" Chemistry

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as "click" chemistry, is a variant of the Huisgen 1,3-dipolar cycloaddition wherein organic azides and terminal alkynes react to give 1,4-regioisomers of 1,2,3-triazoles. Examples of "click" chemistry reactions are described by Sharpless et al. (U.S. Patent Application Publication No. 20050222427, published Oct. 6, 2005, PCT/US03/17311; Lewis W G, et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds. As described herein, "click" chemistry is used in the methods for labeling biomolecules.

The copper used as a catalyst for the "click" chemistry reaction used in the methods described herein to conjugate a label to a biomolecule is in the Cu (I) reduction state. The sources of copper(I) used in such copper(I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent. In certain embodiments, copper can be provided in the Cu (II) reduction state (for example, as a salt, such as but not limited to $Cu(NO_3)_2$ $Cu(OAc)_2$ or $CuSO_4$), in the presence of a reducing agent wherein Cu(I) is formed in situ by the reduction of Cu(II). Such reducing agents include, but are not limited to, ascorbate, Tris(2-Carboxyethyl) Phosphine (TCEP), 2,4,6-trichlorophenol (TCP), NADH, NADPH, thiosulfate, metallic copper, quinone, hydroquinone, vitamin $K_1$, glutathione, cysteine, 2-mercaptoethanol, dithiothreitol, $Fe^{2+}$, $Co^{2+}$, or an applied electric potential. In other embodiments, the reducing agents include metals selected from Al, Be, Co, Cr, Fe, Mg, Mn, Ni, Zn, Au, Ag, Hg, Cd, Zr, Ru, Fe, Co, Pt, Pd, Ni, Rh, and W.

The copper(I)-catalyzed azide-alkyne cycloadditions for labeling biomolecules can be performed in water and a variety of solvents, including mixtures of water and a variety of (partially) miscible organic solvents including alcohols, dimethyl sulfoxide (DMSO), dimethyl formamide (DMF), tert-butanol (tBuOH) and acetone.

Without limitation to any particular mechanism, copper in the Cu (I) state is a preferred catalyst for the copper(I)-catalyzed azide-alkyne cycloadditions, or "click" chemistry reactions, used in the methods described herein. Certain metal ions are unstable in aqueous solvents, by way of example Cu(I), therefore stabilizing ligands/chelators can be used to improve the reaction. In certain embodiments at least one copper chelator is used in the methods described herein, wherein such chelators binds copper in the Cu (I) state. In certain embodiments at least one copper chelator is used in the methods described herein, wherein such chelators binds copper in the Cu (II) state. In certain embodiments, the copper (I) chelator is a 1,10 phenanthroline-containing copper (I) chelator. Non-limiting examples of such phenanthroline-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). Other chelators used in such methods include, but are not limited to, N-(2-acetamido) iminodiacetic acid (ADA), pyridine-2,6-dicarboxylic acid (PDA), S-carboxymethyl-L-cysteine (SCMC), trientine, tetra-ethylenepolyamine (TEPA), N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or a derivative thereof. Most metal chelators, a wide variety of which are known in the chemical, biochemical, and medical arts, are known to chelate several metals, and thus metal chelators in general can be tested for their function in 1,3 cycloaddition reactions catalyzed by copper. In certain embodiments, histidine is used as a chelator, while in other embodiments glutathione is used as a chelator and a reducing agent.

The concentration of the reducing agents used in the "click" chemistry reaction described herein can be in the micromolar to millimolar range. In certain embodiments the concentration of the reducing agent is from about 100 micromolar to about 100 millimolar. In other embodiments the concentration of the reducing agent is from about 10 micromolar to about 10 millimolar. In other embodiments the concentration of the reducing agent is from about 1 micromolar to about 1 millimolar.

In certain embodiments, the methods describe herein for labeling biomolecules using "click" chemistry, at least one copper chelator is added after copper(II) used in the reaction has been contacted with a reducing agent. In other embodiments, at least one copper chelator can be added immediately after contacting copper(II) with a reducing agent. In other embodiments, the copper chelator(s) is added between about five seconds and about twenty-four hours after copper (II) and a reducing agent have been combined in a reaction mixture. In other embodiments, at least one copper chelator can be added any time to a reaction mixture that includes copper(II) and a reducing agent, such as, by way of example only, immediately after contacting copper(II) and a reducing agent, or within about five minutes of contacting copper(II) and a reducing agent in the reaction mixture. In some embodiments, at least one copper chelator can be added between about five seconds and about one hour, between about one minute and about thirty minutes, between about five minutes and about one hour, between about thirty minutes and about two hours, between about one hour and about twenty-four hours, between about one hour and about five hours, between about two hours and about eight hours, after copper(II) and a reducing agent have been combined for use in a reaction mixture.

In other embodiments, one or more copper chelators can be added more than once to such "click" chemistry reactions. In embodiments in which more than one copper chelators is added to a reaction, two or more of the copper chelators can bind copper in the Cu (I) state or, one or more of the copper chelators can bind copper in the Cu (I) state and one or more additional chelators can bind copper in the Cu (II) state. In certain embodiments, one or more copper chelators can be added after the initial addition of a copper chelator to the "click" chemistry reaction. In certain embodiments, the one or more copper chelators added after the initial addition of a copper chelator to the reaction can be the same or different from a copper chelator added at an earlier time to the reaction.

Figure 5:
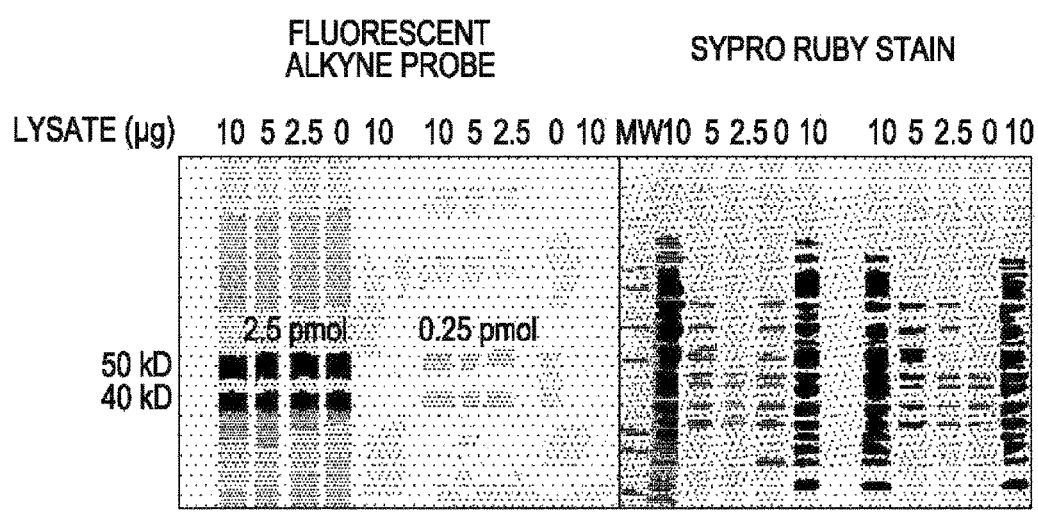
FIG. 5: Shows Labeling Efficiency of 40 and 50 kd Azide-Labeled Model Proteins is Unchanged in Complex Protein Extracts.

The concentration of a copper chelator used in the "click" chemistry reaction described herein can be determined and optimized using methods well known in the art, including those disclosed herein using "click" chemistry to label biomolecules followed by detecting such labeled biomolecules to determine the efficiency of the labeling reaction and the integrity of the labeled biomolecule(s) (see FIG. 5). In certain embodiments, the chelator concentrations used in the methods described herein is in the micromolar to millimolar range, by way of example only, from 1 micromolar to 100 millimolar. In certain embodiments the chelator concentration is from about 10 micromolar to about 10 millimolar. In other embodiments the chelator concentration is from about 50 micromolar to about 10 millimolar. In other embodiments the chelator, can be provided in a solution that includes a water miscible solvent such as, alcohols, dimethyl sulfoxide (DMSO), dimethyl formamide (DMF), tert-butanol (tBuOH) and acetone. In other embodiments the chelator, can be provided in a solution that includes a solvent such as, for example, dimethyl sulfoxide (DMSO) or dimethylformamide (DMF).

In certain embodiments of the methods for labeling biomolecule utilizing "click" chemistry described herein, the biomolecule can possess an azide moiety, whereupon the label possesses an alkyne moiety, whereas in other embodiments the biomolecule can possess an alkyne moiety, and the label possesses an azide moiety.

Staudinger Ligation

The Staudinger reaction, which involves reaction between trivalent phosphorous compounds and organic azides (Staudinger et al. Helv. Chim. Acta 1919, 2, 635), has been used for a multitude of applications. (Gololobov et al. Tetrahedron 1980, 37, 437); (Gololobov et al. Tetrahedron 1992, 48, 1353). There are almost no restrictions on the nature of the two reactants. The Staudinger ligation is a modification of the Staudinger reaction in which an electrophilic trap (usually a methyl ester) is placed on a triaryl phosphine. In the Staudinger ligation, the aza-ylide intermediate rearranges, in aqueous media, to produce an amide linkage and the phosphine oxide, ligating the two molecules together, whereas in the Staudinger reaction the two products are not covalently linked after hydrolysis. Such ligations have been described in U.S. Patent Application No. 20060276658. In certain embodiments, the phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. In certain embodiments, the phosphine can be a di- or triarylphosphine to stabilize the phosphine. The phosphines used in the Staudinger ligation methods described herein to conjugate a label to a biomolecule include, but are not limited to, cyclic or acyclic, halogenated, bisphosphorus, or even polymeric. Similarly, the azides can be alkyl, aryl, acyl or phosphoryl. In certain embodiments, such ligations are carried out under oxygen-free anhydrous conditions. The proteins described herein can be modified using the modified sugars described herein, including but not limited to UDP-GalNAz, using a Staudinger reaction (see, for example, Saxon, E.; Luchansky, S. J.; Hang, H. C.; Yu, C.; Lee, S. C.; Bertozzi, C. R.; J. Am. Chem. Soc.; 2002; 124(50); 14893-14902.).

In certain embodiments of the methods for labeling biomolecule utilizing Staudinger ligation described herein, the biomolecule can possess an azide moiety, whereupon the label possesses a phosphine moiety, whereas in other embodiments the biomolecule can possess a phosphine moiety, and the label possesses an azide moiety.

Activated-Alkyne Chemistry

Azides and alkynes can undergo catalyst free [3+2] cycloaddition by a using the reaction of activated alkynes with azides. Such catalyst free [3+2] cycloaddition can be used in methods described herein to conjugate a label to a biomolecule. Alkynes can be activated by ring strain such as, by way of example only, eight membered ring structures, appending electron-withdrawing groups to such alkyne rings, or alkynes can be activated by the addition of a Lewis acid such as, by way of example only, Au(I) or Au(III).

In certain embodiments of the methods for labeling biomolecule utilizing activated alkynes described herein, the biomolecule can possess an azide moiety, whereupon the label possesses an activated alkyne moiety, whereas in other embodiments the biomolecule can possess an activated alkyne moiety, and the label possesses an azide moiety.

Chemical Modification of Post Translationally Modified Biomolecules

After biomolecules, including but not limited to proteins, have been modified either metabolically or enzymatically with azido moieties, alkyne moieties or phosphine moieties, they can be reacted under appropriate conditions to form conjugates with reporter molecules, solid supports or carrier molecules. In certain embodiments, such proteins used for such conjugations may be present as a cell lysate, as isolated proteins, and/or as purified proteins, separated by gel electrophoresis or on a solid or semi-solid matrix. In certain embodiments, the biomolecules are glycoproteins that have been modified, either metabolically or enzymatically, with azide-containing sugars, alkyne-containing sugars or phosphine-containing sugars.

In the methods and compositions described herein the azide moiety, alkyne moiety or phosphine moiety is used as a reactive functional group on the modified biomolecule wherein an azide reactive moiety on a reporter molecule, a solid support or a carrier molecule, or an alkyne reactive moiety on a reporter molecule, a solid support or a carrier molecule, or a phosphine reactive moiety on a reporter molecule, a solid support or a carrier molecule is reacted with a modified biomolecule to form a covalent conjugate comprising the biomolecule and at least one reporter molecule, at least one solid support and/or at least one carrier molecule. In certain embodiments such biomolecules are proteins, while in other embodiments such proteins are glycoproteins.

In certain embodiments of the methods and compositions described herein, a glycoprotein containing an azide moiety can be selectively labeled with a reporter molecule, a solid support and/or a carrier molecule that contain azide reactive groups including, but not limited to, a terminal alkyne, an activated alkyne, or a phosphine. In other embodiments, a glycoprotein containing an alkyne moiety can be selectively labeled with a reporter molecule, a solid support and/or a carrier molecule that contain alkyne reactive groups including, but not limited to, an azide moiety. In other embodiments, a glycoprotein containing an activated alkyne moiety can be selectively labeled with a reporter molecule, a solid support and/or a carrier molecule that contain alkyne reactive groups including, but not limited to, an azide moiety.

In certain embodiments, two azide-reactive groups are use to label biomolecules: the first is an alkyne moiety used in a "click" chemistry reaction, and the second is a phosphine, such as a triarylphosphine, used in a Staudinger ligation. In one embodiment, "click" chemistry is utilized to form a conjugate with a glycoprotein containing an azide moiety and a reporter molecule, solid support or carrier molecule, wherein the reporter molecule, solid support and carrier molecule contain an alkyne moiety. In another embodiment, "click" chemistry is utilized to form a conjugate with a glycoprotein containing an alkyne moiety and a reporter molecule, solid support and/or carrier molecule, wherein the reporter molecule, solid support and carrier molecule contain an azide moiety. In another embodiment, a Staudinger ligation is utilized to form a conjugate with a glycoprotein containing an azide moiety and a reporter molecule, solid support and/or carrier molecule, wherein the reporter molecule, solid support and carrier molecule contain an triaryl phosphine moiety. In another embodiment, a Staudinger ligation is utilized to form a conjugate with a glycoprotein containing a triaryl phosphine moiety and a reporter molecule, solid support and/or carrier molecule, wherein the reporter molecule, solid support and carrier molecule contain an azide moiety. The methods described herein are not intended to be limited to these two azide-reactive groups, or chemical reactions, but it is envisioned that any chemical reaction utilizing an azide-reactive group attached to a reporter molecule, solid support or carrier molecule can be used with the azide modified glycoproteins described herein.

Protein can be modified using nucleophilic substitution reactions with amines, carboxylates or sulfhydryl groups which are found more commonly on the surface of proteins. However, the methods described herein utilize cycloaddition reactions, rather than nucleophilic substitution reactions, for selective modifications of proteins. Thus proteins described herein can be modified, with the modified sugars described herein, including but not limited to UDP-GalNAz, with extremely high selectivity. Such reactions can be carried out at room temperature in aqueous conditions with excellent regioselectivity by the addition of catalytic amounts of Cu(I) salts to the reaction mixture. See, e.g., Tomoe, et al., (2002) Org. Chem. 67:3057-3064; and, Rostovtsev, et al., (2002) Angew. Chem. Int. Ed. 41:2596-2599. The resulting five-membered ring resulting from "click" chemistry cycloaddition is not generally reversible in reducing environments and is stable against hydrolysis for extended periods in aqueous environments. Thus, glycoproteins attached to a labeling agent, a detection agent, a reporter molecule, a solid support or a carrier molecule via such five-membered ring are stable in rescuing environments.

The reporter molecules, solid supports and carrier molecules used in the methods and compositions described herein, can contain at least one alkyne moiety or at least one phosphine moiety capable of reacting with an azide moiety. The reporter molecules, solid supports and carrier molecules used in the methods and compositions described herein, can contain at least one azide moiety capable of reacting with an alkyne moiety or a phosphine moiety. The reporter molecules, solid supports and carrier molecules used in the methods and compositions described herein, can contain at least one phosphine moiety capable of reacting with an azide moiety. In certain embodiments, the phosphine moieties of the reporter molecules solid supports and carrier molecules described herein are triaryl phosphine moieties.

In certain embodiments, the reporter molecules used in the methods and compositions described herein can include, but are not limited to labels, while the solid supports can include, but are not limited to, solid support resins, microtiter plates and microarray slides. The carrier molecules can include, but are not limited to, affinity tags, nucleotides, oligonucleotides and polymers.

Reporter Molecules

The reporter molecules used in the methods and compositions provided herein include any directly or indirectly detectable reporter molecule known by one skilled in the art that can be covalently attached to a modified biomolecule, including a protein such as a glycoprotein. Such modified glycoproteins can be azide modified glycoproteins, alkyne modified glycoproteins or phosphine modified glycoproteins. In certain embodiments, the reporter molecules used in the methods and compositions provided herein include any directly or indirectly detectable reporter molecule known by one skilled in the art that can be covalently attached to an azide modified glycoprotein, an alkyne modified glycoprotein or a phosphine modified glycoprotein.

Reporter molecules used in the methods and compositions described herein can contain, but are not limited to, a chromophore, a fluorophore, a fluorescent protein, a phosphorescent dye, a tandem dye, a particle, a hapten, an enzyme and a radioisotope. In certain embodiments, such reporter molecules include fluorophores, fluorescent proteins, haptens, and enzymes.

A fluorophore used in a reporter molecule in the methods and compositions described herein, can contain one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

A fluorophore used in a reporter molecule in the methods and compositions described herein, is any chemical moiety that exhibits an absorption maximum at wavelengths greater than 280 nm, and retains its spectral properties when covalently attached to a labeling reagent such as, by way of example only, an azide, and alkyne or a phosphine. Fluorophores used as in reporter molecule in the methods and compositions described herein include, without limitation; a pyrene (including any of the corresponding derivative compounds disclosed in U.S. Pat. No. 5,132,432), an anthracene, a naphthalene, an acridine, a stilbene, an indole or benzoindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774, 339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Xanthene type fluorophores used in reporter molecule in the methods and compositions described herein include, but are not limited to, a fluorescein, a rhodol (including any corresponding compounds disclosed in U.S. Pat. Nos. 5,227, 487 and 5,442,045), or a rhodamine (including any corresponding compounds in U.S. Pat. Nos. 5,798,276; 5,846, 737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945, 171). In certain embodiments, the fluorophore is a xanthene that is bound via a linkage that is a single covalent bond at the 9-position of the xanthene. In other embodiments, the xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

In certain embodiments, the fluorophores used in reporter molecules in the methods and compositions described herein include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines.

In other embodiments, the fluorophores used in reporter molecules in the methods and compositions described herein, wherein such fluorophores have been modified with azide moieties or alkyne moieties. When used in "click" chemistry reaction such fluorophores form triazole products which do not requires UV excitation and overcome any quenching effect due to conjugation of azido or alkyne groups to the fluorescent π-system.

The choice of the fluorophore attached to the labeling reagent will determine the absorption and fluorescence emission properties of the labeling reagent, modified glycoprotein and immuno-labeled complex. Physical properties of a fluorophore label that can be used for detection of modified glycoproteins and an immuno-labeled complex include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp).

Many of fluorophores can also function as chromophores and thus the described fluorophores are also chromophores used in reporter molecules in the methods and compositions described herein.

In addition to fluorophores, enzymes also find use as labels for the detection reagents/reporter molecules used in the methods and compositions described herein. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art, many of which are described in the MOLECULAR PROBES HANDBOOK, supra.

In certain embodiments, colorimetric or fluorogenic substrate and enzyme combination use oxidoreductases such as, by way of example only, horseradish peroxidase and a substrate such as, by way of example only, 3,3'-diaminobenzidine (DAB) or 3-amino-9-ethylcarbazole (AEC), which yield a distinguishing color (brown and red, respectively). Other colorimetric oxidoreductase substrates used with the enzymatic reporter molecules described herein include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates used with the enzymatic reporter molecules described herein include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042), Amplex UltraRed and its variants in (WO05042504) and reduced dihydroxanthenes, including dihydrofluoresceins (U.S. Pat. No. 6,162,931) and dihydrorhodamines including dihydrorhodamine 123. Peroxidase substrates can be used with the enzymatic reporter molecules described herein. Such peroxide substrates include, but are not limited to, tyramides (U.S. Pat. Nos. 5,196,306; 5,583,001 and 5,731,158) which represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

In other embodiments the colorimetric (and in some cases fluorogenic) substrates and enzymes combination used in reporter molecules described herein include a phosphatase enzyme such as, by way of example only, an acid phosphatase, an alkaline phosphatase or a recombinant version of such a phosphatase. A colorimetric substrate used in combination with such phosphatases include, but are not limited to, 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl)phosphate (DDAO phosphate), or ELF 97, ELF 39 or related phosphates (U.S. Pat. Nos. 5,316,906 and 5,443,986).

Other enzymes used in reporter molecules described herein include glycosidases, including, but not limited to, beta-galactosidase, beta-glucuronidase and beta-glucosidase. The colorimetric substrates used with such enzymes include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes used in reporter molecules described herein include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence can also be used in reporter molecules described herein. Such enzymes include, but are not limited to, natural and recombinant forms of luciferases and aequorins. In addition, the chemiluminescence-producing substrates for phosphatases, glycosidases and oxidases such as those containing stable dioxetanes, luminol, isoluminol and acridinium esters an also be used in reporter molecules described herein.

In addition to enzymes, haptens can be used in label/reporter molecules described herein. In certain embodiments, such haptens include hormones, naturally occurring and synthetic drugs, pollutants, allergens, affector molecules, growth factors, chemokines, cytokines, lymphokines, amino acids, peptides, chemical intermediates, nucleotides, biotin and the like. Biotin is useful because it can function in an enzyme system to further amplify the detectable signal, and it can function as a tag to be used in affinity chromatography for isolation purposes. For detection purposes, an enzyme conjugate that has affinity for biotin is used, such as, by way of example only, avidin-Horse Radish Peroxidase (HRP). Subsequently a peroxidase substrate as described herein can be added to produce a detectable signal.

Fluorescent proteins can also be used in label/reporter molecules described herein for use in the methods, compositions and labeling reagents described herein. Non-limiting examples of such fluorescent proteins include green fluorescent protein (GFP) and the phycobiliproteins and the derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. The fluorescent protein and fluorophore function as an energy transfer pair wherein the fluorescent protein emits at the wavelength that the fluorophore absorbs and the fluorophore then emits at a wavelength farther from the fluorescent proteins emission wavelength than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798,276, or the sulfonated cyanine fluorophores disclosed in U.S. Ser. Nos. 09/968/401 and 09/969/853; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

Carrier Molecules: Azide Reactive, Alkyne Reactive and Phosphine Reactive

In the methods and compositions described herein the modified biomolecules can be conjugated to a carrier molecule. In certain embodiments provided herein proteins, such as glycoproteins, are covalently conjugated to a carrier molecule. This includes, but is not limited to, any azide modified glycoprotein disclosed herein and any carrier molecule disclosed herein. In certain embodiments, the glycoproteins contain at least one alkyne moiety or at least one phosphine moiety capable of reacting with a carrier molecule containing an azide moiety. In other embodiments, the glycoproteins contain at least one azide moiety capable of reacting with a carrier molecule containing an alkyne moiety or a phosphine moiety. In other embodiments, the glycoproteins contain at least one phosphine moiety capable of reacting with a carrier molecule containing an azide moiety. In certain embodiments, the phosphine moieties of the glycoproteins and carrier molecules are triaryl phosphine moieties.

A variety of carrier molecules can be used in the methods and compositions described herein, including, but not limited to, antigens, steroids, vitamins, drugs, haptens, metabolites, toxins, environmental pollutants, amino acids, peptides, proteins, nucleic acids, nucleic acid polymers, carbohydrates, lipids, and polymers. In certain embodiments, the carrier molecule contain an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus or combinations thereof.

In other embodiments, the carrier molecule is selected from a hapten, a nucleotide, an oligonucleotide, a nucleic acid polymer, a protein, a peptide or a polysaccharide. In still other embodiments, the carrier molecule is an amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In further embodiments, the carrier molecule is an antibody or fragment thereof, an antigen, an avidin or streptavidin, a biotin, a dextran, an IgG binding protein, a fluorescent protein, agarose, and a non-biological microparticle.

In certain embodiments wherein the carrier molecule is an enzymatic substrate, the enzymatic substrate is selected from an amino acid, a peptide, a sugar, an alcohol, alkanoic acid, 4-guanidinobenzoic acid, a nucleic acid, a lipid, sulfate, phosphate, —$CH_2OCO$-alkyl and combinations thereof. In certain embodiments, such enzyme substrates can be cleaved by enzymes selected from peptidases, phosphatases, glycosidases, dealkylases, esterases, guanidinobenzotases, sulfatases, lipases, peroxidases, histone deacetylases, exonucleases, reductases, endoglycoceramidases and endonucleases.

In other embodiments, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Such peptides include, but are not limited to, neuropeptides, cytokines, toxins, protease substrates, and protein kinase substrates. Other peptides may function as organelle localization peptides, that is, peptides that serve to target the conjugated compound for localization within a particular cellular substructure by cellular transport mechanisms, including, but not limited to, nuclear localization signal sequences. In certain embodiments, the protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. In other embodiments, the protein carrier molecule is an antibody, an antibody fragment, avidin, streptavidin, a toxin, a lectin, or a growth factor. In further embodiments, the carrier molecules contain haptens including, but not limited to, biotin, digoxigenin and fluorophores.

The carrier molecules used in the methods and composition described herein can also contain a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In other embodiments, the nucleotide carrier molecule is a nucleoside or a deoxynucleoside or a dideoxynucleoside, while in other embodiments, the carrier molecule contains a peptide nucleic acid (PNA) sequence or a locked nucleic acid (LNA) sequence. In certain embodiments, the nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

The carrier molecules used in the methods and composition described herein can also contain a carbohydrate or polyol, including a polysaccharide, such as dextran, FICOLL, heparin, glycogen, amylopectin, mannan, inulin, starch, agarose and cellulose, or a polymer such as a poly(ethylene glycol). In certain embodiments, the polysaccharide carrier molecule includes dextran, agarose or FICOLL.

The carrier molecules used in the methods and composition described herein can also include a lipid including, but not limited to, glycolipids, phospholipids, and sphingolipids. In certain embodiments, such lipids contain 6-25 carbons. In other embodiments, the carrier molecules include a lipid vesicle, such as a liposome, or is a lipoprotein (see below). Some lipophilic substituents are useful for facilitating transport of the conjugated dye into cells or cellular organelles. In certain embodiments, the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

The carrier molecules used in the methods and composition described herein can also be a cell, cellular systems, cellular fragment, or subcellular particles, including virus particles, bacterial particles, virus components, biological cells (such as animal cells, plant cells, bacteria, or yeast), or cellular components. Non-limiting examples of such cellular components that are useful as carrier molecules in the methods and composition described herein include lysosomes, endosomes, cytoplasm, nuclei, histones, mitochondria, Golgi apparatus, endoplasmic reticulum and vacuoles.

The carrier molecules used in the methods and composition described herein can also non-covalently associates with organic or inorganic materials.

The carrier molecules used in the methods and composition described herein can also include a specific binding pair member wherein the glycoproteins described herein can be conjugated to a specific binding pair member and used in the formation of a bound pair. In certain embodiments, the presence of a labeled specific binding pair member indicates the location of the complementary member of that specific binding pair; each specific binding pair member having an area on the surface or in a cavity which specifically binds to, and is complementary with, a particular spatial and polar organization of the other. In certain embodiments, the dye compounds (fluorophores or chromophores) described herein function as a reporter molecule for the specific binding pair. Exemplary binding pairs are set forth in Table 2.

TABLE 2

Representative Specific Binding Pairs

| antigen | antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization In a particular aspect the carrier molecule, used in the methods and compositions described herein, is an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. In one aspect the carrier molecule is a Fab fragment specific to the Fc portion of the target-binding antibody or to an isotype of the Fc portion of the target-binding antibody (U.S. Ser. No. 10/118, 204). The monovalent Fab fragments are typically produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$.

In alternative embodiments, a non-antibody protein or peptide such as protein G, or other suitable proteins, can be used alone or coupled with albumin. Preferred albumins include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are conjugated to a reactive moiety in the same manner as the other carrier molecules described.

In another aspect, the carrier molecules, used in the methods and compositions described herein, can be whole intact antibodies. Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds).

When IgG is treated with the enzyme papain a monovalent antigen-binding fragment can be isolated, referred herein to as a Fab fragment. When IgG is treated with pepsin (another proteolytic enzyme), a larger fragment is produced, $F(ab')_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define the Fab', $F(ab')_2$ and Fab portions of the antibody. It is well known in the art to treat antibody molecules with pepsin and papain in order to produce antibody fragments (Gorevic et al., Methods of Enzyol., 116:3 (1985)).

The monovalent Fab fragments used as carrier molecules in the methods and compositions described herein are produced from either murine monoclonal antibodies or polyclonal antibodies generated in a variety of animals that have been immunized with a foreign antibody or fragment thereof (U.S. Pat. No. 4,196,265 discloses a method of producing monoclonal antibodies). Typically, secondary antibodies are derived from a polyclonal antibody that has been produced in a rabbit or goat but any animal known to one skilled in the art to produce polyclonal antibodies can be used to generate anti-species antibodies. The term "primary antibody" describes an antibody that binds directly to the antigen as opposed to a "secondary antibody" that binds to a region of the primary antibody. Monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art.

In one aspect the antibodies used as carrier molecules in the methods and compositions described herein are generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments.

Solid Supports: Azide Reactive, Alkyne Reactive or Phosphine Reactive

In an aspect of the methods and composition described herein, the modified biomolecules can be covalently conjugated to a solid support. In certain embodiments provided herein proteins, such as glycoproteins, are covalently conjugated to a solid support. This includes, but is not limited to, any azide modified glycoprotein disclosed herein and any solid support disclosed herein. In certain embodiments, the glycoproteins contain at least one alkyne moiety or at least one phosphine moiety capable of reacting with a solid support containing an azide moiety. In other embodiments, the glycoproteins contain at least one azide moiety capable of reacting with a solid support containing an alkyne moiety or a phosphine moiety. In other embodiments, the glycoproteins contain at least one phosphine moiety capable of reacting with a solid support containing an azide moiety. In certain embodiments, the phosphine moieties of the glycoproteins and solid supports are triaryl phosphine moieties.

A variety of solid supports can be used in the methods and compositions described herein. Such solid supports are not limited to a specific type of support, and therefore a large number of supports are available and are known to one of ordinary skill in the art. Such solid supports include, but are not limited to, solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. Other non-limiting examples of solid supports used in the methods and compositions described herein include silica gels, polymeric membranes, particles, derivatized plastic films, derivatized glass, derivatized silica, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In certain embodiments, the solid supports used in the methods and compositions described herein are substantially insoluble in liquid phases.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the azide-containing glycoproteins described herein. In other embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the alkyne-containing glycoproteins described herein. In still other embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the phosphine-containing glycoproteins described herein. In other embodiments, the solid supports include azide, alkyne or phosphine functional groups to covalently attach such modified glycoproteins.

A suitable solid phase support used in the methods and compositions described herein, can be selected on the basis of desired end use and suitability for various synthetic protocols. By way of example only, where amide bond formation is desirable to attach the modified glycoproteins described herein to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories). In certain embodiments, the modified glycoproteins described herein are deposited onto a solid support in an array format. In certain embodiments, such deposition is accomplished by direct surface contact between the support surface and a delivery mechanism, such as a pin or a capillary, or by ink jet technologies which utilize piezoelectric and other forms of propulsion to transfer liquids from miniature nozzles to solid surfaces. In the case of contact printing, robotic control systems and multiplexed printheads allow automated microarray fabrication. For contactless deposition by piezoelectric propulsion technologies, robotic systems also allow for automatic microarray fabrication using either continuous and drop-on-demand devices.

Compositions

In one aspect, the modified biomolecules, reporter molecules and carrier molecules provided herein can be used to form a first composition that includes a modified biomolecule, a first reporter molecule, and a carrier molecule. In another embodiment, a second biomolecule that includes a first composition in combination with a second conjugate, wherein the second conjugate comprises a carrier molecule or solid support that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such compositions, the carrier molecule (or solid support) of the conjugates in the second composition may be the same or a different molecule. The discussion herein pertaining to the identity of various carrier molecules is generally applicable to this embodiment as well as other embodiments.

In certain embodiments, modified proteins, such as glycoproteins, reporter molecules and carrier molecules provided herein can be used to form a first composition that includes a modified glycoprotein, a first reporter molecule, and a carrier molecule. In another embodiment, a second glycoprotein that includes a first composition in combination with a second conjugate, wherein the second conjugate comprises a carrier molecule or solid support that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such compositions, the carrier molecule (or solid support) of the conjugates in the second composition may be the same or a different molecule. The discussion herein pertaining to the identity of various carrier molecules is generally applicable to this embodiment as well as other embodiments.

In another aspect, the modified biomolecules, reporter molecules and solid supports provided herein can be used to form a first composition that comprises a modified biomolecule, a first reporter molecule, and a solid support. In another embodiment, a second composition that includes a first composition in combination with a second conjugate. The second conjugate comprises a solid support or carrier molecule (described herein) that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such composition, the solid support (or carrier molecule) of the conjugates in the second composition may be the same or a different molecule. The discussion herein pertaining to the identity of various solid supports is generally applicable to this embodiment of the invention as well as other embodiments.

In another aspect, the modified proteins, such as glycoproteins, reporter molecules and solid supports provided herein can be used to form a first composition that comprises a modified glycoprotein, a first reporter molecule, and a solid support. In another embodiment, a second composition that includes a first composition in combination with a second conjugate. The second conjugate comprises a solid support or carrier molecule (described herein) that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such composition, the solid support (or carrier molecule) of the conjugates in the second composition may be the same or a different molecule. The discussion herein pertaining to the identity of various solid supports is generally applicable to this embodiment of the invention as well as other embodiments.

Methods for Labeling Modified Biomolecules in Solution

Methods for forming modified biomolecule-reporter molecule conjugates are described herein. In certain embodiments the biomolecules are glycoproteins that have been azido modified metabolically, enzymatically or chemically using the methods described herein. In one aspect the modified biomoelcule-reporter molecule conjugates are formed in solution and then separated using methods known in the art. In certain embodiments, the biolmolecule labeled with the reporter molecule is a modified glycoprotein. In other embodiments, the biolmolecule labeled with the reporter molecule is an azido modified glycoprotein, alkyne modified glycoprotein, or phosphine modified glycoprotein.

Described herein are novel methods for forming conjugates in solution with azido modified biomolecules and a reporter molecule comprising a terminal alkyne under "click" chemistry conditions. In other embodiments, "click" chemistry is used to form conjugates with alkyne modified biomolecules and a reporter molecule comprising an azide. In other embodiments, Staudinger ligation is used to form conjugates with azide modified biomolecules and a reporter molecule comprising a phosphine, while other embodiments use Staudinger ligation to form conjugates with phosphine modified biomolecules and a reporter molecule comprising an azide. Still other embodiments use activated alkyne modified biomolecules to form conjugates with reporter molecules comprising azides, or azide modified biomolecules forming conjugates with activated alkyne containing reporter molecules.

It was unexpectedly found that by adding a copper chelator to the "click" chemistry conjugation reaction the labeling efficiency and resolution after gel electrophoresis improved as compared to those reactions without the addition of a copper chelator. In certain embodiments, the methods of labeling biomolecules using "click" chemistry, involve a biomolecule that includes an azido group and a label that includes a terminal alkyne that are reacted in a mixture that includes copper (II), a reducing agent, and at least one copper (I) chelator, thereby producing a labeled biomolecule. In certain embodiments, the biomolecules labeled in such methods can be polysaccharides, nucleic acids, proteins, or peptides. In certain embodiments, the biomolecules used in the labeling methods described herein are glycoproteins In certain embodiments, the biomolecules used in the labeling methods described herein are proteins, such as but not limited to glycoproteins. The labeling methods used to label proteins, including glycoproteins, include "click" chemistry or Staudinger ligation. In certain embodiments, the labeling of glycoproteins occurs by "click" chemistry in which a glycoprotein that includes an azido group and a label that comprises a terminal alkyne react in a mixture that includes copper (II), a reducing agent, and at least one copper chelator to produce a labeled glycoprotein. In certain embodiments, the labeling of glycoproteins occurs by "click" chemistry in which a glycoprotein that includes an alkyne group and a label that comprises an azide react in a mixture that includes copper (II), a reducing agent, and at least one copper chelator to produce a labeled glycoprotein.

In other aspects provided herein, the methods of labeling biomolecules using "click" chemistry, wherein a biomolecule that includes an azido group and a label that comprises a terminal alkyne are reacted in a mixture that includes copper (II), a reducing agent, and at least one copper (I) chelator to produce a labeled biomolecule, results in the preservation of the structural integrity of the labeled biomolecule. In other embodiments, the biomolecules labeled in such cycloaddition reactions can be polysaccharides, nucleic acids, proteins, or peptides. In certain embodiments, the biomolecules used in such methods are proteins, such as but not limited to glycoproteins. In such methods a glycoprotein that includes an azido group and a label that comprises a terminal alkyne are reacted in a mixture that includes copper (II), a reducing agent, and at least one copper (I) chelator to produce a labeled glycoprotein, and results in the preservation of the structural integrity of the labeled glycoprotein, wherein the structural integrity of the glycoprotein after labeling is not reduced. As described herein, the glycoproteins can be derivatized, for example, by in vivo incorporation of azido sugars or by in vitro enzymatic addition of azido sugars. In other embodiments, methods of labeling glycoproteins wherein the structural integrity of the glycoprotein after labeling is not reduced includes "click" chemistry in which a glycoprotein that includes a terminal alkyne and a label that comprises an azido group are reacted in a mixture that includes copper (II), a reducing agent, and at least one copper chelator to produce a labeled glycoprotein.

The methods for labeling biomolecules that comprise an azido group using "click" chemistry described herein can also be used for biomolecules that comprise a terminal alkyne, wherein the label to be reacted with the biomolecule comprises an azido group. The methods for labeling and detecting biomolecules that comprise an azido group using "click" chemistry described herein can also be used for biomolecules that comprise a terminal alkyne, wherein the label to be reacted with the biomolecule comprises an azido group. In one embodiment, is a method using the "click" chemistry reaction described herein to form biomolecule-reporter molecule conjugates in which the reaction mixture includes a reporter molecule with an azide moiety, an alkyne modified biomolecule, copper (II) ions, at least one reducing agent and a copper chelator. In certain embodiments, such alkyne modified biomolecule are alkyne modified glycoproteins and such reporter molecule with an azide moiety are any reporter molecule described herein. In other embodiments, such alkyne modified biomolecule are alkyne modified glycoproteins and such reporter molecule with an azide moiety are any fluorophore based reporter molecule described herein.

Other methods provided herein, are methods for labeling and detecting separated proteins, including but not limited to glycoproteins, using the "click" chemistry cycloaddition reaction described herein. The method includes: combining in a reaction mixture a biomolecule that comprises an azido group, a label that includes a terminal alkyne group, copper (II), a reducing agent, and a copper chelator; incubating the reaction mixture under conditions that promote chemical conjugation of the label to the biomolecule, separating the biomolecule using one or more biochemical or biophysical separation techniques, and detecting the biomolecule. In other embodiments, the method includes: combining in a reaction mixture a biomolecule that comprises an alkyne group, a label that includes an azide group, copper (II), a reducing agent, and a copper chelator; incubating the reaction mixture under conditions that promote chemical conjugation of the label to the biomolecule, separating the biomolecule using one or more biochemical or biophysical separation techniques, and detecting the biomolecule.

In another embodiment is a method for detecting modified biomolecules, wherein the method includes the steps of:
  a) forming an azide-alkyne cycloaddition reaction mixture that includes a reporter molecule having a terminal alkyne moiety, an azido modified biomoelcule, copper (II) ions, at least one reducing agent and a copper chelator;
  b) incubating the azide-alkyne cycloaddition reaction mixture for a sufficient amount of time to form a biomoelcule-reporter molecule conjugate;
  c) separating the biomoelcule-reporter molecule conjugate by size and/or weight of the biomolecule-reporter molecule conjugate to form a separated biomolecule-reporter molecule conjugate;
  d) illuminating the separated biomoelcule-reporter molecule conjugate with an appropriate wavelength to form an illuminated biomolecule-reporter molecule conjugate, and
  e) observing the illuminated biomolecule-reporter molecule conjugate wherein the biomolecules is detected.

In another embodiment is a method for detecting modified glycoproteins, wherein the method includes the steps of:
  a) forming an azide-alkyne cycloaddition reaction mixture that includes a reporter molecule having a terminal alkyne moiety, an azido modified glycoprotein, copper (II) ions, at least one reducing agent and a copper chelator;
  b) incubating the azide-alkyne cycloaddition reaction mixture for a sufficient amount of time to form a glycoprotein-reporter molecule conjugate;
  c) separating the glycoprotein-reporter molecule conjugate by size and/or weight of the glycoprotein-reporter molecule conjugate to form a separated glycoprotein-reporter molecule conjugate;
  d) illuminating the separated glycoprotein-reporter molecule conjugate with an appropriate wavelength to form an illuminated glycoprotein-reporter molecule conjugate, and
  e) observing the illuminated glycoprotein-reporter molecule conjugate wherein the glycoprotein is detected.

In another embodiment is a method for detecting modified biomolecules, wherein the method includes the steps of:

a) forming an azide-alkyne cycloaddition reaction mixture that includes a reporter molecule having an azide moiety, an alkyne modified biomoelcule, copper(II) ions, at least one reducing agent and a copper chelator;

b) incubating the azide-alkyne cycloaddition reaction mixture for a sufficient amount of time to form a biomoelcule-reporter molecule conjugate;

c) separating the biomoelcule-reporter molecule conjugate by size and/or weight of the biomolecule-reporter molecule conjugate to form a separated biomoelcule-reporter molecule conjugate;

d) illuminating the separated biomoelcule-reporter molecule conjugate with an appropriate wavelength to form an illuminated biomolecule-reporter molecule conjugate, and e) observing the illuminated biomolecule-reporter molecule conjugate wherein the biomolecule is detected.

In another embodiment is a method for detecting modified glycoproteins, wherein the method includes the steps of:

a) forming an azide-alkyne cycloaddition reaction mixture that includes a reporter molecule having an azide moiety, an alkyne modified glycoprotein, copper(II) ions, at least one reducing agent and a copper chelator;

b) incubating the azide-alkyne cycloaddition reaction mixture for a sufficient amount of time to form a glycoprotein-reporter molecule conjugate;

c) separating the glycoprotein-reporter molecule conjugate by size and/or weight of the glycoprotein-reporter molecule conjugate to form a separated glycoprotein-reporter molecule conjugate;

d) illuminating the separated glycoprotein-reporter molecule conjugate with an appropriate wavelength to form an illuminated glycoprotein-reporter molecule conjugate, and e) observing the illuminated glycoprotein-reporter molecule conjugate wherein the glycoprotein is detected.

In addition such "click" chemistry reaction mixtures can include, without limitation, one or more buffers, polymers, salts, detergents, or solubilizing agents. The reaction can be performed under anaerobic conditions, such as under nitrogen or argon gas, and can be performed for any feasible length of time, such as, for example, from ten minutes to six hours, from about twenty minutes to about three hours, or from about thirty minutes to about two hours. The reaction can be performed at a wide range of temperatures, for example ranging from about 4 degrees Celsius to about 50 degrees Celsius, and is preferably performed at temperatures between about 10 degrees and about 40 degrees, and typically between about 15 degrees and about 30 degrees.

Separation and Detection

Another aspect provided herein are methods directed toward detecting modified biomolecules after the modified biomolecules have been labeled, using "click" chemistry reactions, Staudinger ligation or activated alkyne reactions, and separated using, for example, chromatographic methods or electrophoresis methods such as, but not limited to, gel electrophoresis. The modified biomolecules that can be labeled, separated and detected using the methods described herein include, but are not limited to, polysaccharides, nucleic acids, proteins, or peptides and glycoproteins. In certain embodiments such biomolecules have been modified using the methods described herein. The separation methods used to separate such modified biomolecules includes, but are not limited to, thin layer or column chromatography (including, for example, size exclusion, ion exchange, or affinity chromatography) or isoelectric focusing, gel electrophoresis, capillary electrophoresis, capillary gel electrophoresis, and slab gel electrophoresis. Gel electrophoresis can be denaturing or nondenaturing gel electrophoresis, and can include denaturing gel electrophoresis followed by nondenaturing gel electrophoresis (e.g., "2D" gels). In certain embodiments, the modified biolmolecules are used to form conjugates with a reporter molecule, a carrier molecule and/or a solid support prior to separation using the methods described herein. In other embodiments, the modified biolmolecules are used to form conjugates with a reporter molecule, a carrier molecule and/or a solid support after separation using the methods described herein.

In other embodiments, the separation methods used in such separation and detection methods can be any separation methods used for biomolecules, such as, for example, chromatography, capture to solid supports, and electrophoresis. In certain embodiments, gel electrophoresis is used to separate biomolecules, such as but not limited to proteins. Gel electrophoresis is well known in the art, and in the context of the present invention can be denaturing or nondenaturing gel electrophoresis and can be 1D or 2D gel electrophoresis. FIG. 3 shows detection, via 2-D gel electrophoresis, of proteins modified with $Ac_4GlcNAz$ and labeled with a fluorescent alkyne probe using click chemistry.

In certain embodiments of such separation and detection methods, gel electrophoresis is used to separate proteins, including glycoproteins, and the separated proteins are detected in the gel by the attached labels. By way of example only, glycoproteins that have incorporated azido sugars can be labeled in a solution reaction with a terminal alkyne-containing fluorophore, and the proteins can be optionally further purified from the reaction mixture and electrophoresed on a 1D or 2D gel. The proteins can be visualized in the gel using light of the appropriate wavelength to stimulate the fluorophore label.

Gel electrophoresis can use any feasible buffer system described herein including, but not limited to, Tris-acetate, Tris-borate, Tris-glycine, BisTris and Bistris-Tricine. In certain embodiments, the electrophoresis gel used in the methods described herein comprise acrylamide, including by way for example only, acrylamide at a concentration from about 2.5% to about 30%, or from about 5% to about 20%. In certain embodiments, such polyacrylamide electrophoresis gel comprise 1% to 10% crosslinker, including but not limited to, bisacrylamide. In certain embodiments, the electrophoresis gel used in the methods described herein comprises agarose, including by way for example only, agarose at concentration from about 0.1% to about 5%, or from about 0.5% to about 4%, or from about 1% to about 3%. In certain embodiments, the electrophoresis gel used in the methods described herein comprises acrylamide and agarose, including by way for example only, electrophoresis gels comprising from about 2.5% to about 30% acrylamide and from about 0.1% to about 5% agarose, or from about 5% to about 20% acrylamide and from about 0.2% to about 2.5% agarose. In certain embodiments, such polyacrylamide/agarose electrophoresis gel comprise 1% to 10% crosslinker, including but not limited to, bisacrylamide. In certain embodiments, the gels used to separate biomolecules can be gradient gels.

The methods described herein can be used to detect modified biomolecules for "in-gel" detection using slab gel electrophoresis or capillary gel electrophoresis. In certain embodiments such modified biomolecules are glycoproteins. In one aspect, the method includes combining an azido modified biomolecule, a label that includes a terminal alkyne, copper (II), a reducing agent, and a copper (I) chelator in a reaction mixture; incubating the reaction mixture under conditions that promote chemical conjugation of the label to the biomolecule; separating the biomolecule using one or more biochemical separation techniques; and detecting the biomolecule. The label used in such methods can be any label described herein. The copper (I) chelator used in such methods can be any chelator described herein. In certain embodiments, the copper (I) chelator use in such methods is a 1,10 phenanthroline-containing copper (I) chelator. In other embodiments, the copper(I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II).

Without limitation to any specific mechanism, it is known that copper can promote the cleavage of biomolecules such as proteins and nucleic acids. The addition of a copper chelator in such methods reduces the detrimental effects of copper used in the "click" chemistry reactions, and thereby preserves the structural integrity of the biomolecules. Thus, the methods described herein preserve the structural integrity of labeled and detected biomolecules, and thereby provide improved methods of separating and detecting biomolecules labeled using "click" chemistry. In addition, the methods of detecting separated biomolecules using click chemistry, in which the structural integrity of the separated molecules is preserved, improves the detection of such biomolecules.

In another embodiment of "in-gel" detection, the method includes combining an alkyne modified biomolecule that comprises a terminal alkyne, a label that includes an azido group, copper (II), a reducing agent, and a copper (I) chelator in a reaction mixture; incubating the reaction mixture under conditions that promote chemical conjugation of the label to the biomolecule; separating the labeled biomolecule using one or more biochemical separation techniques; and detecting the biomolecule. In these methods, the structural integrity of labeled and detected biomolecules is preserved. The label used in such methods can be any label described herein. The copper (I) chelator used in such methods can be any chelator described herein. In certain embodiments, the copper (I) chelator use in such methods is a 1,10 phenanthroline-containing copper (I) chelator. In other embodiments, the copper(I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II).

Figure 4:
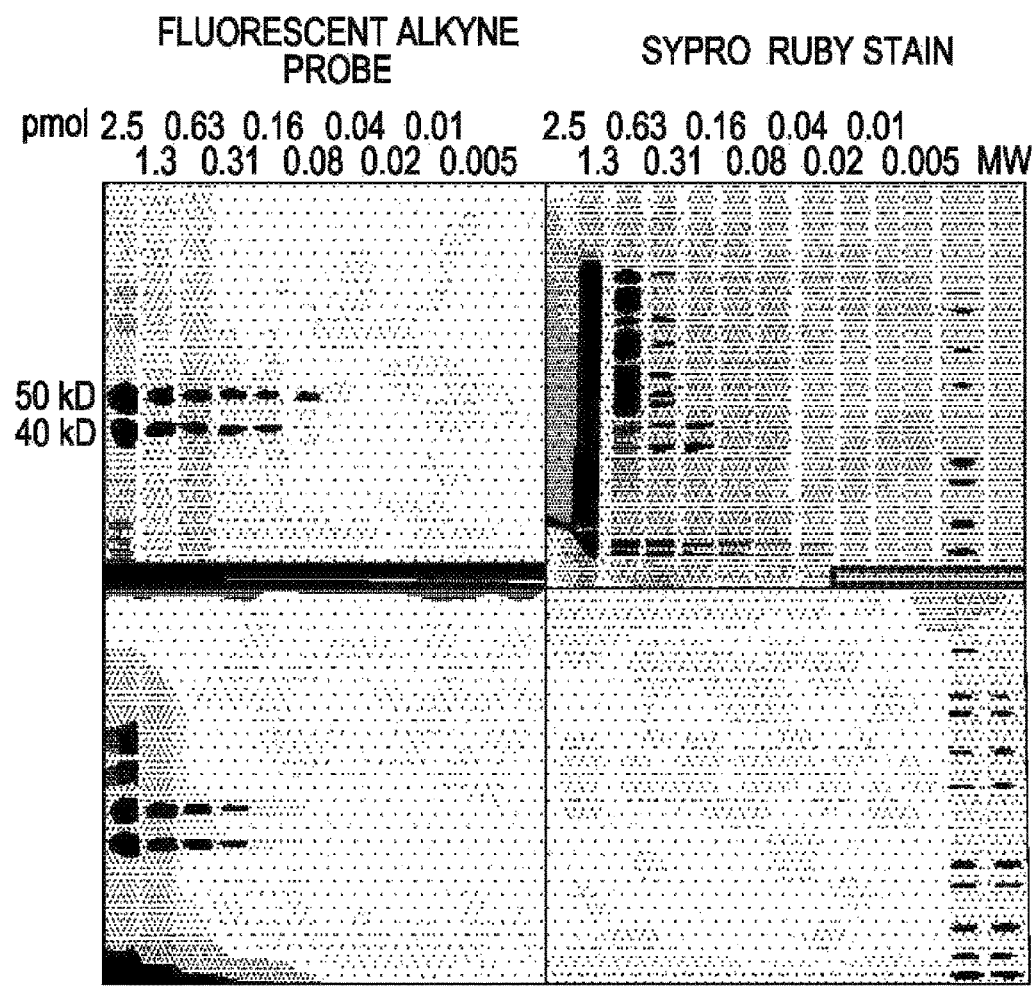
FIG. 4: Shows in gel detection of 40 and 50 kD azide-labeled model proteins, which were first labeled with a fluorescent alkyne tag and then separated on the gel.

In-gel fluorescence detection allows for quantitative differential analysis of protein glycosylation between different biological samples and is amenable to multiplexing with other protein gel stains. In certain embodiments of the methods described herein, utilizing fluorescent- and/or UV-excitable alkyne containing probes, or fluorescent- and/or UV-excitable azide containing probes, allow for the multiplexed detection of glycoproteins, phosphoproteins, and total proteins in the same 1-D or 2-D gels. FIG. 4 shows "in gel" detection of 40 and 50 kD azide-labeled model proteins, which were first labeled with a fluorescent alkyne tag and then separated on the gel.

In certain embodiments, the labels used in such separation and detection methods are any fluorophores described herein which has been derivatized to contain an alkyne, an azide or a phosphine. In certain embodiments, such fluorophores include, but are not limited to, fluorescein, rhodamine, TAMRA, an Alexa dye, a SYPRO dye, or a BODIPY dye.

Figure 9A:
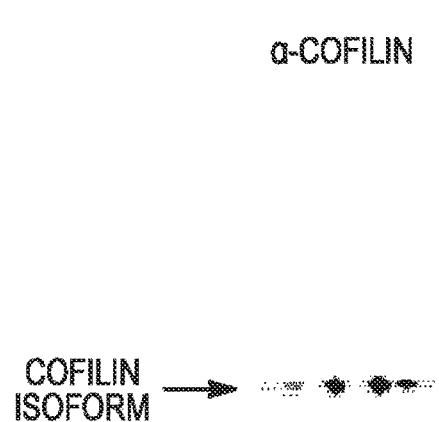
FIG. 9: Shows Multiplexed Western Blot Detection of O-GlcNAc (FIG. 9B) and Cofilin (FIG. 9A).
Figure 9B:
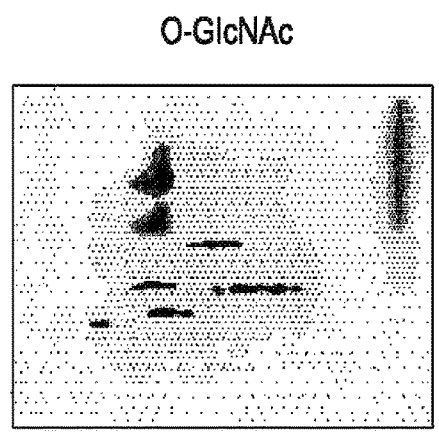

The method described herein can be used for multiplexed detection of biomolecules, such as proteins by labeling the proteins with labels of different specificities. For example, a total proteins stain, such as SYPRO Ruby can be used to stain a gel that includes proteins labeled using a fluorophore with distinct spectral emission using the methods of the present invention. Proteins having other characteristics, such as oxidized proteins or phosphorylated proteins, can be detected in the same gel by use of phosphoprotein specific labels used to stain the gel. FIG. 9 shows multiplexed Western blot detection of O-GlcNAc and Cofilin.

In another aspect, proteins, such as glycoproteins) can be labeled with an azido tag, electrophoresed on gels, and the resulting gels can be incubated with an alkyne tag, such as a fluorescent alkyne tag in the presence of copper (I). Copper (I) can be added in its natural form (e.g. CuBr) or can be produced in situ from copper (II) compounds with the addition of a reducing agent. The reducing agent used in such methods can be any reducing agent described herein, including but not limited to, ascorbate or TCEP. Addition of a chelator that stabilizes copper (I) can enhance the chemical ligation. The fluorescent label used in such methods can be any fluorophore described herein. The copper (I) chelator used in such methods can be any chelator described herein. In certain embodiments, the copper (I) chelator use in such methods is a 1,10 phenanthroline-containing copper (I) chelator. In other embodiments, the copper(I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II). After the ligation step, the gel is washed and the tagged proteins are visualized using standard fluorescence scanning devices.

In other embodiments, proteins, such as glycoproteins, can be labeled with an alkyne tag, electrophoresed on gels, and the resulting gels can be incubated with an azide tag, such as a fluorescent azide tag in the presence of copper (I). Copper (I) can be added in its natural form (e.g. CuBr) or can be produced in situ from copper (II) compounds with the addition of a reducing agent. The reducing agent used in such methods can be any reducing agent described herein, including but not limited to, ascorbate or TCEP. Addition of a chelator that stabilizes copper (I) can enhance the chemical ligation. The fluorescent label used in such methods can be any fluorophore described herein. The copper (I) chelator used in such methods can be any chelator described herein. In certain embodiments, the copper (I) chelator use in such methods is a 1,10 phenanthroline-containing copper (I) chelator. In other embodiments, the copper(I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II). After the ligation step, the gel is washed and the tagged proteins are visualized using standard fluorescence scanning devices.

In further embodiments, proteins, such as glycoproteins, can be labeled with an azide tag, electrophoresed on gels, and the resulting gels can be incubated with a phosphine tag, such as a fluorescent phosphine containing tag, using Staudinger ligation. After the ligation step, the gel is washed and the tagged proteins are visualized using standard fluorescence scanning devices. In such methods the use of copper, which contributes to the degradation of biomolecules such as proteins, can be avoided.

In another aspect, detection of proteins labeled using the methods described herein can be by Western blot, in which biomolecules derivatized to include an azido group are labeled with a detectable label prior to gel electrophoresis and transferred to a blotting membrane. Azido-containing biomolecules can be labeled, for example, with alkyl-biotin, and after electrophoretic separation and transfer to a blotting membrane, can be detected using streptavidin linked to an enzyme that converts a chromogenic substrate. Those skilled in the art will appreciate that any feasible label that is directly detectable or indirectly detectable and can be derivatized to include a terminal alkyne or an azido group can be attached to a biomolecule that includes an azido group or a terminal alkyne and used to detect separated biomolecules, including separated biomolecules transferred to a membrane.

In other embodiments Western blotting analyses reveal glycoprotein subclass detection sensitivities in the low femtomole range and allow for multiplexing with protein-specific antibodies. In certain embodiments, biotin-alkyne probes, or biotin-azide probes, allow for multiplexed Western blot detection of glycoproteins and targeted proteins of interest using monoclonal or polyclonal antibodies. The results achieved with the combined glycoprotein detection strategy described herein, provide selectivity and sensitivity that is currently unachievable with commonly used lectin-based and antibody-based glycoprotein detection technologies.

Figure 8A:
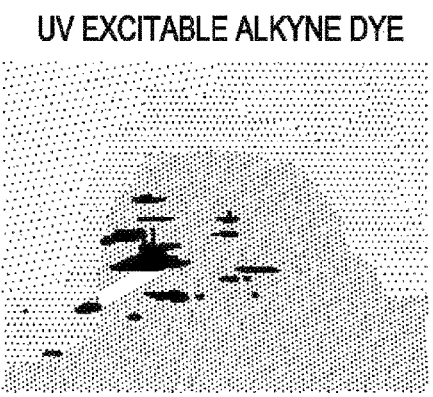
FIG. 8: Shows the Multiplex Detection of O-GlcNAc Proteins (FIG. 8A), Phosphoproteins (FIG. 8B) and Total Proteins (FIG. 8C) in the Same 2-D gel.
Figure 8B:
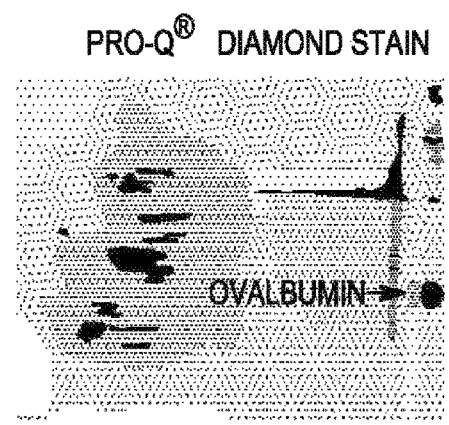
Figure 8C:
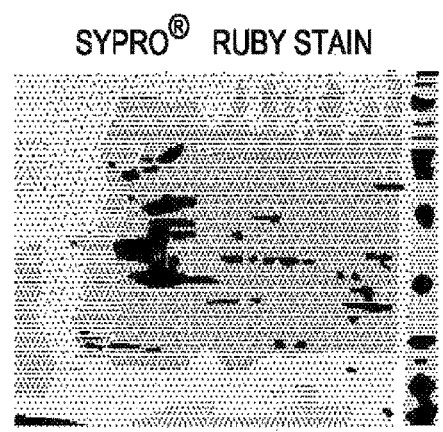
Figure 10A:
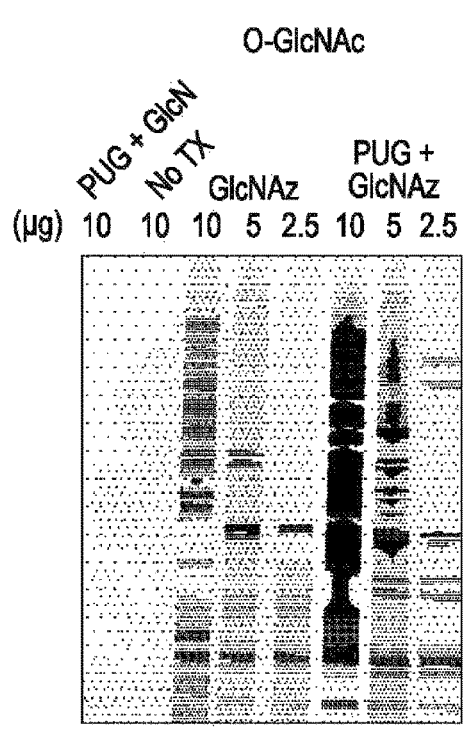
FIGS. 10A and 10B show the Differential Detection of O-GlcNAc Modified Proteins in Control and Inhibitor-Treated Cultured Cell Extracts.
Figure 10B:
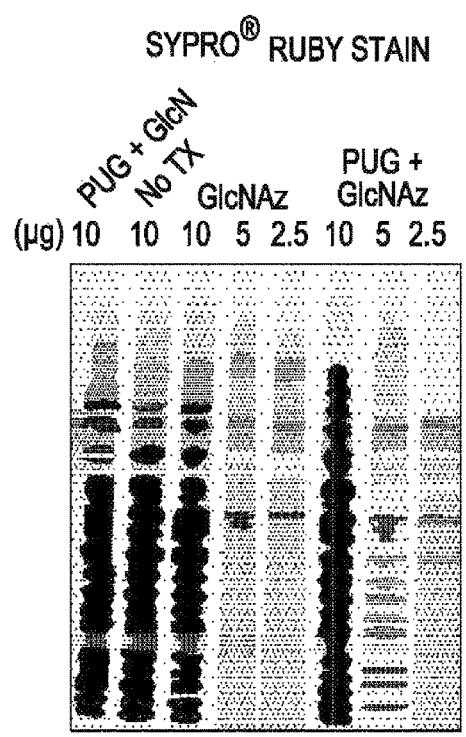

The methods described herein utilizing copper catalyzed cycloaddition chemistry can result in highly sensitive detection of proteins modified with azides or alkynes, as shown by 1-D and 2-D fluorescent gel sensitivities on gel electrophoresis and Western blots (see FIGS. 8-10). In certain embodiments the detection sensitivity is in the low picomole range, while in either embodiments the detection sensitivity is in the mid-to-low femtomole range (see FIGS. 6B1 and 6B2), and the labeling efficiency.

In certain embodiments, a label attached to a biomolecule, such as a protein, using a "click" chemistry reaction with a copper (I) chelator as disclosed herein, can also be used for the separation of biomolecules. By way of example only, affinity chromatography or bead capture techniques can be used to separate biomolecules labeled with biotin or other affinity tags using the methods described herein. The captured molecules can be detected using the affinity tags or by other means, and/or further analyzed for structure or function.

Another aspect of "in gel" detection is the total detection of proteins in electrophoresis gels or Western blot membranes using a "universal click" chemistry in which phenylboronic acid-containing molecules are tethered via a linker to an azide moiety or an alkyne moiety. The phenylboronic acid associates with the cis-diol moieties on glycoproteins which is stable, except under acidic conditions. Such labels can be used to modify glycoproteins after electrophoretic separation with either azide or alkyne moieties which can then be used to add a label via "click" chemistry, Staudinger ligation or activated alkyne chemistry. The gel is then visualized to detect the labeled glycoproteins. In certain embodiments, glycoproteins of interest can be isolated by excising bands of interest after such labeling and treating the gel pieces under acidic conditions to reverse the association of the phenylboronic acid with the cis-diol moieties on glycoproteins, thereby releasing the glycoproteins. The released glycoproteins can then be identified using mass spectrometry.

Methods for Labeling Immobilized Modified Biomolecules

Another aspect provides a method for labeling modified biomolecules that have been immobilized on a solid support. Solid supports used in such methods have been described herein, and can be solid or semi-solid matrix. Such solid supports include, but are not limited to, glass, slides, arrays, silica particles, polymeric particles, microtiter plates and polymeric gels. In this aspect the biomolecules are modified using the methods described herein. In certain aspects it is advantageous to first immobilize the modified biomolecules and then to subsequently form a biomolecule conjugate comprising the biomolecule and a reporter molecule, carrier molecule and the solid support, wherein the reporter molecule, carrier molecule or solid support comprise a reactive group used to form the conjugate. In certain embodiments such reactive groups are alkynes for reacting with azides. In certain embodiments such reactive groups are activated alkynes for reacting with azides. In certain embodiments such reactive groups are phosphines for reacting with azides. In certain embodiments such reactive groups are azides for reacting with alkynes. In certain embodiments, the conjugate is formed under "click" chemistry conditions wherein the reporter molecule, carrier molecule or solid support comprises an alkyne or an azide. In another aspect the conjugate is formed under Staudinger ligation conditions wherein the reporter molecule, carrier molecule or solid support comprises a triaryl phosphine or an azide. In another aspect the conjugate is formed using activated alkynes wherein the reporter molecule, carrier molecule or solid support comprises an activated alkyne or an azide.

In this aspect the biomolecules are metabolically, enzymatically or chemically modified with an azide containing moiety, an alkyne containing moiety or a phosphine containing moiety using the methods described herein. In certain embodiments the modified biomolecule is an azido modified biomolecule, an alkyne modified biomolecule or a phosphine modified biolmolecule. In certain embodiments, the azido modified biomolecule is an azido modified glycoprotein. In certain embodiments, the alkyne modified biomolecule is an alkyne modified glycoprotein. In certain embodiments, the phosphine modified biomolecule is a phosphine modified glycoprotein.

In certain embodiments, it is advantageous to first immobilize the azido modified biomolecules and then to subsequently form the biomolecule conjugate comprising a reporter molecule, carrier molecule or solid support wherein the reporter molecule, carrier molecule or solid support comprise an azide reactive group prior to forming the conjugate. In certain embodiments, the conjugate is formed under "click" chemistry conditions wherein the reporter molecule, carrier molecule or solid support comprises a terminal alkyne. In another aspect the conjugate is formed under Staudinger ligation conditions wherein the reporter molecule, carrier molecule or solid support comprises a triaryl phosphine. In certain embodiments, azido modified glycoproteins are first immobilized onto a solid support, and then subsequently used to form a modified glycoprotein conjugate comprising a reporter molecule, carrier molecule or solid support wherein the reporter molecule, carrier molecule or solid support comprise an azide reactive group prior to forming the conjugate. In certain embodiments, the conjugate is formed under "click" chemistry conditions wherein the reporter molecule, carrier molecule or solid support comprises a terminal alkyne. In another aspect the conjugate is formed under Staudinger ligation conditions wherein the reporter molecule, carrier molecule or solid support comprises a triaryl phosphine.

In another aspect, the modified biomolecule is attached to a solid support using functional groups other than functional groups used in "click" chemistry or Staudinger ligation, whereupon the attached modified biomolecule is used to form a conjugate under "click" chemistry conditions or Staudinger ligation with reporter molecules, carrier molecule or another solid support that have functional groups used in "click" chemistry or Staudinger ligation. By way of example only, the modified biomolecule can be immobilized to a solid support using hydroxyl, carboxyl, amino, thiol, aldehyde, halogen, nitro, cyano, amido, urea, carbonate, carbamate, isocyanate, sulfone, sulfonate, sulfonamide or sulfoxide functional groups.

In this aspect the biomolecules are modified with an azide containing moiety, an alkyne containing moiety or a phosphine containing moiety using the methods described herein. In certain embodiments the modified biomolecule is an azido modified biomolecule, an alkyne modified biomolecule or a phosphine modified biolmolecule. In certain embodiments, the azido modified biomolecule is an azido modified glycoprotein. In certain embodiments, the alkyne modified biomolecule is an alkyne modified glycoprotein. In certain embodiments, the phosphine modified biomolecule is a phosphine modified glycoprotein.

In certain embodiments, the azido modified biomolecule is attached to a solid support using functional groups other than azide reactive functional groups, whereupon the attached azido modified biomolecule is used to form a conjugate under click chemistry conditions wherein the reporter molecule, carrier molecule or another solid support comprises a terminal alkyne. In another embodiment the azido modified biomolecule is attached to a solid support using functional groups other than azide reactive functional groups, whereupon the attached azido modified biomolecule is used to form a conjugate under Staudinger ligation conditions wherein the reporter molecule, carrier molecule or other solid support comprises a triaryle phosphine. In certain embodiments, an azido modified glycoprotein is attached to a solid support using functional groups other than azide reactive functional groups, whereupon the attached azido modified glycoprotein is used to form a conjugate under click chemistry conditions wherein the reporter molecule, carrier molecule or another solid support comprises a terminal alkyne. In another embodiment the azido modified glycoprotein is attached to a solid support using functional groups other than azide reactive functional groups, whereupon the attached azido modified glycoprotein is used to form a conjugate under Staudinger ligation conditions wherein the reporter molecule, carrier molecule or another solid support comprises a triaryl phosphine.

In another aspect is provided a method for detecting immobilized azido modified biomolecules, wherein the method includes the following:
a) immobilizing the azido modified biomolecules on a solid or semi-solid atrix to form an immobilized azido modified biomolecule;
b) contacting the immobilized azido modified biomolecule with a reporter molecule that contains an alkyne reactive group to form a contacted azido modified biomolecule;
c) incubating the contacted azido modified biomolecule for a sufficient amount of time to form a reporter molecule-biomolecule conjugate;
d) illuminating the reporter molecule-biomolecule conjugate with an appropriate wavelength to form an illuminated reporter molecule-biomolecule conjugate, and
e) observing the illuminated reporter molecule-biomolecule conjugate whereby the immobilized azido modified biomolecule is detected.

In certain embodiments the azido modified biomolecule is an azido modified protein, while in other embodiments the azido modified biomolecule is an azido modified glycoprotein.

In another aspect is provided a method for detecting immobilized alkyne modified biomolecules, wherein the method includes the following:
a) immobilizing the alkyne modified biomolecules on a solid or semi-solid atrix to form an immobilized alkyne modified biomolecule;
b) contacting the immobilized alkyne modified biomolecule with a reporter molecule that contains an azide reactive group to form a contacted alkyne modified biomolecule;
c) incubating the contacted alkyne modified biomolecule for a sufficient amount of time to form a reporter molecule-biomolecule conjugate;
d) illuminating the reporter molecule-biomolecule conjugate with an appropriate wavelength to form an illuminated reporter molecule-biomolecule conjugate, and
e) observing the illuminated reporter molecule-biomolecule conjugate whereby the immobilized alkyne modified biomolecule is detected.

In certain embodiments the alkyne modified biomolecule is an alkyne modified protein, while in other embodiments the alkyne modified biomolecule is an alkyne modified glycoprotein.

Samples and Sample Preparation

The end user will determine the choice of the sample and the way in which the sample is prepared. Samples that can be used with the methods and compositions described herein include, but are not limited to, any biological derived material or aqueous solution that contains a biomolecule. In certain embodiments, a samples also includes material in which a biomolecule has been added. The sample that can be used with the methods and compositions described herein can be a biological fluid including, but not limited to, whole blood, plasma, serum, nasal secretions, sputum, saliva, urine, sweat, transdermal exudates, cerebrospinal fluid, or the like. In other embodiments, the sample are biological fluids that include tissue and cell culture medium wherein biomolecule of interest has been secreted into the medium. Cells used in such cultures include, but are not limited to, prokaryotic cells and eukaryotic cells that include primary cultures and immortalized cell lines. Such eukaryotic cells include, without limitation, ovary cells, epithelial cells, circulating immune cells, β cells, hepatocytes, and neurons. In certain embodiments, the sample may be whole organs, tissue or cells from an animal, including but not limited to, muscle, eye, skin, gonads, lymph nodes, heart, brain, lung, liver, kidney, spleen, thymus, pancreas, solid tumors, macrophages, mammary glands, mesothelium, and the like.

Various buffers can be used in the methods described herein, including inorganic and organic buffers. In certain embodiments the organic buffer is a zwitterionic buffer. By way of example only, buffers that can be used in the methods described herein include phosphate buffered saline (PBS), phosphate, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid)

(HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl)amino-methane (Tris), TRIS-Acetate-EDTA (TAE), glycine, bis[2-hydroxyethyl]iminotris [hydroxymethyl]methane (BisTris), or combinations thereof. In certain embodiments, wherein such buffers are used in gel electrophoresis separations the buffer can also include ethylene diamine tetraacetic acid (EDTA).

The concentration of such buffers used in the methods described herein is from about 0.1 mM to 1 M. In certain embodiments the concentration is between 10 mM to about 1 M. In certain embodiments the concentration is between about 20 mM and about 500 mM, and in other embodiments the concentration is between about 50 mM and about 300 mM. In certain embodiments, the buffer concentration is from about 0.1 mM to about 50 mM, while in other embodiments the buffer concentration if from about 0.5 mM to about 20 mM.

The pH will vary depending upon the particular assay system, generally within a readily determinable range wherein one or more of the sulfonic acid moieties is deprotonated.

In certain embodiments, buffers used in the methods described herein have a pH between 5 and 9 at ambient temperature. In certain embodiments the buffer has a pH between 6 and 8.5 at ambient temperature. In certain embodiments the buffer has a pH between 6 and 8 at ambient temperature. In certain embodiments the buffer has a pH between 6 and 7 at ambient temperature. In certain embodiments the buffer has a pH between 5 and 9 at 25° C. In certain embodiments the buffer has a pH between 6 and 8.5 at 25° C. In certain embodiments the buffer has a pH between 6 and 8 at 25° C. In certain embodiments the buffer has a pH between 6 and 7 at 25° C.

In certain embodiments, the sample used in the methods described herein have a non-ionic detergent to the sample. Non-limiting examples of such non-ionic detergents added to the samples used in the methods described herein are polyoxyalkylene diols, ethers of fatty alcohols including alcohol ethoxylates (Neodol from Shell Chemical Company and Tergitol from Union Carbide Corporation), alkyl phenol ethoxylates (Igepal surfactants from General Aniline and Film Corporation), ethylene oxide/propylene oxide block copolymers (PLURONIC™ Series from BASF Wyandotte Corporation), polyoxyethylene ester of a fatty acids (Stearox CD from Monsanto Company), alkyl phenol surfactants (Triton series, including Triton X-100 from Rohm and Haas Company), polyoxyethylene mercaptan analogs of alcohol ethoxylates (Nonic 218 and Stearox SK from Monsanto Company), polyoxyethylene adducts of alkyl amines (Ethoduomeen and Ethomeen surfactants from Armak Company), polyoxyethylene alkyl amides, sorbitan esters (such as sorbitan monolaurate) and alcohol phenol ethoxylate (Surfonic from Jefferson Chemical Company, Inc.). Non-limiting examples of sorbitan esters include polyoxyethylene(20) sorbitan monolaurate (TWEEN20), polyoxyethylene(20) sorbitan monopalmitate (TWEEN40), polyoxyethylene(20) sorbitan monostearate (TWEEN60) and polyoxyethylene(20) sorbitan monooleate (TWEEN 80). In certain embodiments, the concentration of such non-ionic detergents added to a sample is from 0.01 to 0.5%. In other embodiments the concentration is from about 0.01 to 0.4 vol. %. In other embodiments the concentration is from about 0.01 to 0.3 vol. %. In other embodiments the concentration is from about 0.01 to 0.2 vol. %. In other embodiments the concentration is from about 0.01 to 0.1 vol. %.

Illumination

The compounds and compositions described herein may, at any time before, after or during an assay, be illuminated with a wavelength of light that results in a detectable optical response, and observed with a means for detecting the optical response. In certain embodiments, such illumination can be by a violet or visible wavelength emission lamp, an arc lamp, a laser, or even sunlight or ordinary room light, wherein the wavelength of such sources overlap the absorption spectrum of a fluorophore or chromaphore of the compounds or compositions described herein. In certain embodiments, such illumination can be by a violet or visible wavelength emission lamp, an arc lamp, a laser, or even sunlight or ordinary room light, wherein the fluorescent compounds, including those bound to the complementary specific binding pair member, display intense visible absorption as well as fluorescence emission.

In certain embodiments, the sources used for illuminating the fluorophore or chromaphore of the compounds or compositions described herein include, but are not limited to, hand-held ultraviolet lamps, mercury arc lamps, xenon lamps, argon lasers, laser diodes, blue laser diodes, and YAG lasers. These illumination sources are optionally integrated into laser scanners, flow cytometer, fluorescence microplate readers, standard or mini fluorometers, or chromatographic detectors. These fluorescence emission of such fluorophores is optionally detected by visual inspection, or by use of any of the following devices: CCD cameras, video cameras, photographic film, laser scanning devices, fluorometers, photodiodes, photodiode arrays, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device.

In certain embodiments, fluorescence is optionally quenched using either physical or chemical quenching agents.

Kits of the Invention

In another aspect, the present invention provides kits that include UDP-GalNAz, a GalT enzyme; an azide reactive reporter molecule, carrier molecule or solid support.

In one aspect, the invention includes a kit for labeling a biomolecule that includes at least one label that comprises a terminal alkyne, a solution comprising copper, and a solution that comprises a copper (I) chelator. The kit can further comprise a solution that comprises a reducing agent, one or more buffers, or one or more detergents.

In one embodiment, an alkyne label provided in a kit is a fluorophore, such as, but not limited to, a xanthene, coumarin, borapolyazaindacene, pyrene and cyanine. In one embodiment, a kit provides two or more different terminal alkyne-containing labels one or more of which is a fluorophore, In other embodiments, an alkyne label provided in a kit is a tag, such as but not limited to a peptide or a hapten, such as biotin.

In preferred embodiments, a copper (I) chelator provided in the kit is a 1,10 phenanthroline, preferably bathocuproine disulfonic acid. In some embodiments, copper is provided in the form of a copper sulfate or copper acetate solution. In some embodiments, a reducing agent is provided in the form of ascorbate.

In another aspect, the invention includes a kit for labeling a biomolecule that includes at least one label that comprises an azido group, a solution comprising copper, an a solution that comprises a copper (I) chelator. The kit can further comprise a solution that comprises a reducing agent, one or more buffers, or one or more detergents.

In one embodiment of this aspect, an azido-containing label provided in a kit is a fluorophore, such as, but not limited to, a xanthene, coumarin, borapolyazaindacene, pyrene and cyanine. In other embodiments, an azido label provided in a kit is a tag, such as but not limited to a peptide or a hapten, such as biotin.

In one embodiment, a kit provides two or more different azido-containing labels one or more of which is a fluorophore, In preferred embodiments, a copper (I) chelator provided in the kit is a 1,10 phenanthroline, preferably bathocuproine disulfonic acid. In some embodiments, copper is provided in the form of a copper sulfate or copper acetate solution. In some embodiments, a reducing agent is provided in the form of ascorbate.

In other embodiments, a kit can further include one or more reagents and solutions for chromogenic detection on Western blots.

A detailed description of the invention having been provided above, the following examples are given for the purpose of illustrating the invention and shall not be construed as being a limitation on the scope of the invention or claims.

EXAMPLES

Example 1

Synthesis of UDPGalNAz

The synthesis of UDPGalNAz is shown in the following reaction scheme.

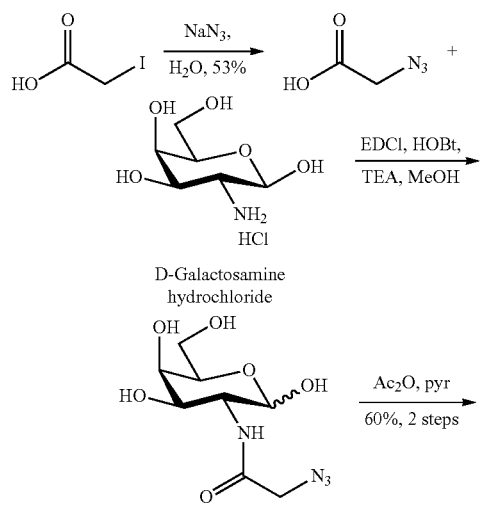

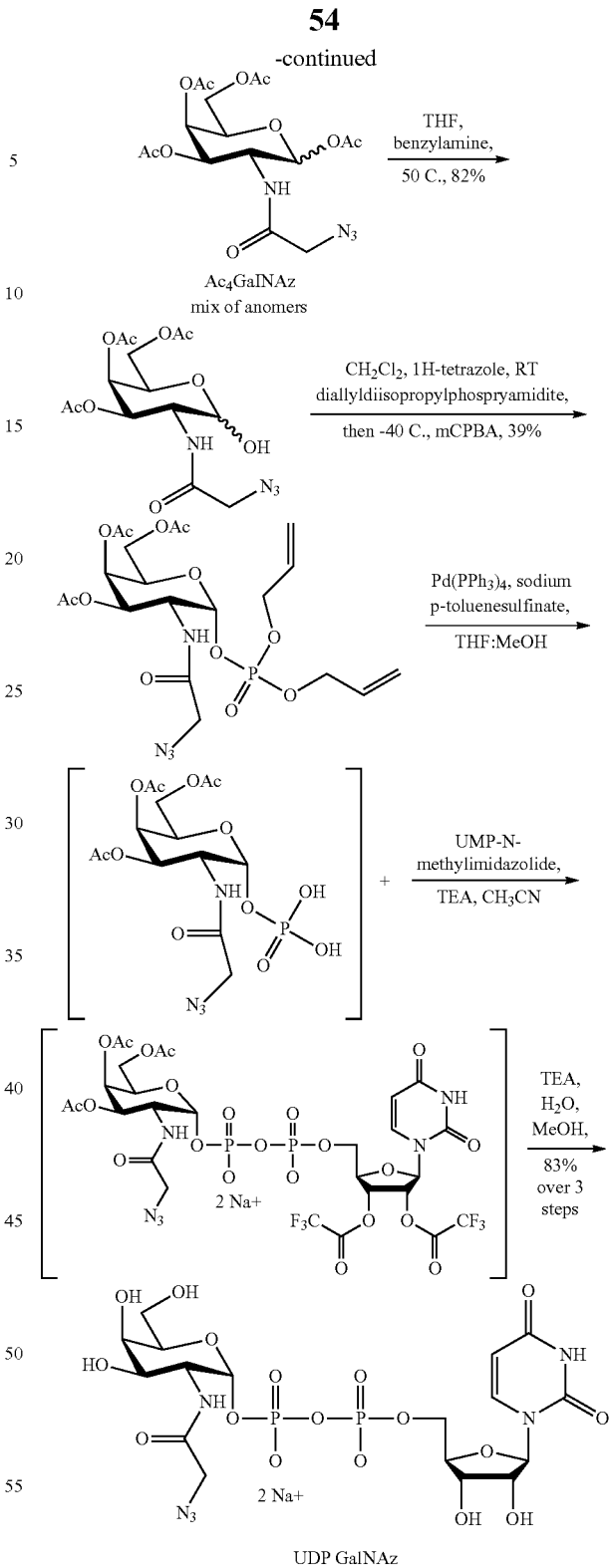

Azidoacetic acid. To a solution of iodoacetic acid (8.0 g, 43.0 mmol) and $H_2O$ (100 mL) was added sodium azide (5.62 g, 86.0 mmol). The solution was stirred at RT and protected from light. After 4 days, the solution was diluted with 1 N HCl (30 mL) and the pH was check to ensure that it was in the range of 2-3. The solution was extracted with EtOAc (2×100 mL), then the combined organics were washed with saturated $NaHSO_3$ (1×50 mL), brine (1×50 mL)

and dried over MgSO$_4$. The solution was decanted, concentrated and the crude azidoacetic acid (3.34 g, 53%) was used directly in the next step without further purification.

N-Azidoacetylgalactosamine (mix of anomers). To a solution of azidoacetic acid (3.34 g, 33.06 mmol) in methanol (170 mL) was added D-galactosamine hydrochloride (5.09 g, 23.62 mmol) followed by triethylamine (7.90 mL, 56.68 mmol). This solution was stirred at RT for 5 min and then cooled to 0° C. 1-Hydroxybenzotriazole (3.19 g, 23.62 mmol) was added followed by N-(3-dimethylaminopropyl)-N-ethylcarbodiimide hydrochloride (9.05 g, 47.24 mmol). The ice was allowed to melt on its own and the clear, pale orange reaction solution was stirred overnight at RT, and protected from light. The honey-colored solution was concentrated to yield a yellow resin. The crude yellow material (mixture of 2 anomers, assumed 100% conversion) was used directly in the next reaction without further purification.

1,3,4,6-Tetra-O-acetyl-N-azidoacetylgalactosamine (Ac$_4$GalNAz, mix of anomers). To a solution of N-azidoacetylgalactosamine (mix of anomers, 23.62 mmol) in pyridine (140 mL) was added acetic anhydride (70 mL). The cloudy, orange/brown colored solution was stirred at RT overnight and protected from light. The solution was concentrated to yield a brown, viscous oil. The crude oil was purified via silica gel loaded with 33-50% EtOAc/hexanes, affording 4.35 g (60%, mixture of 2 anomers) of the product.

3,4,6-Tri-O-acetyl-N-azidoacetylgalactosamine (mix of anomers). To a solution of 1,3,4,6-tetra-O-acetyl-N-azidoacetylgalactosamine (mix of anomers, 1.60 g, 3.75 mmol) in THF (20 mL) was added benzylamine (0.49 mL, 4.5 mmol). The solution was heated in an oil bath at 50° C. and protected from light. After 15 hr, the initial clear, canary yellow solution turned brown in color. The solution was removed from the oil bath and concentrated. The crude was purified via silica column chromatography (50-100% EtOAc/hexanes) to afford the product (1.18 g, 82%, brown oil, mixture of 2 anomers).

Diallyl (3,4,6-tetra-O-acetyl-2-azidoacetiamido-2-dexocy-α-D-galactopyranosyl phosphate. To a solution of 3,4,6-tri-O-acetyl-N-azidoacetylgalactosamine (mix of anomers, 0.34 g, 0.88 mmol) in CH$_2$Cl$_2$ (9.0 mL) was added 1H-tetrazole (0.31 g, 4.41 mmol). The reaction was stirred at RT for 10 min and protected from light. Diallyldiisopropylphosphoramidite (0.70 mL, 2.64 mmol) was added dropwise and the reaction was stirred at RT for 3 h. The solution was subsequently cooled to −40° C. in an acetonitrile/dry ice bath and 3-chloroperbenzoic acid (0.76 g, 4.41 mmol) and stirred at −40° C. for 10 min. The solution was then allowed to warm to RT slowly over 1 h (transferred from a −40° C. bath to 0° C. bath packed with ice). After 1 hr, ice was still present so removed ice bath and let stir at RT for 20 min. The reaction solution was diluted with CH$_2$Cl$_2$ (45 mL), washed sequentially with 10% aqueous Na$_2$SO$_3$ (2×45 mL), saturated NaHCO$_3$ (2×45 mL), and H$_2$O (2×45 mL). The organic layer was then dried over Na$_2$SO$_4$, decanted and concentrated. The crude material was purified via silica gel column chromatography (60-100% EtOAc/hexanes) to afford the product, (0.18 g, 39%).

UDPGalNAz. To a solution of diallyl (3,4,6-tetra-O-acetyl-2-azidoacetiamido-2-dexocy-α-D-galactopyranosyl phosphate (0.10 g, 0.18 mmol) and THF:MeOH (1:1, 2.1 mL:2.1 mL) under argon was added p-toluenesulfonic acid, sodium salt (0.14 g, 0.72 mmol) followed by tetrakis(triphenylphosphine)palladium(0) (30 mg, 0.026 mmol). The solution was protected from light and stirred at RT for 3 h. After 4 days, the reaction solution was concentrated in vacuo and co-evaporated with toluene (3×20 mL). The crude material was suspended in CH$_3$CN (0.86 mL) and triethylamine (0.27 mL) was added. The solution was cooled to 0° C. and freshly prepared UMP-N-methylimidazole (0.22 mmol) in CH$_3$CN (1.7 mL) was added dropwise. The resulting yellow solution was stirred at 0° C. for 3 h. The reaction solution was concentrated, then resuspended in a solution of MeOH:H$_2$O:triethylamine (5:2:1, 10 mL) and stirred at RT for 20 h. The solution was concentrated in vacuo to yield a crude yellow syrup. This material was dissolved in H$_2$O (15 mL) and extracted with CH$_2$Cl$_2$ (3×50 mL) to remove organic byproducts. The organic layer was discarded and the aqueous layer was concentrated and co-evaporated with toluene. The resulting viscous, pale orange, clear oil was obtained. The crude material was dissolved in 100 mM NH$_4$HCO$_3$ degassed buffer (2.0 mL). Because the solution was cloudy in appearance and not clear, it was filtered through a Acrodisc PF 0.8/0.2 mM Supor, sterile, single use, non-pyrogenic filter from Gelman Sciences, prod #4187. The clear, pale orange solution obtained was loaded onto a BioGel P2, extra fine column (1.5 cm×80 cm) and flashed at a flow rate of 0.13 mL/min. The column was run overnight with 100 mM NH$_4$HCO$_3$ buffer; 2.6 mL per fraction were collected. The fractions containing product were collected (TLC 5:3:1, EtOH, NH$_4$OH, H$_2$O, R$_f$=0.70, UV active). After combining the product-containing fractions, the solution was concentrated and the resulting white solid was dissolved in a minimal amount of water and passed through a Dowex (BioRad AG 50W-X8-200 resin, purchased in the sodium form). All of the eluent was collected and concentrated after the UV active material ceased eluting from the column. A pale, tan foam was obtained. This material was dissolved in minimal water and lyophilized to afford the product (0.10 g, 83%) as a tan, crystalline material.

Example 2

Synthesis of UMP-N-methylimidazolide

The synthesis of UMP-N-methylimidazolide is shown in the following reaction scheme.

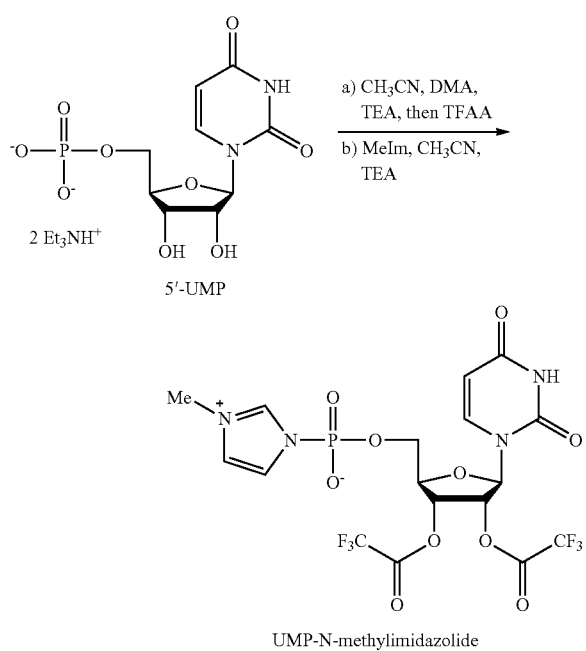

Uridine 5′-monophosphate triethylammonium salt (5′-UMP triethylammonium salt). Uridine 5′-monophosphate disodium salt (1.0 g) was dissolved in H$_2$O (2 ml) and passed through Dowex resin triethylammonium salt (2.7 cm×7.0 cm column size) with H$_2$O as eluent. All of the eluent was concentrated and after the UV active material ceased eluting from the column. The solution was concentrated and co-evaporated with toluene to until a white, crystalline solid was obtained (0.78 g, 80%).

Uridine monophosphate-N-methylimidazole (UMP-N-methylimidazole). To a suspension of uridine 5′-monophosphate triethylammonium salt (0.097 g, 0.22 mmol) in CH$_3$CN (0.70 mL) was added N,N-dimethylaniline (0.11 mL, 0.864 mmol), and triethylamine (0.03 mL, 0.22 mmol). The suspension was cooled to 0° C. In a separate flask, trifluoroacetic anhydride (0.15 mL, 1.08 mmol) was added to CH$_3$CN (0.21 mL) and cooled to 0° C. This solution was added dropwise via microsyringe, to the suspension of uridine 5′-monophosphate triethylammonium salt at 0° C.; a yellow, clear solution was obtained. After 5 min, the solution was removed from the ice bath and stirred at RT for 30 min. The solution was concentrated in vacuo and placed under dry argon. The mixed phosphoryl anhydride solution was then cooled to 0° C. In a separate flask methylimidazole (0.051 mL, 0.65 mmol) was added to a solution of CH$_3$CN (0.2 mL) and triethylamine (0.15 mL, 1.08 mmol). The resulting clear and colorless solution was cooled to 0° C. and subsequently added dropwise to the mixed phosphoryl anhydride solution at 0° C. The solution was then stirred at 0° C. for 5-10 min. The yellow color darkened and after 20 min and the TLC (10:10:1, CHCl$_3$:MeOH:1 mM NH$_4$OAc pH 7), showed complete conversion to product (R$_f$=0.28, UV active). CH$_3$CN (1.7 mL) was added to the solution at 0° C., and this crude material was used directly in the next step; 100% conversion is assumed.

Example 3

Synthesis of Dapoxyl® Alkyne

The synthesis of Dapoxyl® alkyne is shown in the following reaction scheme.

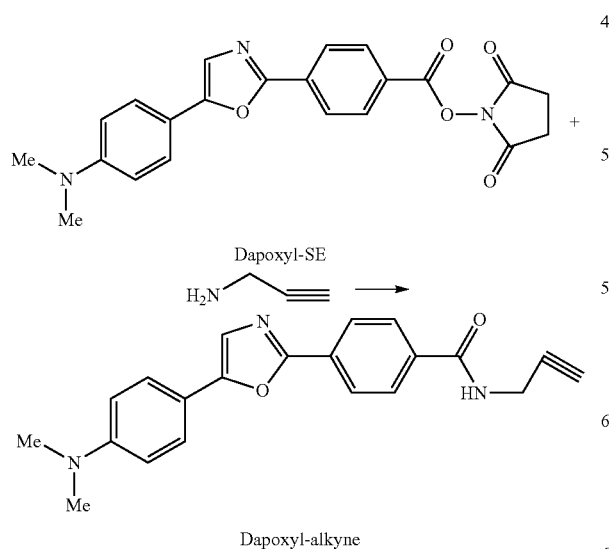

To a solution of Dapoxyl® carboxylic acid, succinimidyl ester (50 mg, 0.12 mmol) in DMF (0.4 mL) at RT was added propargylamine (42 µL, 0.61 mmol). The initial clear orange solution turned yellow and cloudy. After ~15 min at RT the reaction was complete, and the solution was concentrated to dryness. The residue was purified via HPLC to afford the product (36 mg, 84%). TLC (10% EtOAc, CHCl$_3$) R$_f$=0.30; ESI m/z 346 (M$^+$, C$_{21}$H$_{19}$N$_3$O$_2$ requires 346).

Example 4

Synthesis of 5-Carboxytetramethyl rhodamine alkyne (5-TAMRA-alkyne)

The synthesis of 5-Carboxytetramethyl rhodamine alkyne (5-TAMRA-alkyne) is shown in the following reaction scheme.

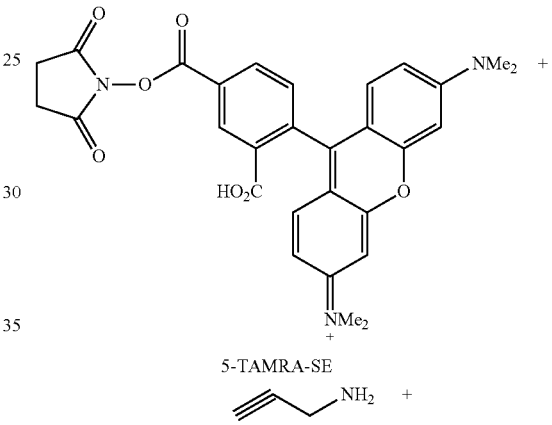

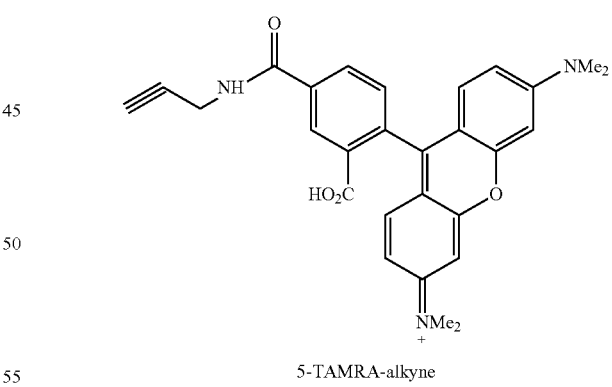

To a solution of 5-carboxytetramethyl rhodamine, succinimidyl ester (5-TAMRA-SE, 0.10 g, 0.19 mmol) in DMF (0.5 mL) was added propargylamine (25 µL, 0.38 mmol) and H$_2$O (0.5 mL). After stirring the solution for 30 min at RT, the solution was concentrated in vacuo. Purification via HPLC (Phenomenex Prodigy ODS, internal diameter 21.2 mm, eluent 25-40% CH$_3$CN in 25 mM TEAA, pH 4.7, flow rate of 15 mL/min) gave 68 mg of product (82%, a purple solid) t$_R$=23-33 min. TLC(CH$_3$CN:H$_2$O, 8:2) R$_f$=0.67.

Example 5

Synthesis of Biotin Alkyne

The synthesis of Biotin alkyne is shown in the following reaction scheme.

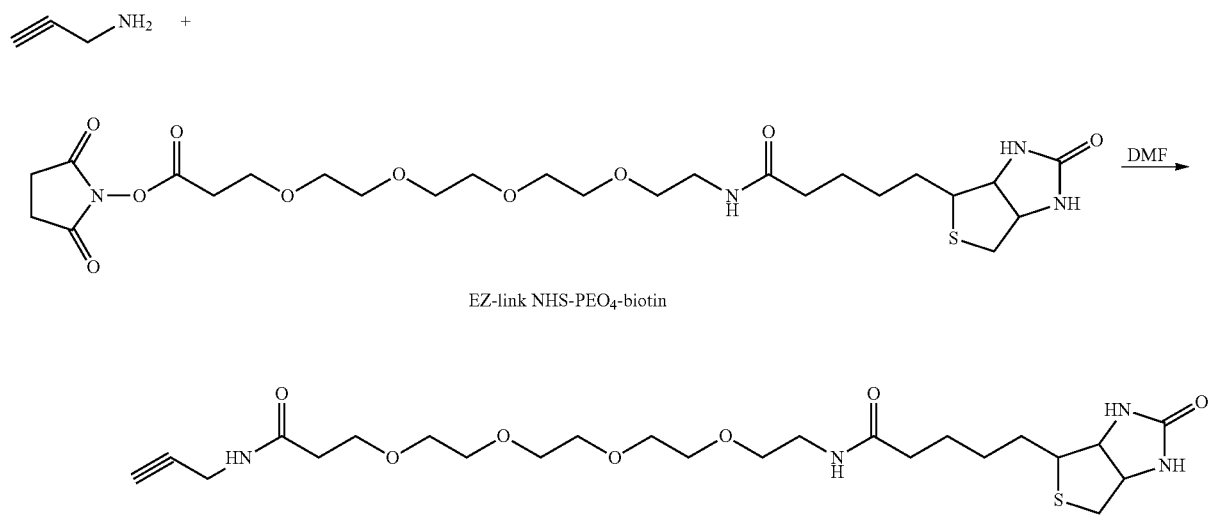

EZ-link NHS-PEO₄-biotin

To a solution of EZ-link NHS-PEO$_4$-biotin (25 mg, 0.004 mmol, Pierce) in DMF (0.1 mL) was added propargylamine (0.1 mL). After stirring the solution for 90 min at RT, some starting material was still seen. Additional propargylamine (0.2 mL) was added and the solution was stirred for another 60 min. The solution was concentrated in vacuo. The crude material was purified via HPLC to afford 14.4 mg (64%) of the product as a yellow solid. TLC (CHCl$_3$: MeOH, 7:1) R$_f$=0.23; ESI m/z 529 (M$^+$, C$_{24}$H$_{40}$N$_4$O$_7$S requires 529).

Example 6

Synthesis of Compound 1

The synthesis of Compound 1 is shown in the following reaction scheme.

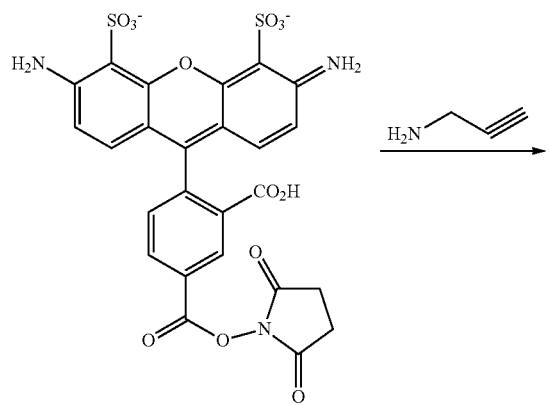

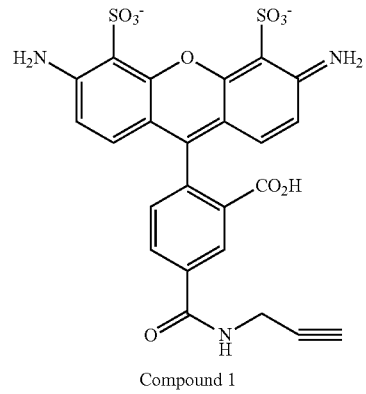

Compound 1

To a solution of Alexa Fluor® 488 carboxylic acid, succinimidyl ester, dilithium salt (mixed isomers, 50 mg, 0.079 mmol) in DMF (2.0 mL) was added propargylamine (54 L, 0.79 mmol). The solution was stirred overnight at RT. The initial deep red solution turned pale yellow in color and became clear. The solution was concentrated in vacuo and purified via silica gel thin layer chromatography (prep plate, 20% H$_2$O, CH$_3$CN) to afford the product (20 mg, 44%) as an orange solid. TLC (3:1, CH$_3$CN:H$_2$O) R$_f$=0.70; ESI neg m/z 570 (M$^+$, C$_{24}$H$_{16}$N$_3$O$_{10}$S$^{2-}$ requires 570).

Example 7

Synthesis of Compound 2

The synthesis of Compound 2 is shown in the following reaction scheme.

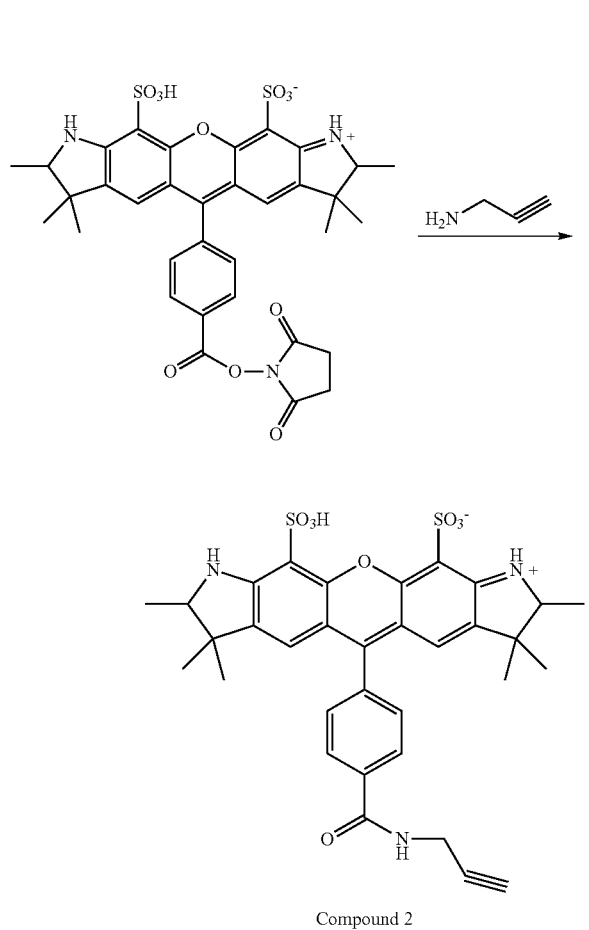

Compound 2

To a solution of Alexa Fluor® 532 carboxylic acid, succinimidyl ester (50 mg, 0.070 mmol) in DMF (2.2 mL) was added propargylamine (100 L, 1.46 mmol). The solution was stirred overnight at RT. H$_2$O (1.0 mL) was added to the solution and the solution was stirred an additional hour. The solution was concentrated in vacuo and the crude material was purified via HPLC to afford the product (30 mg, 65%). TLC (8:2, CH$_3$CN:H$_2$O) R$_f$=0.58; ESI m/z 664 (M$^+$, C$_{33}$H$_{33}$N$_3$O$_8$S$_2$ requires 664).

Example 8

Synthesis of Compound 3

The synthesis of Compound 3 is shown in the following reaction scheme.

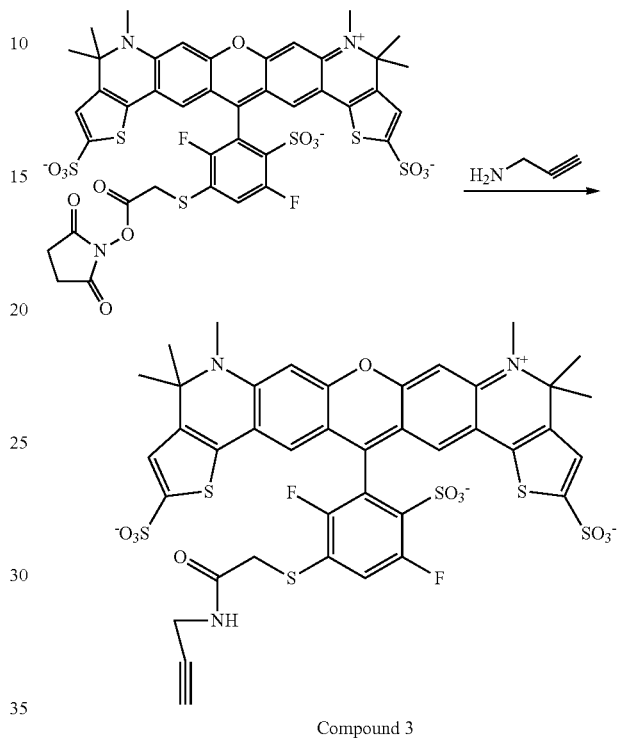

Compound 3

To a solution of Alexa Fluor® 633 carboxylic acid, succinimidyl ester, bis(triethylammonium salt) (50 mg, 0.041 mmol) in DMF (2.0 mL) was added propargylamine (28 µL, 0.40 mmol). The solution was stirred overnight at RT. H$_2$O (1.0 mL) was added to the solution and the solution was stirred an additional hour. The solution was concentrated in vacuo and the product (39 mg, 99%). TLC (8:2, CH$_3$CN:H$_2$O) R$_f$=0.66; ESI m/z 963 (M$^+$, C$_{40}$H$_{34}$F$_2$N$_3$O$_{11}$S$_6$ requires 963).

Example 9

Synthesis of Triarylphosphine-TAMRA Dye for Staudinger Ligation

The synthesis of triarylphosphine-TAMRA dye is shown in the reaction scheme below.

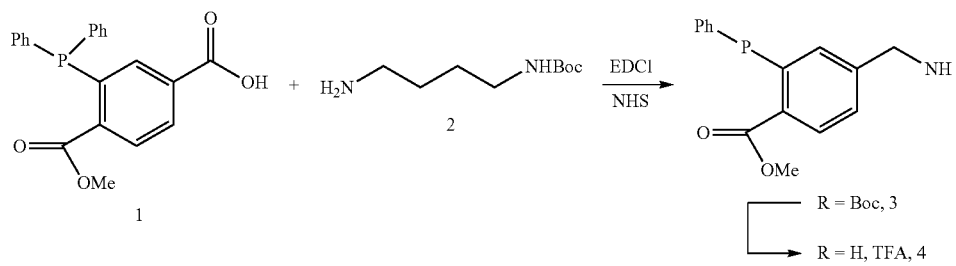

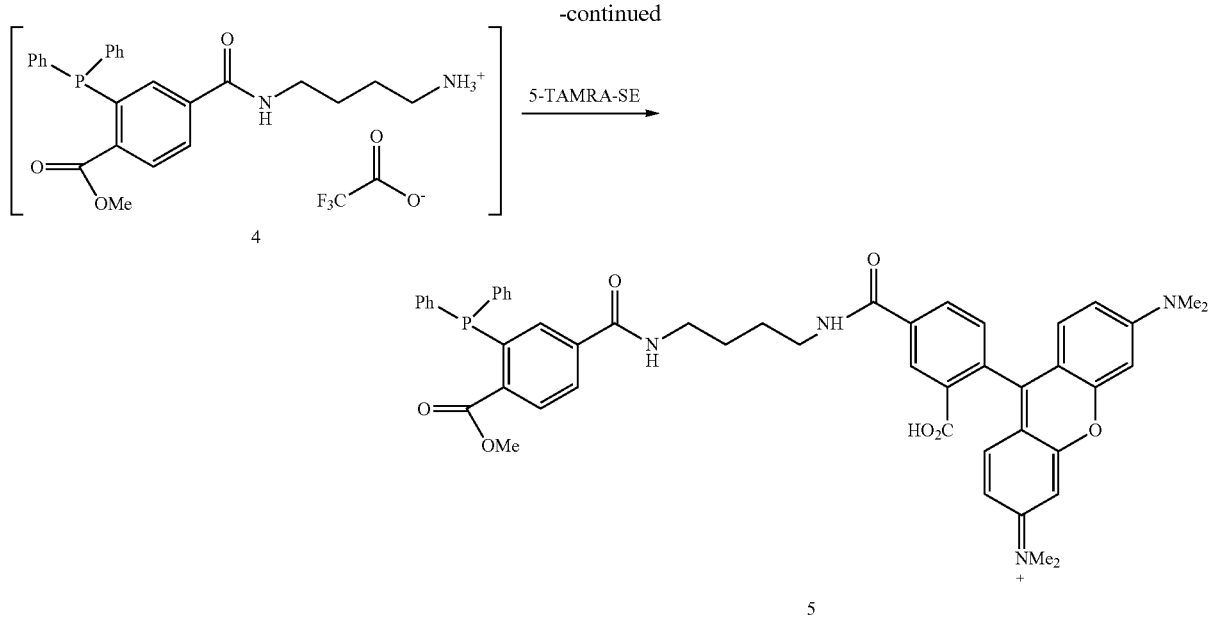

To a solution of acid 1 (*Science* 2000, 287, 2007-2010) (80 mg, 0.26 mmol) in CH$_2$Cl$_2$ (5 mL) was added N-(3-dimethylaminopropyl)-N'-ethylcarbodiimide hydrochloride (EDCI, 75 mg, 0.39 mmol) and N-hydroxysuccinimide (NHS, 5 mg). The solution was stirred at RT. After 2.5 h, amine 2 (50 μL, 0.26 mmol) was added and the solution was stirred overnight. The solution was partitioned between CHCl$_3$ (15 mL) and H$_2$O (5 mL). The organic layer was separated and the aqueous layer was reextracted with CHCl$_3$ (15 mL). The combined organic layers were rinsed once with H$_2$O (5 mL), followed by saturated aqueous NaCl (5 mL). The organic layer was dried over Na$_2$SO$_4$, decanted and concentrated. The crude was purified via chromatography (silica, 2% MeOH, CHCl$_3$) to afford the product (99 mg, 71%) as a clear, yellow oil.

To a solution of 3 (10 mg, 0.018 mmol) in CH$_2$Cl$_2$ (1.0 mL) was added trifluoracetic acid (TFA, 0.5 mL) and the solution was stirred at RT. After 30 min, the solution was concentrated and reevaporated from toluene (2×2 mL). The residue (4, 0.018 mmol) was dissolved in DMF (0.2 mL) and N-ethyldiisopropylamine (DIEA, 12 uL, 0.72 mmol), and 5-carboxytetramethyl rhodamine, succinimidyl ester (5-TAMRA-SE, 9 mg, 0.022 mmol) were added. The solution was stirred at RT for 2.5 h, concentrated and purified via silica gel (prep plate, 20% H$_2$O in CH$_3$CN) to afford the product (7.4 mg, 48%). TLC (20% H$_2$O in CH$_3$CN) R$_f$=0.23; ESI m/z 529 (M$^+$, C$_{24}$H$_{40}$N$_4$O$_7$S requires 529).

Example 10

Synthesis of Triarylphosphine-Biotin for Staudinger Ligation

The synthesis of triarylphosphine-biotin is shown in the following reaction scheme.

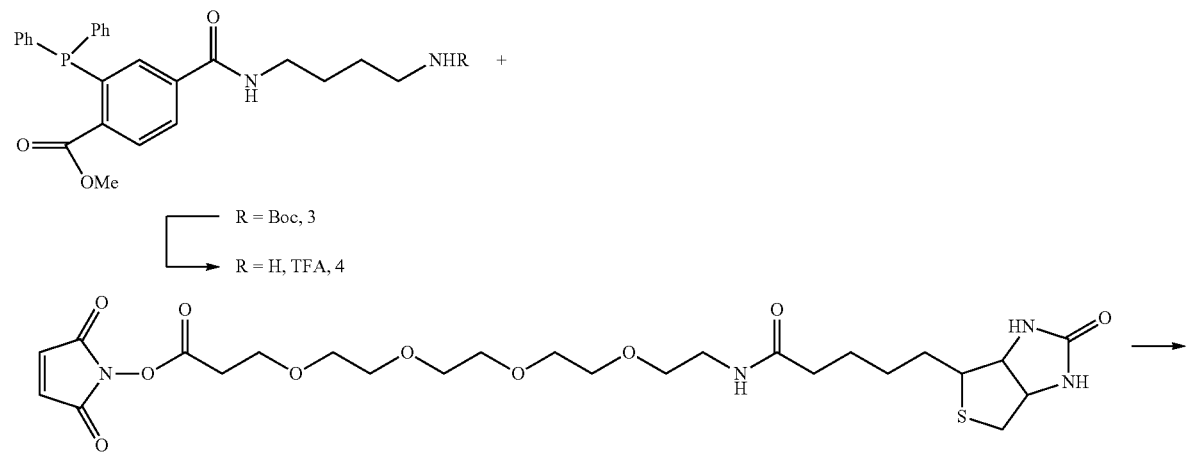

-continued

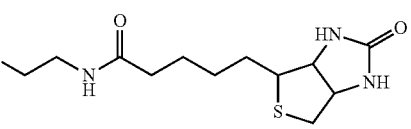

To a solution of 3 (5.3 mg, 0.010 mmol) in CH$_2$Cl$_2$ (1.2 mL) was added trifluoracetic acid (TFA, 0.5 mL) and the solution was stirred at RT. After 2 h, the solution was concentrated and reevaporated from toluene (2×2 mL). The residue (4, 0.010 mmol) was dissolved in DMF (0.1 mL) and N-ethyldiisopropylamine (DIEA, 3 µL, 0.02 mmol), and EZ-link NHS-PEO$_4$-biotin (7 mg, 0.012 mmol) were added. The solution was stirred at RT for 1 h, quenched with saturated NH$_4^+$Cl$^-$ and partitioned between CHCl$_3$ (10 mL) and H$_2$O (1 mL). The aqueous layer was extracted repeatedly with CHCl$_3$ (10 mL per extraction) until no ultraviolet spot was observed by TLC. The combined organic layers were concentrated and purified via silica gel (prep plate, 7:1 CHCl$_3$:MeOH) to afford the product (2.2 mg, 25%). TLC (7:1 CHCl$_3$:MeOH, developed 3 times) R$_f$=0.50; ESI m/z 909 (M+H$^+$, C$_{46}$H$_{63}$N$_5$O$_{10}$PS requires 909).

Example 11

Metabolic Labeling and "Click" Detection of Glycoprotein Subclasses

Jurkat cells were fed 40 µM Ac$_4$ManNAz or Ac$_4$GalNAz for 3 days (A) or 250 µM Ac$_4$GlcNAz overnight (B). Harvested cells were sonicated in 50 mM Tris buffer, pH 8.0 with protease and phosphatase inhibitors, and the lysates were subjected to high-speed centrifugation (100K×g). The membrane pellet proteins from ManNAz- and GalNAz-treated cells, and the soluble supernatant cells from the GlcNAc-treated cells, were precipitated with chloroform/methanol, dissolved in detergent, and labeled with a fluorescent alkyne probe in the presence of 1 mM CuSO4, and 5 mM ascorbic acid (1). 10 µg of the labeled, precipitated proteins were run on 1-D NuPAGE® Novex® 4-12% gels (Invitrogen). Images were obtained on the Fuji FLA-3000 scanner (Fuji) using 532 nm excitation. Gels were then post stained with SYPRO® Ruby protein stain (Invitrogen, Carlsbad, Calif.) and imaged using excitation at 473 nm. Control lanes represent extracts from unfed cells but treated with the fluorescent probe. See FIG. 2.

Example 12

Separation of Ac$_4$GlcNAz-Treated Soluble Jurkat Cell Proteins by 2-D Gels

Jurkat cells were cultured overnight with 250 µM Ac$_4$GlcNAz. Soluble lysate proteins were prepared as above using sonication and ultracentrifugation and labeled for 1 hour with a fluorescent alkyne probe. 40 µg of the labeled proteins were precipitated and resolubilized in 7M urea, 2M thiourea, 65 mM DTT, 2% CHAPS, 1% Zwittergent 3-10, 1% pH 3-10 carrier ampholytes and separated on pH 3-10 IEF strips in the first dimension and 4-12% Bis-Tris gels with MOPS buffer in the second dimension. See FIG. 3.

Example 13

In Gel Detection of 40 and 50 kD Azide-Labeled Model Proteins 25 pmols each of 40 and 50 kD model proteins with single N-terminal azides were spiked into 100 µg of Jurkat cell lysates (upper panels), or not (lower panels). Proteins were labeled with a fluorescent alkyne probe, serially diluted as shown, and run on NuPAGE® Novex® 4-12% gels. Images (left panels) were obtained on the FLA-3000 scanner using 532 nm excitation. Gels were then post stained with SYPRO® Ruby stain and imaged using excitation at 473 nm (right panels). Detection sensitivity of the labeled proteins is less than 10 femtomoles. See FIG. 4.

Example 14

Labeling Efficiency of 40 and 50 kd Azide-Labeled Model Proteins is Unchanged in Complex Protein Extracts Either 100 ng (25 pmol) or 10 ng (2.5 pmol) each of azide-labeled 40 Kd & 50 Kd proteins were labeled with fluorescent alkyne probe as above in a background of either 100, 50, 25, or 0 µg of control Jurkat lysate (left panel). Note: 100 µg of control lysate was added after labeling to the '0 lysate' to facilitate recovery of the labeled protein by precipitation. The gel was post stained with SYPRO® Ruby total protein stain. See FIG. 5.

Example 15

Selective Analysis of Cell Surface Versus Total Glycoprotein Subclasses by Gel Electrophoresis HeLa cells were fed Ac$_4$GalNAz or Ac$_4$ManNAz sugars for 48 hours. For cell surface glycoprotein analysis, the surfaces of live cells were labeled with dye-alkyne, lysed, and the purified proteins were analyzed by gel electrophoresis (lanes 2 and 5, see legend). For total glycoprotein subclass analysis, cells were lysed, the purified proteins were labeled in solution, and ran on the gel (lanes 3 and 6). Control unfed cells are shown in gel lanes 1 and 4. 20 µg of protein was loaded per gel lane. The GalNAz incorporated proteins in lane 2 represent cell surface O-linked glycoproteins only, whereas total GalNAz metabolically labeled glycoproteins are shown in lane 3. These proteins represent both cell surface O-linked glycoproteins, intracellular GalNAz labeled proteins located in golgi apparatus and transport vesicles, and O-GlcNAc modified proteins (GalNAz was recently shown to flux into the O-GlcNAc biosynthetic pathway). Lane 5 represents ManNAz labeling of cell surface sialic acid-containing glycoproteins, whereas lane 6 represents labeling of both cell surface sialic acid-containing glycoproteins and intracellular sialic acid-containing glycoproteins located in golgi apparatus and transport vesicles.

Example 16

Metabolic Labeling of Glycoprotein Subclasses in Live Animals and in Gel Fluorescence Detection of Labeled Glycoproteins Metabolic labeling of O-linked and sialic acid-containing glycoproteins was accomplished by administration of the unnatural tetraacetylated azide-modified sugar precursors, $Ac_4GalNAz$ or $Ac_4ManNAz$, respectively (300 mg/kg in 70% DMSO), to activated Her2/Neu transgenic mice over a 7 day regimen. After 7 days the mice were sacrificed and various organ tissues were dissected, lysed, and protein extracts were reacted with 10 mM fluorescent TAMRA alkyne in Tris Buffer, pH 8.0, with 2 mM $CuSO_4$, 20 mM ascorbate, 5 mM BCS, and 25% propylene glycol. Labeled glycoproteins were precipitated, dissolved in 1-D SDS-PAGE buffer, analyzed by gel electrophoresis, and detected by fluorescence laser scanning. After scanning the gels were post-stained with SYPRO® Ruby total protein stain to view total proteins. The upper panels below show 1-D gels of labeled tissue proteins from heart muscle (H), liver (L), or kidney (K). Lower panels show same gels after post-staining with SYPRO® Ruby total protein stain.

Example 17

Fluorescent "Click" Labeling of Live and Fixed Cells: Selective Labeling of Cell Surface Versus Internal Glycoproteins Jurkat cells were fed 30 μM $Ac_4HexNAz$ sugars, ManNAz, GalNAz, or GlcNAz, for 3 days. In A, live Jurkat cells were labeled with 10 mM Alexa Fluor 488 alkyne probe for 30 minutes in the presence of Tris buffer, pH 8.0, 2 mM $CuSO_4$, 20 mM ascorbate, and 5 mM BCS. The cells were then fixed with 4% formaldehyde/PBS for 15 min and analyzed by flow cytometry. In B, cells were fixed and permeablized, before labeling under the same conditions as in A, and analyzed by flow cytometry. Theses results demonstrate the ability to selectively stain cell surface glycoproteins only, or cell surface and intracellular glycoproteins. Significant GlcNAz staining is apparent only after cell permeabilization, as the modification is specific to the inside of the cell.

Example 18

Enzymatic Labeling and Detection of α-Crystallin O-GlcNAc

α-crystallin O-GlcNAc was enzymatically labeled with azide (UDP-GalNAz) using a modified b-GalT1 enzyme. The protein was subsequently reacted with a fluorescent alkyne probe as described. The proteins were run on 1-D NuPAGE® Novex® 4-12% gels at the dilutions shown. Note: Only 2-10% of α-crystallin is O-GlcNAc-modified and therefore the detection sensitivity of the O-GlcNAc moiety is in the mid-to-low femtomole range (10-45 fmols). See FIG. 6.

Example 19

Comparison of GalT1 Enzyme Labeling with a-O-GlcNAc Monoclonal Antibody CTD 110.6

Figure 7:
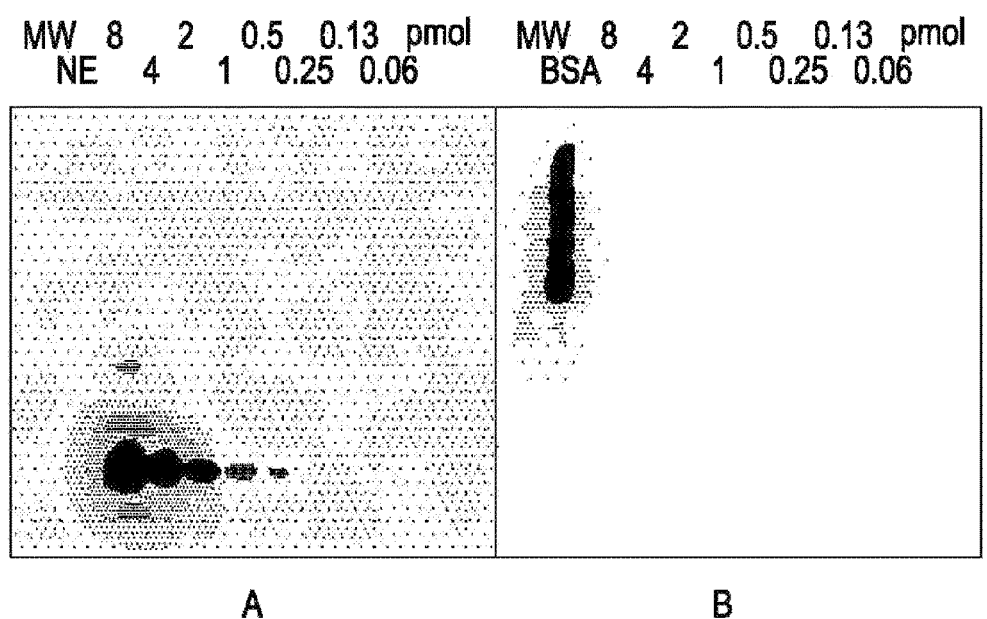
FIG. 7: Shows the Comparison of GalT1 Enzyme Labeling with a-O-GlcNAc Monoclonal Antibody CTD 110.6.

In A, α-crystallin was enzymatically labeled with the modified GalT1 enzyme and subsequently reacted with a biotin-alkyne probe. The proteins were run on 1-D NuPAGE® Novex® 4-12% MES gels, at the dilutions shown, and blotted onto PVDF membrane. The PVDF membrane was then incubated in streptavidin-HRP and proteins were detected using ECL Plus™ (GE Biosystems). Lane 2 (NE) represents the 8 pmoL no-enzyme added control. Note: In A, the detection sensitivity of O-GlcNAc by Western blot is in the low femtomole range (3-10 fmols). In B, untreated α-crystallin was run on 1-D gels and blotted as described above. The PVDF membrane was processed using the O-GlcNAc Western Blot Detection Kit (Pierce) according to manufacturer's instructions. The kit utilizes the CTD110.6 α-O-GlcNAc monoclonal antibody. Lane 2 contains 5 ng of the positive control (O-GlcNAc-modified BSA) provided in the kit. No α-crystallin is detected using the antibody detection system. See FIG. 7.

Example 20

Multiplex Detection of O-GlcNAc Proteins, Phosphoproteins and Total Proteins in the Same 2-D Gel Soluble extracts from GlcNAz-fed Jurkat cells were labeled with UV excitable alkyne dye for 2 hours. The chloroform/methanol precipitated proteins were run on 2-D gels as described previously. The gel was rinsed in water and imaged with UV transillumination and 600/bp emission on a Lumi-Imager™ (Roche). The gel was then stained with Pro-Q® Diamond phosphoprotein stain, imaged with 532 nm excitation/580 LP emission on a FLA-3000 laser imager, stained with SYPRO® Ruby total protein stain, and imaged again with 473 nm excitation and 580 nm longpass emission according to the manufacturer's instructions. See FIG. 8.

Example 21

Multiplexed Western Blot Detection of O-GlcNAc and Cofilin

25 μg of soluble Jurkat cell proteins from Example 12 were run on 2-D gels as described and blotted onto PVDF membrane. The PVDF membrane was incubated in α-cofilin polyclonal Ab and detected with GAR-HRP secondary Ab with ECL Plus™ detection (GE Biosystems). After imaging, the blot was incubated in streptavidin AP and O-GlcNAc proteins were detected using the WesternBreeze® chemiluminescent detection kit (Invitrogen). See FIG. 9.

Example 22

Differential Detection of O-GlcNAc Modified Proteins in Control and Inhibitor-Treated Cultured Cell Extracts Jurkat cells cultured overnight with $Ac_4GlcNAz$ with and without PUGNAc treatment. PUGNAc is a commonly used inhibitor of O-GlcNAcase. Soluble Jurkat lysate preparations were labeled with fluorescent alkyne. Lane 1) cells treated with 50 μM PUGNAc and 4 mM glucosamine 3 hrs prior to harvest; Lane 2) no treatment; Lanes 3-5) cells cultured overnight with 250 μM Ac4GlcNAz; Lanes 6-8) cells cultured overnight with 250 μM Ac4GlcNAz then treated with 50 μM PUGNAc and additional 250 μM Ac4GlcNAz 3 hrs prior to harvest. Proteins treated with PUGNAc (lanes 6-8) show a marked increase in O-GlcNAc staining over the untreated controls (lanes 3-5). See FIG. 10.

Example 23

In-Gel Ligation of Glycoproteins

Fluorescent alkyne compounds for use in in-gel ligation are shown in FIG. 12 (FIGS. 12A-12D). Additionally, 2 potential fluorogenic alkynes are shown in FIG. 12E and FIG. 12F. The TAMRA-alkyne compound, shown in the upper left-hand frame, was used in in-gel staining experiments whereby azido groups were incorporated into proteins in vitro using a reactive azido-succinimidyl ester, or in vivo, by feeding cells azido-modified sugars.

Example 24

Azide-Alkyne Reaction Conditions for In-Gel or Western Blot Detection

The proteins should be in 50 mM Tris-HCl, pH 8.0 with 1.0% SDS.
Final volume is 200 uL.

| Component | Volume | Final |
|---|---|---|
| Protein in 1% SDS, 50 mM Tris pH 8 | 50 uL | 100-200 ug |
| Tris-HCl, pH 8.0 (1M) | 7.5 uL | 50 mM |
| Propylene glycol | 50 uL | 25% |
| $CuSO_4$ (50 mM) | 4 uL | 1 mM |
| DMSO, 0.5M | 4 uL | 10 mM |
| H20 | 62.5 uL | to 200 uL |
| Alkyne compound 1 mM (eg TAMRA or biotin) | 2 uL | 10 uM |
| Na Ascorbate (100 mM) | 10 uL | 5 mM |

Combine all components adding the ascorbate last. Vortex gently.
Add 10 uL of 100 mM BCS (it will turn orange if CuI is present).
Vortex gently.
Layer with argon.
Mix on rotator at room temperature for 1 hour.
After the reaction, chloroform/methanol precipitate the protein using the following protocol:

| | | |
|---|---|---|
| 200 uL Reaction | | |
| 600 uL MeOH,. | vortex 20 secs, (freeze 30' if protein amt. is low) | |
| 200 uL chloroform | vortex 20 secs | |
| 450 uL $H_2O$ | vortex 20 secs | |

Spin @ 18K×g for 5 min
Remove upper phase and add 450 MeOH. Vortex 20 secs
Spin @ 18K×g for 5 min
Remove supernatant and discard
Add 600 uL MeOH only, vortex, and briefly sonicate to disperse pellet
Spin @ 18K×g for 5 min
Na Ascorbate (mw 198) Dilution to 100 mM:

| Na Ascorbate, dry, | 5 mg |
|---|---|
| H2O | 250 uL |

Figure 13:
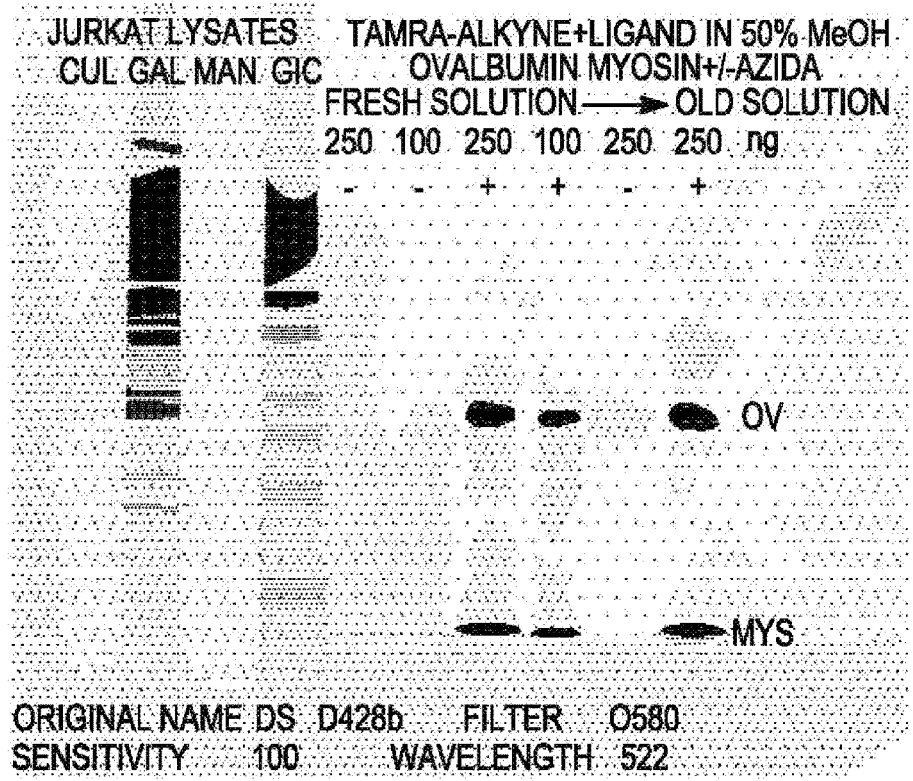
FIG. 13: shows the results of in-gel staining using the TAMRA-alkyne compound shown in FIG. 12A. Lanes 2, 3, and 4 on the left side of the gel represent cellular extracts that were labeled with azide-modified sugars: lane 1 is the control, non-labeled cells. On the right, control azide labeled proteins (ovalbumin and myoglobin) (+) or non-labeled controls (−) are shown at varying concentrations. The results show very efficient and selective in-gel labeling of azido-modified proteins.

Cell lysates were obtained from cultured Jurkat cells that were fed azido-modified sugars. FIG. 13, shows the results of electrophoresis of proteins labeled with the TAMRA-Alkyne compound using the protocol provided. Lanes 2, 3, and 4 on the left side of the gel represent cellular extracts that had incorporated azido-modified sugars, lane 1 is the control, non-azide sugar fed cells. On the right, control azide labeled proteins (ovalbumin and myoglobin) (+) or non-labeled controls (−) are shown at varying concentrations. The results show very efficient and selective in-gel detection of azido-modified proteins.

Example 25

2.5 μg each of azido-ovalbumin and azido-myoglobin were spiked into 80 ug of unlabeled Jurkat lysate. The lysate was then labeled with TAMRA alkyne for 2 hrs. The reaction contained 50 mM TRIS pH8, 25% propylene glycol, 1 mM $CuSO_4$, 5 mM sodium ascorbate, 20 uM TAMRA alkyne. The reactions were performed with and without a chelator (10 mM of either TPEN, EDTA, bathocuproine disulfonic acid (BCS) or neocuproine). The control reaction was performed without $CuSO_4$. After labeling, the samples were precipitated, resolubilized in 7 mM urea/2 mM thiourea/65 mM DTT/2% CHAPS/and approximately 30 μg of each sample was analyzed on 2-D gels (pH 4-7 IEF strips, 4-12% BIS-TRIS gels with MOPS buffer). The TAMRA signal was imaged at 532 nm excitation, 580 long pass emission on a Fuji FLA3000 then the gels were post-stained with SYPRO® Ruby total protein gel stain (FIGS. 14 A1 and 14A2). The results show that addition of chelator greatly improves the resolution of the protein separation. bathocuproine disulfonic acid (BCS), a Cu I chelator, gives the best results. See total protein stain, FIGS. 14 B1 and 14B2.

In a second experiment, the samples and click labeling conditions were the same, except that chelator treatments included the addition of either 5 mM TPEN, BCS, or Neocuproine at the beginning of the reaction. After labeling, the samples were precipitated, resolubilized in LDS buffer+ 5 mM TCEP and serial 2-fold dilutions were performed. Dilutions were loaded onto 4-12% BIS-TRIS gels with MOPS running buffer (250 ng each of ovalbumin and myglobin in lane 1). FIGS. 15 A1 and A2 show that the chelators reduce the background of the image for the TAMRA signal without compromising sensitivity. In FIGS. 15 B1 and B2, post-staining with Sypro® Ruby total protein gel stain shows that the band resolution is much better for the samples with chelator.

Figure 16A:
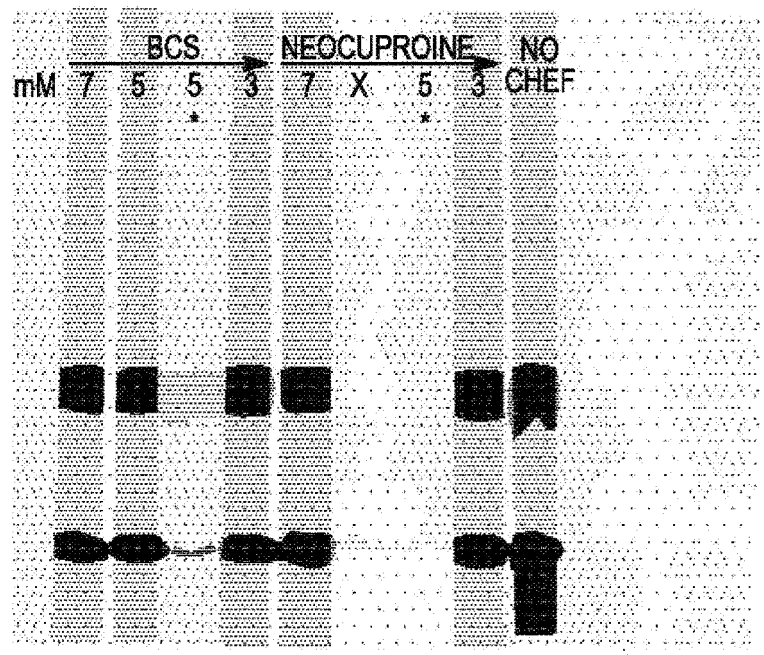
FIG. 16: The samples and click labeling conditions for FIGS. 16A and 16B are the same as for FIG. 14, except that chelator treatments include addition of either 7 mM, 5 mM or 2 mM BCS or neocuproine. The lanes marked with an asterisk in (FIG. 16A) indicate reactions in which the $CuSO_4$ and BCS were added to the reaction and vortexed prior adding the sodium ascorbate. In all other reactions the $CuSO_4$ and sodium ascorbate were added and vortexed prior to adding the BCS. The gels show that it is imperative to add the sodium ascorbate and $CuSO_4$ to the reaction tube and mix prior to adding the chelator. If the chelator and $CuSO_4$ are added and vortexed prior to adding the sodium ascorbate, the azide-alkyne labeling does not proceed, suggesting that the chelator inhibits the reduction of Cu(II) to Cu(I).
Figure 16B:
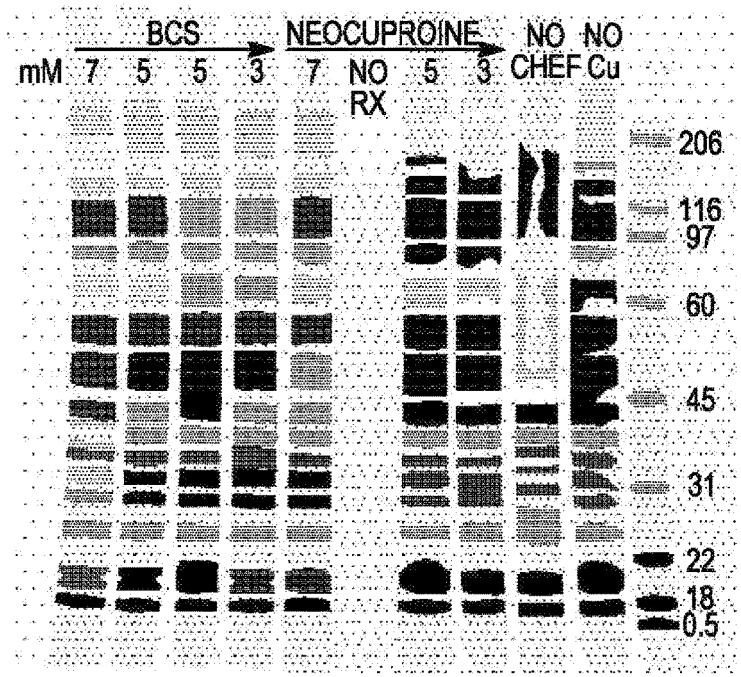

A further experiment testing the effect of chelators used the same click labeling conditions except that the chelator treatments included addition of either 7 mM, 5 mM, or 2 mM BCS; or 7 mM, 5 mM, or 2 mM neocuproine. The lanes marked with an asterisk in FIG. 16 indicate reactions in which the CuSO4 and BCS were added to the reaction and vortexed prior adding the sodium ascorbate. In all other reactions the CuSO4 and sodium ascorbate were added and vortexed prior to adding the BCS. The gels show that it is imperative to add the sodium ascorbate and CuSO4 to the reaction tube and mix prior to adding the chelator. If the chelator and CuSO4 are added and vortexed prior to adding the sodium ascorbate, the azide-alkyne labeling does not proceed, suggesting that the chelator inhibits the reduction of Cu (II) to Cu (I).

Example 26

Enzymatic Labeling of Antibodies Using Click Chemistry

Goat IgG antibodies were reduced and alkylated, then deglycosylated in 2 separate aliquots using Endo Hf enzyme. Deglycosylated antibodies (2 separate preps) were then labeled with GalNAz using 33 ng/uL Gal T1 Y289L enzyme and 500 uM UDP GalNAz (0.5 ug/uL goat antibody) in a 150 uL reaction. Reactions were incubated at 4 degrees C. overnight. 4-500 ng of goat antibody (treated as listed on gel; either no-GalNAz control or azide labeled) was loaded into each lane of a 4-12% Bis Tris gel. Electrophoresis was performed at 200 v for ~50 min. using MES buffer. Gels were stained with TAMRA-alkyne stain and imaged on the Fuji imager at 532 nm (excitation) and 580 nm emission. Gels were poststained with SYPRO Ruby using the overnight protocol. See FIG. 17

Example 27

Synthesis of Cy™5.5Azide

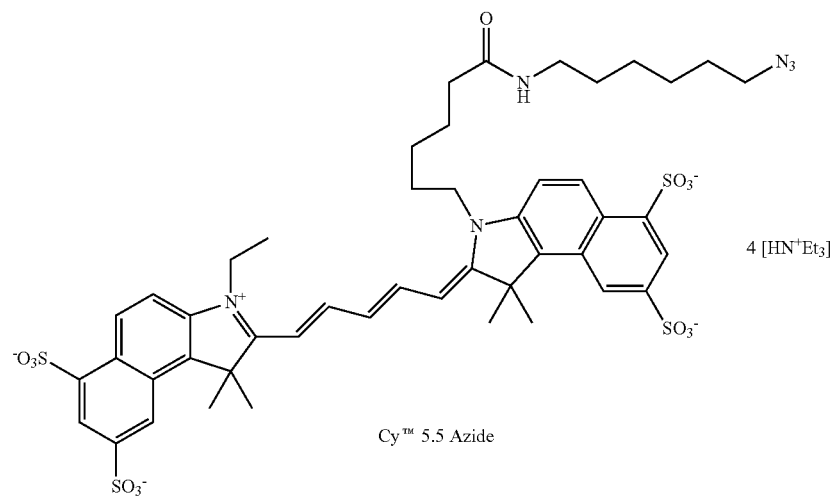

Cy™ 5.5 Azide

To a solution of 6-(amino)-hexanyl-1-azide trifluoroacetic acid salt (see Scheme 1 for synthesis, 0.034 mmol) in DMF (0.1 mL) and DIEA (6.0 μL, 0.034 mmol) was added Cy™5.5 succinimidyl ester (5 mg, 3.4 nmol). After stirring the solution at RT for 10 min, the reaction solution was concentrated in vacuo. The crude was purified via HPLC.

Example 28

Synthesis of Cy™3Azide

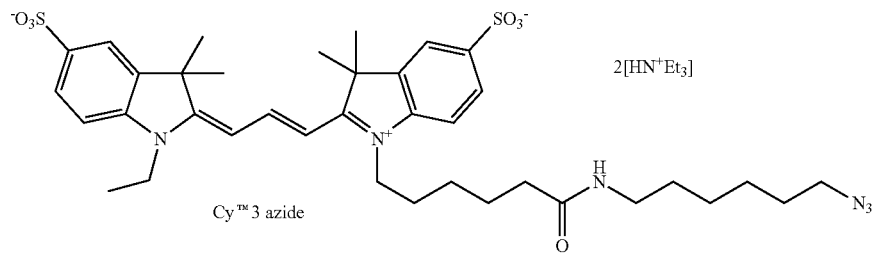

Cy™ 3 azide

To a solution of 6-(amino)-hexanyl-1-azide trifluoroacetic acid salt (see Scheme 1 for synthesis, 0.052 mmol) in DMF (0.1 mL) and DIEA (9.2 μL, 0.052 mmol) was added Cy™3 succinimidyl ester (5.0 mg, 5.2 nmol). After stirring the solution at RT for 10 min, the reaction solution was concentrated in vacuo. The crude was purified via HPLC.

Example 29

Synthesis of Cy™5.5Alkyne

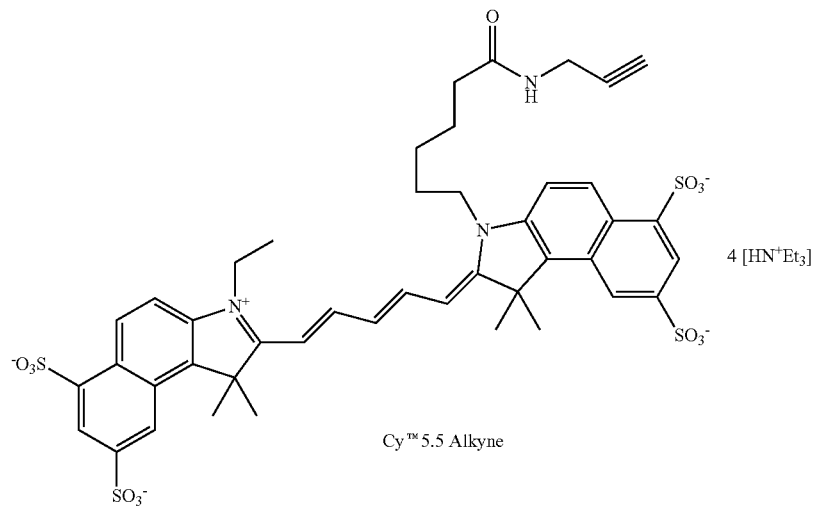

Cy™ 5.5 Alkyne

To a solution of Cy™5.5 succinimidyl ester (GE Amersham, 5.0 mg, 3.7 nmol) in DMF (0.1 mL) was added propargylamine (2.5 μL, 0.037 mmol) and $H_2O$ (0.2 mL). The solution was stirred at RT for 30 min then concentrated in vacuo. The crude was purified via HPLC.

Example 30

Synthesis of Cy™3Alkyne

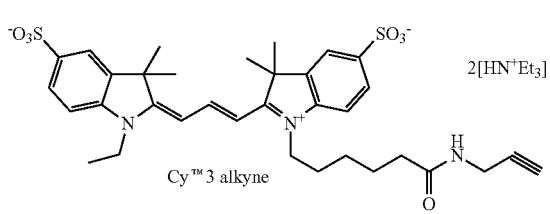

Cy™3 alkyne

To a solution of Cy™3 succinimidyl ester (GE Amersham, 5.0 mg, 5.7 nmol) in DMF (0.1 mL) was added propargylamine (3.9 μL, 0.057 mmol) and $H_2O$ (0.2 mL). The solution was stirred at RT for 30 min then concentrated in vacuo. The crude was purified via HPLC.

Example 31

Metabolic Labeling with Azido Farnesyl Alcohol and Detection with Click-iT™ TAMRA Detection Reagent COS7 and Jurkat cells were fed Lovastatin to suppress endogenous isoprenylation and azido-farnesyl alcohol (FN3-OH) for 36 or 72 hours. The dose was either 25 μM Lovastatin and 20 uM FN3-OH or 50 μM lovastatin and 50 μM FN3-OH. The media was replaced (including FN3-OH, but not lovastatin) for one set of samples cultured for 72 hours. Lysates were prepared by washing the cells 3 times with PBS and lysing with 1% SDS/100 mM TRIS pH 8+protease inhibitors (1 mL of lysis buffer per 100 cm culture dish). The lysate was sonicated, heated at 70° C. for 10 minutes then 200 μL aliquots were precipitated and frozen. Precipitated pellets were resolubilized with 50 μL of 1% SDS/100 mM TRIS pH 8, labeled with the TAMRA Click-iT™ detection kit (C33370) and 20 μg was analyzed on a 4-12% BIS-TRIS gel using MOPS buffer. The gels were imaged on the BioRad FX imager using the 532 nm laser and 555 nm long pass emission filter. The gels were post-stained with SYPRO® Ruby protein gel stain and imaged using the 488 nm laser and 555 nm long pass emission filter.

Example 32

Metabolic Labeling with Azido Fatty Acid Analogs and Detection with "Click" Reagents Azido-labeled fatty acid compounds, such as the palmitate compound shown below, or alkyne-labeled fatty acid compounds are added to cultured cells for a time period that allows the compound to enter the cells and become incorporated into fatty acid-modified macromolecules, including proteins. Compounds that facilitate entry of the analogs into the cells can also be used. After labeling, the cells are lysed and cellular azide- or alkyne-modified proteins are labeled using the appropriate click partner probe in the presence of copper(I), or copper(II) in the presence of a copper(II) reducing agent, a copper(I) chelating agent such as BCS, and an appropriate buffer to maintain optimal pH conditions.

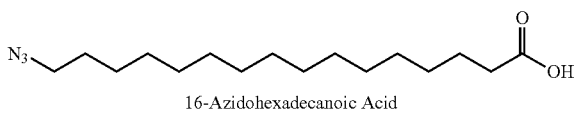 [SMILES: [N-]=[N+]=NCCCCCCCCCCCCCCCC(=O)O]

16-Azidohexadecanoic Acid

Example 33

Metabolic Labeling with Azido Fatty Acid Analogs and Detection with "Click" Reagents Azido-labeled fatty acid compounds, such as the palmitate compound shown below, or alkyne-labeled fatty acid compounds are added to cellular extracts in vitro, or under in vitro translation conditions. The fatty acylated proteins are detected by labeling the azide- or alkyne-modified proteins using the appropriate click partner probe in the presence of copper(I), or copper(II) in the presence of a copper(II) reducing agent, a copper(I) chelating agent such as BCS, and an appropriate buffer to maintain optimal pH conditions.

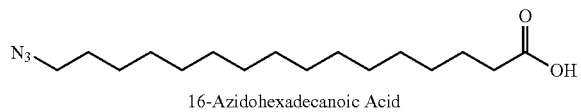 [SMILES: [N-]=[N+]=NCCCCCCCCCCCCCCCC(=O)O]

16-Azidohexadecanoic Acid

Example 34

Palmitic Acid Azide Synthesis

The synthesis of palmitic acid azide is shown in the following reaction scheme.

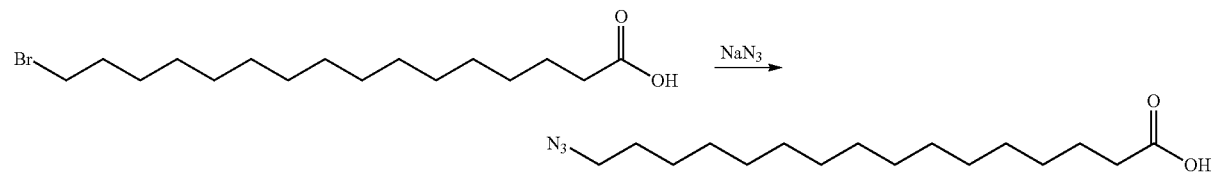

To a solution of 16-bromohexadecanoic acid (0.50 g, 1.49 mmol) in DMSO (10 mL) was added sodium azide (0.14 g, 2.24 mmol). The reaction was stirred at RT overnight. The solution was then cooled in an ice bath and quenched with water (10 mL). After stirring for 5 min, the ice bath was removed and the solution was allowed to warm to RT on its own. The resulting solution was then extracted with diethyl ether (2×60 mL) and the organic layers were combined, rinsed with saturated NaCl (3×10 mL), then dried over sodium sulfate. The solution was decanted, concentrated and purified by silica gel chromatography (10-25% EtOAc/hexanes containing 1% acetic acid) to afford a clear, colorless oil (0.33 g, 75%). TLC (25% EtOAc/hexanes) $R_f$=0.54, faint UV, brown spot if treated with PPh$_3$/toluene then stained with ninhydrin. IR (KBr pellet) 2126.9 cm$^{-1}$.

Example 35

Succinimidyl Ester Azide Synthesis

The synthesis of succinimidyl ester azide is shown in the following reaction scheme.

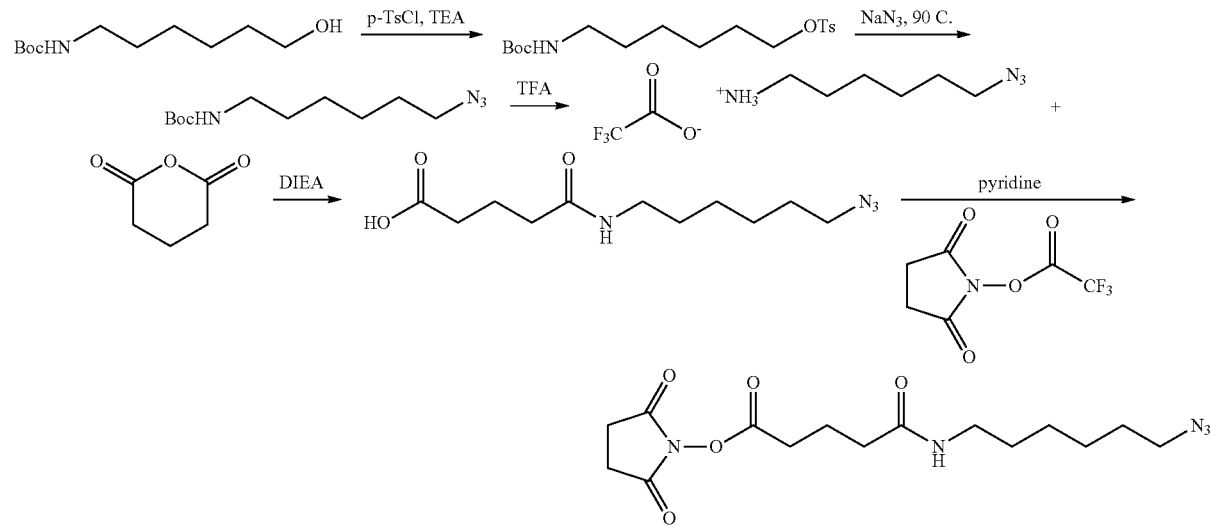

6-(Boc-Amino)-hexanyl-1-p-toluenesulfonate

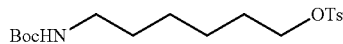

To a solution of 6-(Boc-amino)-1-hexanol (3.0 g, 13.8 mmol) in CHCl₃ (50 mL) was added TEA (3.8 mL, 27.6 mmol) and p-toluenesulfonyl chloride (3.9 g, 20.7 mmol). The solution was stirred at RT overnight, diluted with CHCl₃ (200 mL), washed with H₂O (4×50 mL), rinsed with brine (1×50 mL) and dried over Na₂SO₄. The solution was decanted, concentrated and purified via silica gel chromatography (6.0×41 cm, 20-70% EtOAc/hexanes) to afford the product as a white solid (3.5 g, 69%). TLC (35% EtOAC/hexanes) $R_f$=0.72, UV active.

6-(Boc-Amino)-hexanyl-1-azide

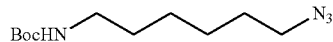

To a solution of 6-(Boc-amino)-hexanyl-1-p-toluenesulfonate (3.2 g, 8.63 mmol) in DMF (21 mL) was added sodium azide (1.12 g, 17.3 mmol). The solution was refluxed at 95° C. overnight. After cooling to RT, the solution was diluted with Et₂O (160 mL) and washed with H₂O (100 mL). The aqueous layer was extracted a second time with Et₂O (100 mL) and the combined organics were dried over Na₂SO₄. After decanting and concentrating, the crude material was purified via silica gel chromatography (6×26 cm, 25-30% EtOAc/hexanes) to afford the product as a clear, colorless oil (2.0 g, 97%). TLC, (35% EtOAC/hexanes) $R_f$=0.74, brown spot with ninhydrin stain.

6-(Amino)-hexanyl-1-azide trifluoroacetic acid salt

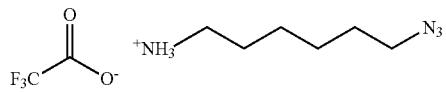

To a solution of 6-(Boc-amino)-hexanyl-1-azide (0.2 g, 0.83 mmol) in CH₂Cl₂ (1.0 mL) was added TFA (1.0 mL). The solution was stirred at RT for 2 h, evaporated to dryness and re-evaporated twice from toluene. The product, 6-amino-hexanyl-1-azide trifluoroacetic acid salt (0.83 mmol) was used directly without further purification.

(N-6-Azido-hexanyl)glutaramide

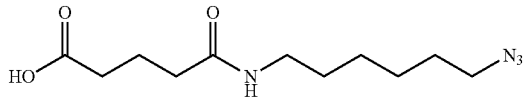 [SMILES: [N-]=[N+]=NCCCCCCNC(=O)CCCC(=O)O]

6-Amino-hexanyl-1-azide (0.83 mmol) was dissolved in THF (1.0 mL) and N,N-diisopropylethylamine (0.29 mL, 1.65 mmol) was added. The solution was stirred at RT for 10 min then glutaric anhydride (0.47 g, 4.13 mmol) was added. The pale yellow solution was stirred at RT overnight. The reaction solution was diluted with CHCl₃ (30 mL) and H₂O (10 mL), and acidified to a pH of 1 with 1% HCl; the organic layer was removed. The aqueous layer was extracted two more times with CHCl₃ (2×30 mL). The combined organic layers were rinsed with brine (2×10 mL) and dried over Na₂SO₄. The solution was decanted, and concentrated. The crude was purified via silica gel chromatography (10% MeOH/CHCl₃ containing 0.1% AcOH) to afford the product as a clear, colorless oil (0.16 g, 75%). The column was loaded with 10% MeOH/CHCl₃. TLC (10% MeOH/CHCl₃ with 0.1% AcOH) $R_f$=0.41, pink with p-anisaldehyde stain, no UV activity.

(N-6-Azido-hexanyl)glutaramide, succinimidyl ester

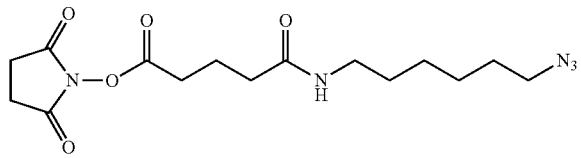 [SMILES: [N-]=[N+]=NCCCCCCNC(=O)CCCC(=O)ON1C(=O)CCC1=O]

To a solution of the (N-6-azido-hexanyl)glutaramide (75 mg, 0.29 mmol) in THF (4.0 mL) was added pyridine (110 μL, 1.36 mmol) followed by succinimidyl trifluoroacetate (200 mg, 0.95 mmol). The clear, colorless solution was stirred at RT for 4 h. The reaction solution was diluted with CHCl₃ (20 mL) and rinsed sequentially with 1% AcOH (2×5 mL), H₂O (2×5 mL) and brine (1×5 mL). The crude solution was dried over Na₂SO₄, decanted, and concentrated to afford the product as a clear, colorless oil (0.10 g, 99%). TLC: (1:1, EtOAc/hexanes) $R_f$=0.64, orange with ninhydrin, UV active.

Example 36

Succinimidyl Ester Alkyne Synthesis

The synthesis of succinimidyl ester alkyne is shown in the following reaction scheme.

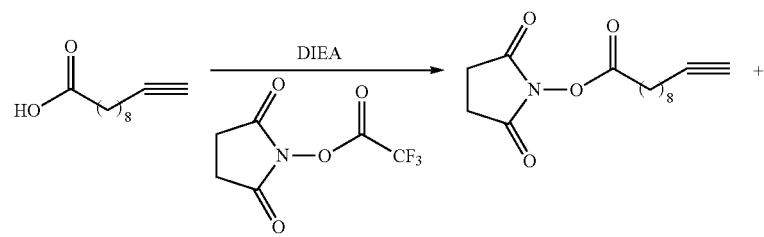

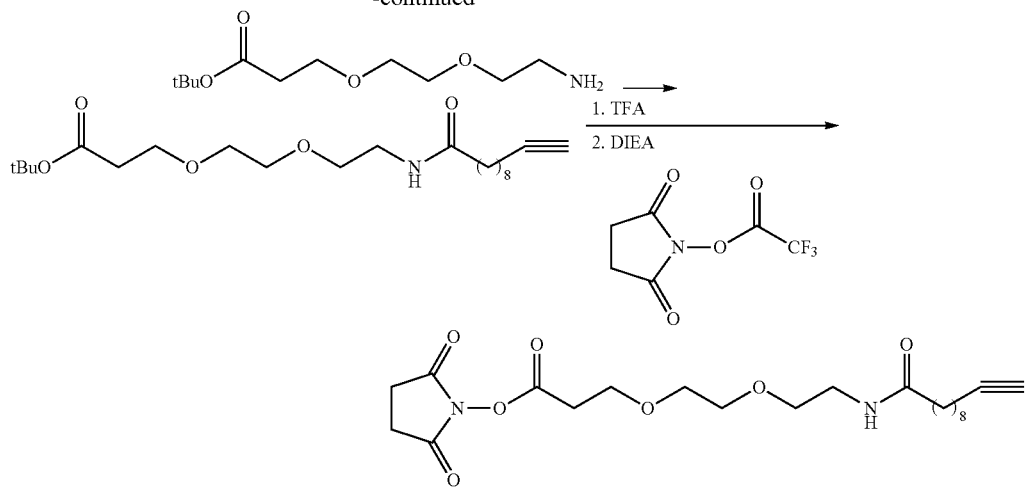

10-Undecynoic acid succinimidyl ester

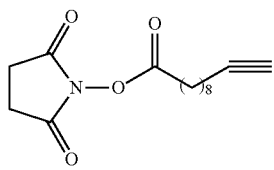

To a solution of 10-undecynoic acid (0.40 g, 2.2 mmol) in CH$_3$CN (10 mL) was added O-(N-succinimidyl)-N,N,N',N'-tetramethyluronium tetrafluoroborate (0.99 g, 3.29 mmol). After stirring for 2 min at RT, the reaction was quenched with 1% AcOH and diluted with CHCl$_3$ (150 mL). The organic solution was then extracted with 1% AcOH (10 mL), rinsed with H$_2$O (2×40 mL), then dried over Na$_2$SO$_4$. The solution was then decanted and concentrated. A quantitative yield was assumed and the material was taken on directly to the next step. TLC (10% MeOH/CHCl$_3$) R$_f$=0.90, UV active.

tert-Butyl alkyne

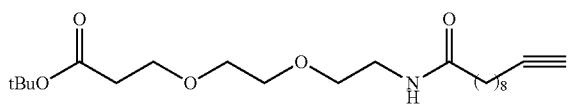

To a solution of 10-undecynoic acid succinimidyl ester (0.61 g, 2.19 mmol) in CH$_3$CN (8 mL) was added amino-dPEG™$_2$-tert-butyl ester (0.46 g, 1.97 mmol, Quanta BioDesign) in CH$_3$CN (2 mL) at RT. After 2 hrs, the solution was diluted with CHCl$_3$ (50 mL) and extracted with H$_2$O (5 mL). The aqueous layer was reextracted with CHCl$_3$ (2×50 mL). Combined organics were dried over Na$_2$SO$_4$, decanted and concentrated. The crude was purified via silica gel chromatography (2.5% MeOH/CHCl$_3$) to afford the product as a clear, pale yellow oil (0.48 g, 55%). TLC (9:1 CH$_3$CN:H$_2$O) R$_f$=0.81.

Succinimidyl ester alkyne

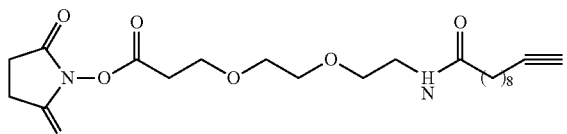

To a solution of tert-butyl alkyne (0.48 g, 1.2 mmol) in CH$_2$Cl$_2$ (2.0 mL) was added TFA (2.0 mL). The solution was stirred for 1 h, then concentrated and reevaporated from toluene (2×1 mL). The resulting brown residue was dissolved in CH$_3$CN (5.0 mL) and N,N-diisopropylethylamine (0.84 mL, 4.83 mmol) was added. The solution was stirred at RT for 2 min, and then O-(N-succinimidyl)-N,N,N',N'-tetramethyluronium tetrafluoroborate (0.47 g, 1.56 mmol) was added. After 15 min the reaction was quenched and acidified with 1% AcOH to a pH of 4-5. The solution was extracted with CHCl$_3$ (3×50 mL). The combined organics were reextracted with H$_2$O (1×10 mL), then dried over Na$_2$SO$_4$, decanted and concentrated to afford a tan solid (0.46 g, 87%). The crude material was pure enough for testing without further purification. TLC (8:2 CH$_3$CN/H$_2$O) R$_f$=0.79.

Example 37

Iodoacetamide Azide Synthesis

The synthesis of Iodoacetamide azide is shown in the following reaction scheme.

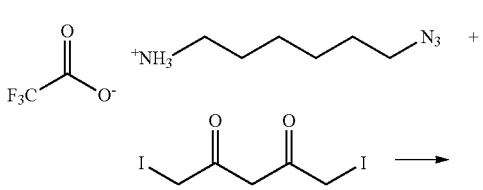

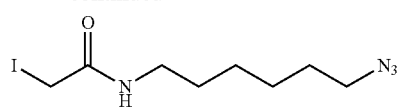 [SMILES: [N-]=[N+]=NCCCCCCNC(=O)CI]

6-(iodoacetamide)-aminohexanyl-1-azide

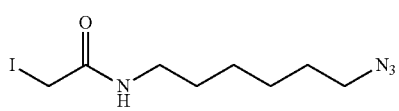

To a solution of 6-amino-hexanyl-1-azide trifluoroacetic acid salt (35 mg, 0.14 mmol) in DMF (0.1 mL) was added iodoacetic anhydride (0.10 g, 0.28 mmol) in the dark. After 2 hr, the reaction was stopped and the solution was partitioned between CHCl$_3$ (10 mL) and H$_2$O (10 mL). The organic layer was removed and the aqueous layer was reextracted with CHCl$_3$ (1×10 mL). The combined organics were rinsed with saturated NaCl (1×5 mL), dried over Na$_2$SO$_4$, decanted and concentrated. Purification via silica gel chromatography (2% MeOH/CHCl$_3$ containing 0.1% AcOH) provided the product (35 mg, 81%) as a yellow oil. TLC (10% MeOH/CHCl$_3$) R$_f$=0.75.

Example 38

Iodoacetamide Alkyne Synthesis

The synthesis of Iodoacetamide alkyne is shown in the following reaction scheme.

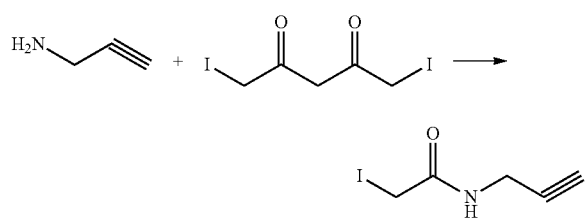

N-(iodoacetamide)-propargylamine

To a solution of propargylamine in DMF was added iodoacetic anhydride in the dark. After 2 hr, the reaction was stopped and the solution was partitioned between CHCl$_3$ and H$_2$O. The organic layer was removed and the aqueous layer was reextracted with CHCl$_3$. The combined organics were rinsed with saturated NaCl, dried over Na$_2$SO$_4$, decanted and concentrated.

Example 39

Maleimide Alkyne Synthesis

The synthesis of Maleimide alkyne is shown in the following reaction scheme.

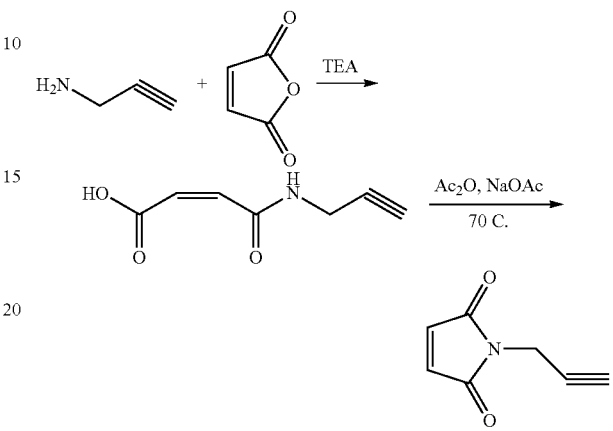

Propargylamine maleimide. After the reaction of propargylamine and maleic anhydride in the presence of TEA, the intermediate acid was cyclized in the presence of acetic anhydride and sodium acetate at 70° C., to afford the desired propargylamine maleimide.

Example 40

Maleimide Azide Synthesis

The synthesis of Maleimide azide is shown in the following reaction scheme.

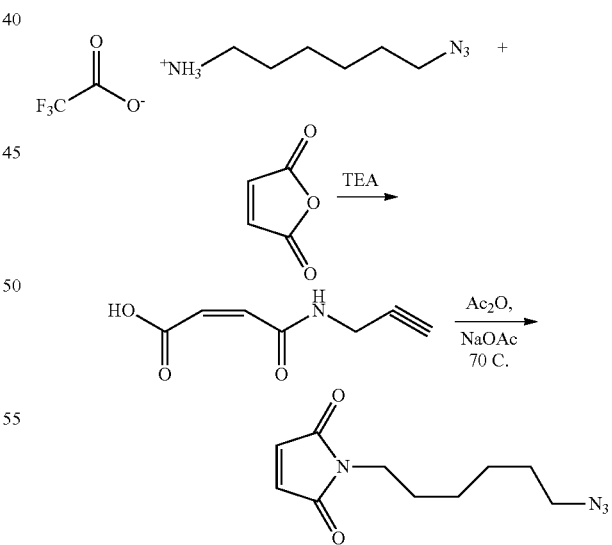

N-(6-Azido-aminohexyl)maleimide. After the reaction of 6-amino-hexanyl-1-azide trifluoroacetic acid salt and maleic anhydride in the presence of TEA, the intermediate acid was cyclized in the presence of acetic anhydride and sodium acetate at 70° C., to afford the desired N-(6-azido-aminohexyl)maleimide.

Example 41

Addition of Thioacetate-Azide and Amino-Azide Following Ba(OH)$_2$ Catalyzed β-Elimination of RII Phosphopeptide (NB B883-9-TN)

Figure 18A:
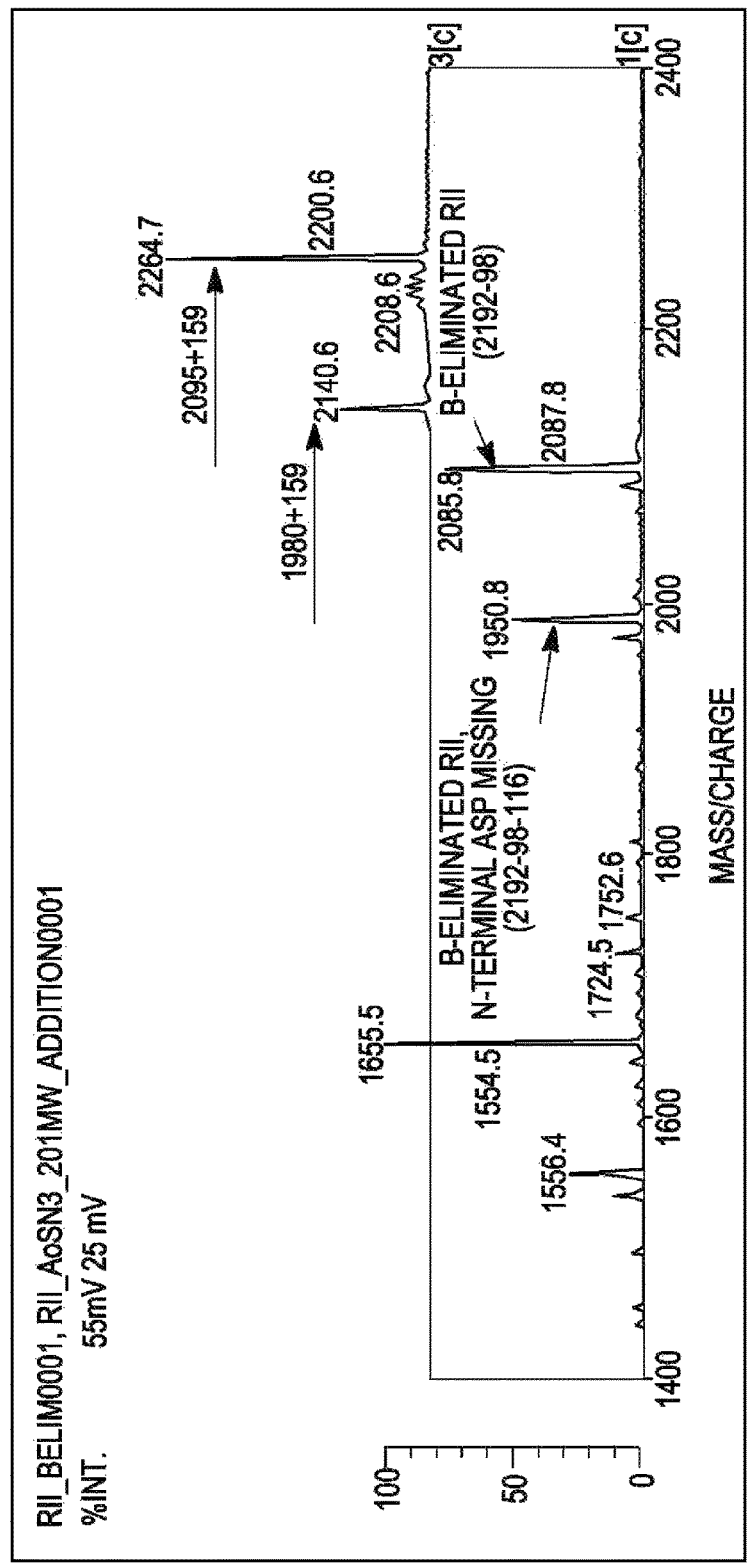
FIG. 18A: Shows β-elimination in the lower trace only of RII peptide and the upper trace shows simultaneous β-elimination and azido-thioacetate addition of RII peptide. β-elimination removes 98 Da from the peptide and azido-thioacetate addition adds 159 Da, therefore the expected mass of the addition product is 2253 Da (2192-98+159). The 1980 Da peak corresponds to β-eliminated RII with the N-terminal alanine cleaved. The 1655 Da peak corresponds to hydrolysis of RII at the phosphoserine residue and is not observed in the addition sample.
Figure 18B:
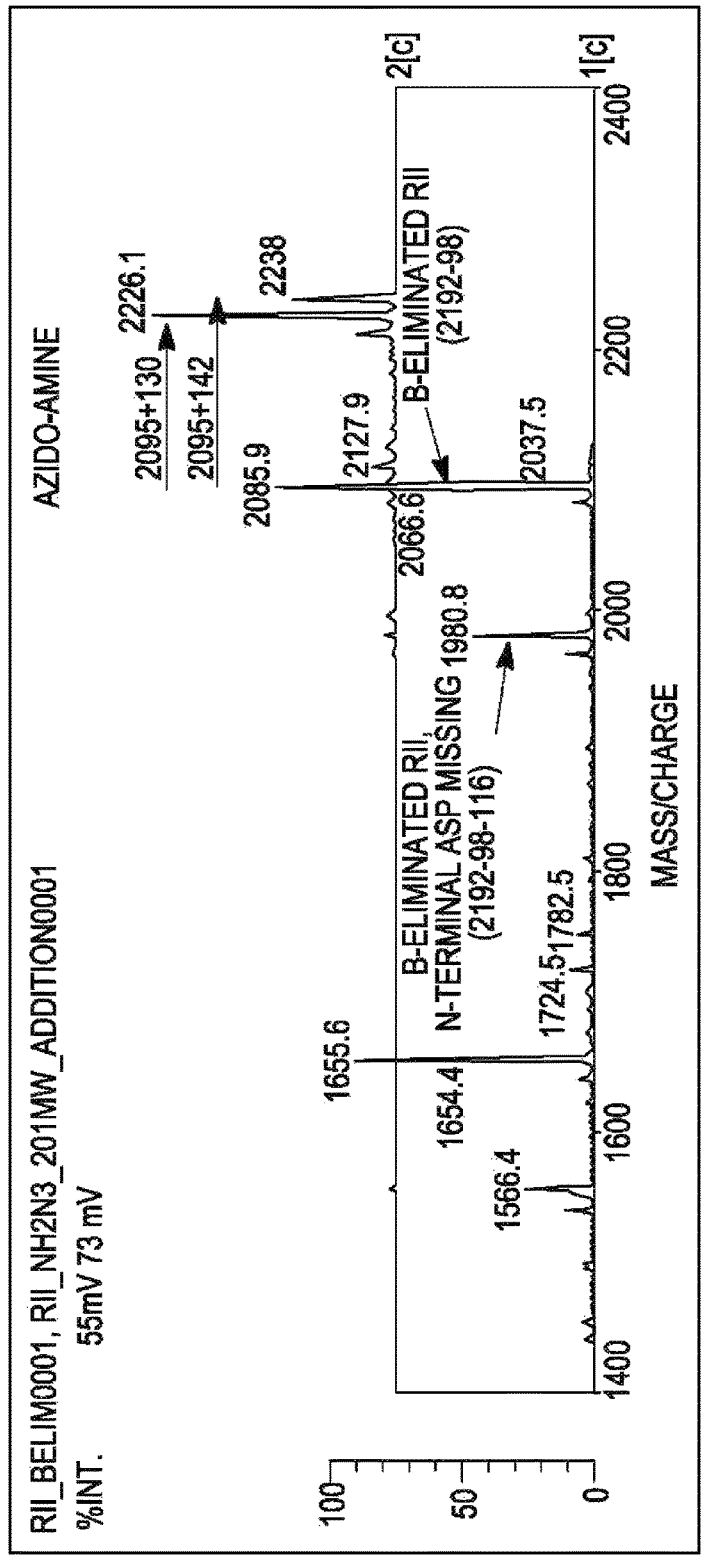
FIG. 18B: Shows β-elimination on the lower trace only of RII peptide and the upper trace shows simultaneous β-elimination and azido-amine addition of RII peptide. β-elimination removes 98 Da from the peptide and azido-amine addition adds 142 Da, therefore the expected mass of the addition product is 2236 Da (2192−98+142). Another addition product corresponding to +130 Da (expected mass=2224) is observed. PDS MALDI analysis shows the same fragment masses as for the 2236 product suggesting that the products are related. The 1980 Da peak corresponds to β-eliminated RII with the N-terminal alanine cleaved. The 1655 Da peak corresponds to hydrolysis of RII at the phosphoserine residue and is observed in lesser amount in the addition sample than in the β-elimination-only sample.
Figure 19A:
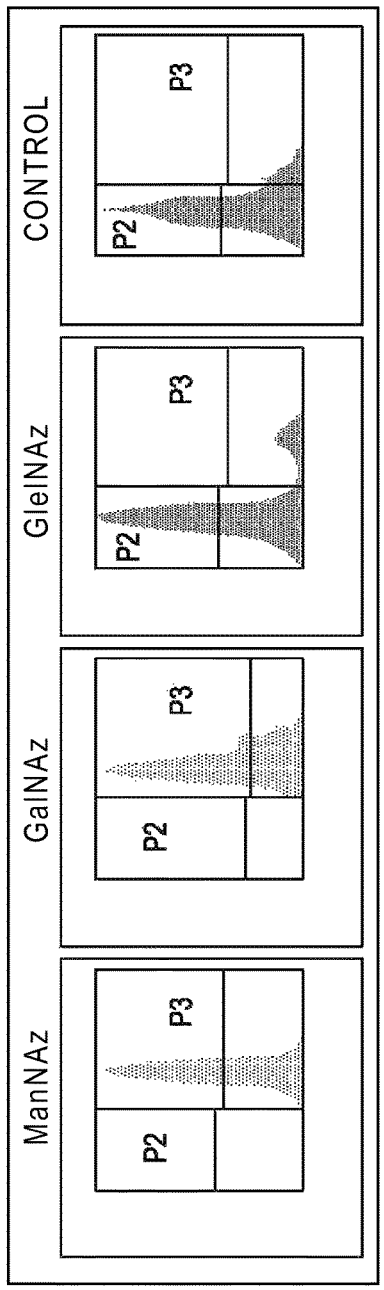
FIGS. 19A and 19B show the results of fluorescent Click labeling of live and fixed cells.
Figure 19B:
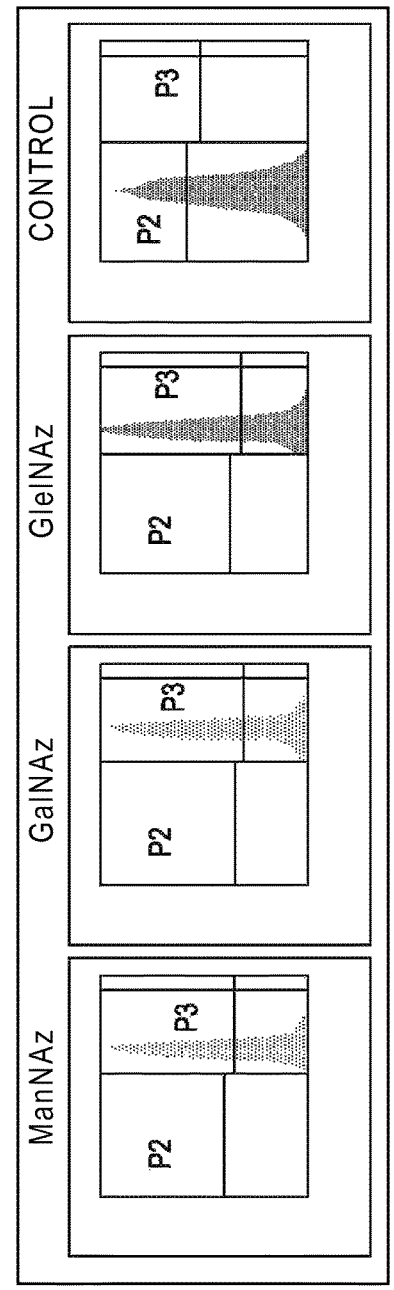
Figure 20:
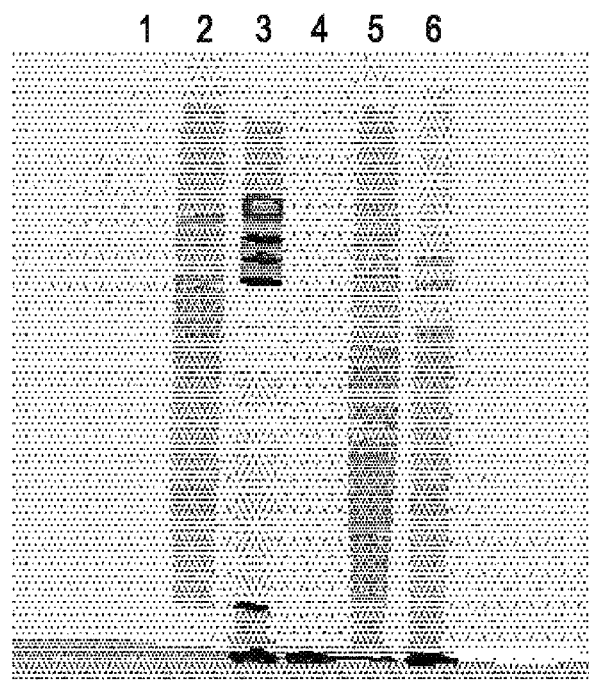
FIG. 20: Shows gel analysis of cell surface versus total glycoprotein subclasses. Lanes 1 and 4: Control unfed; Lane 2: GalNAz fed, surface labeled live cells, no perm; Lane 3: GalNAz fed, total cell lysates labeled; Lane 5: ManNAz fed, surface labeled live cells, no perm; Lane 6: ManNAz fed, total cell lysate labeled.

RII phosphopeptide (DLDVPIPGRFDRRVpSVAAE, 2192.08 Da) was azido-labeled by simultaneous β-elimination of the phosphate and addition of either thioacetate-azide or amino-azide to the resulting dehydroalanine residue. 2 nmol of peptide and 3 μmol of azide tag was incubated in 30 μL of 0.1M barium hydroxide for 2 hours at 35° C. After incubation, the barium was precipitated with 7 μL of 0.5M ammonium sulfate. After centrifugation, the supernatant was neutralized with 3 μL of glacial acetic acid, then desalted on a Vivapure RP microfilter. The peptide was eluted in 10 μL of 90% acetonitrile/0.1% TFA and analyzed by MALDI in positive reflectron mode (spot 0.5 μL of eluate and 0.5 μL of 6 mg/mL α-cyano-4-hydroxycinnamic acid). Under these conditions, all of the peptide is converted to addition product with thioacetate-azide as the addition reagent, whereas conversion is incomplete with amino-azide as the addition reagent. See FIGS. 18A and 18B.

TABLE 3

Thioacetate-azide

Amino-azide

Other catalysts that are not so basic but still effective in bringing about the elimination include tertiary amines and hindered secondary amines, such as but not limited to: phosphazene compounds, triethylamine, diisopropylethylamine, TEMED, triethanolamine 2,2,6,6-teramethylpiperidine, Proton Sponge DABCO, N-methylmorpholine 4-dimethylaminopyridine, 4-pyrrolidinylpyridine, an ion exchange resin such as Dowez 1 hydrixide, tetrabutylammonium hydroxide, benzyltriethylammonium hydroxide, or other phase transfer bases calcium hydroxide, barium hydroxide, or gallium hydroxide (which will also complex the phosphate group).

Example 42

Tagging Phosphoproteins Using Nucleotide Analogs

Phosphoproteins could be labeled in vivo or in vitro using alkyne or azide-tagged nucleotides whereby the azide or alkyne moiety is placed on the gamma phosphate. For example one of the nucleotides shown below is added to a reaction mixture containing a protein kinase and a kinase target molecule. After tagging the molecule is reacted with the appropriate alkyne or azide detection or affinity reagent for quantitation, visualization, or enrichment. In one example reaction, modified nucleotide substrates may be added directly to cultured cells for metabolic incorporation of the tagged gamma-phosphate molecule into cellular macromolecules including proteins. The process may involve treatment of the cells with pharmacological agents to detect alterations in phosphorylation dynamics. Entry of the compounds into live cultured cells could be enhanced by modifying the nucleotides with functional groups that would afford permeability, or by concomitant addition of cell permeablizing agents. In another example reaction, the kinase reaction could be performed in vitro using cellular extracts as the source of kinases and substrates. The modified nucleotides would be added to the reaction mixture and the reaction mixtures incubated with or without the addition of pharmacological agents of interest. The in vitro reaction may also entail adding an exogenous kinase or substrate source to the cellular extract along with the nucleotide analogs. In another application, the method could be used in vitro without cellular extracts, using purified kinases and kinase substrates. In all of the described examples the reaction mix may contain a buffer optimized for the particular kinases of interest, a kinase source, a metal ion source, glycerol, nucleotide ATP analog, and ATP. The "click" detection reaction with an alkyne probe would be performed in the presence of copper(I), or copper(II) in the presence of a copper(II) reducing agent, a copper(I) chelating agent, and an appropriate buffer to maintaining optimal pH conditions.

ATP-alkyne:

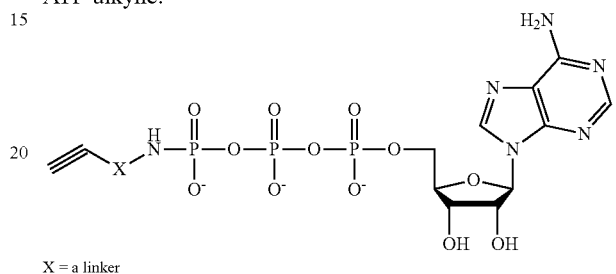

X = a linker

ATP-Azide:

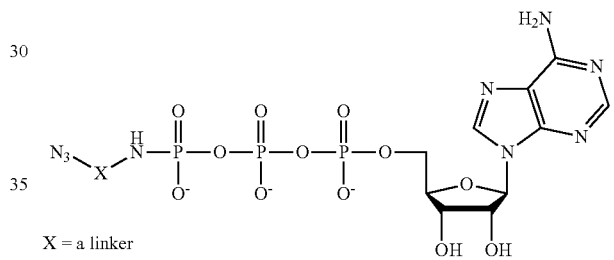

X = a linker

Example 43

Azido and Alkyne Reporter Molecules

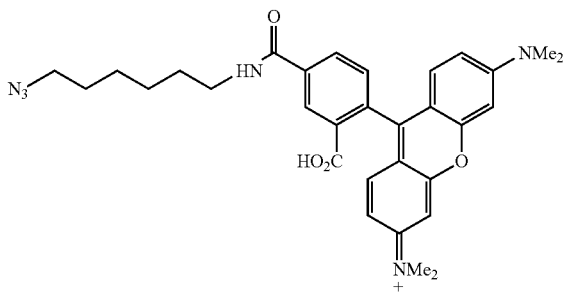

5-TAMRA-azide

5-TAMRA azide. To a solution of 6-(amino)-hexanyl-1-azide trifluoroacetic acid salt (see Scheme 1 for synthesis, 0.19 mmol) in DMF (0.5 mL) and DIEA (33 μL, 0.19 mmol) was added 5-carboxytetramethyl rhodamine, succinimidyl ester (5-TAMRA-SE, 50 mg, 0.094 mmol). After stirring the solution at RT for 10 min, the reaction solution was concentrated in vacuo. The crude was purified via silica gel chromatography (prep plate, 9:1 CH$_3$CN:H$_2$O) to afford the product as a pink solid (45.6 mg, 87%). TLC (CH$_3$CN:H$_2$O, 8:2) R$_f$=0.61, pink fluorescent spot; ESI-pos m/z 555 M$^+$, C$_{31}$H$_{35}$N$_6$O$_4$ (requires 555).

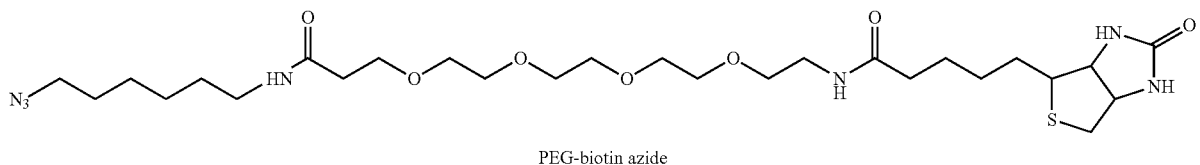 [SMILES: [N-]=[N+]=NCCCCCCNC(=O)CCOCCOCCOCCOCCNC(=O)CCCCC1SCC2NC(=O)NC21]

PEG-biotin azide

PEG-biotin azide. To a solution of 6-(amino)-hexanyl-1-azide trifluoroacetic acid salt (see Scheme 1 for synthesis, 0.17 mmol) in DMF (0.5 mL) and DIEA (60 µL, 0.34 mmol) was added NHS-PEO$_4$-biotin (Pierce, 50 mg, 0.08 mmol). After stirring the solution at RT overnight, the solution was concentrated in vacuo. The crude was purified via silica gel chromatography (7:1 CHCl$_3$: MeOH) to afford the product as a cloudy, white residue (12.3 mg, 12%). TLC (7:1, CHCl$_3$: MeOH, 8:2) R$_f$=0.54, faint UV active spot, stains pink with biotin dip; ESI-pos m/z 616 M$^+$, C$_{27}$H$_{49}$N$_7$O$_7$S (requires 616).

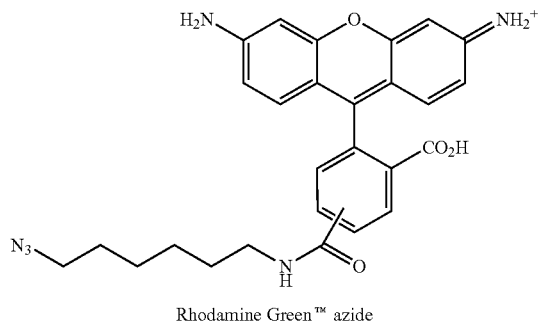

Rhodamine Green™ azide

Rhodamine Green™ azide (mix of 5- and 6-isomers). To a solution of 6-(amino)-hexanyl-1-azide trifluoroacetic acid salt (see Scheme 1 for synthesis, 0.20 mmol) in DMF (0.5 mL) and DIEA (50 µL, 0.28 mmol) was added Rhodamine Green™ carboxylic acid, succinimidyl ester, hydrochloride (mix of 5- and 6-isomers, 50 mg, 0.10 mmol). After stirring the solution at RT for 2 h the solution was concentrated in vacuo. HPLC (Phenomenex Prodigy ODS, internal diameter 21.2 mm, eluent 5-50% CH$_3$CN (over 60 min) in 25 mM TEAA, pH=4.7, flow rate of 20 mL/min) gave 21.1 mg of product (43%) t$_R$=43-47 min; TLC (CH$_3$CN:H$_2$O:AcOH, 8:1:1) R$_f$=0.74, fluorescent yellow spot; ESI-pos m/z 499 (M+H, C$_{27}$H$_{27}$N$_6$O$_4$ requires 499).

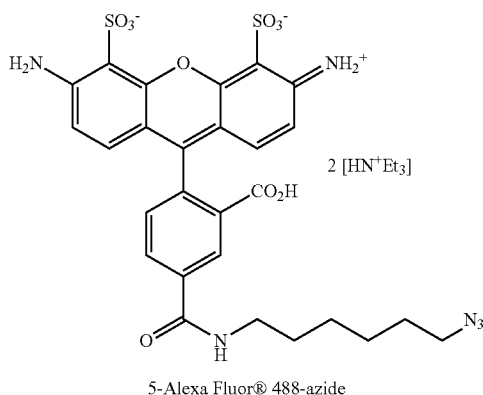

5-Alexa Fluor® 488-azide

Alexa Fluor® 488 azide (5 Isomer). To a solution of 6-(amino)-hexanyl-1-azide trifluoroacetic acid salt (see Scheme 1 for synthesis, 0.44 mmol) in DMF (0.5 mL) and DIEA (0.11 mL, 0.88 mmol) was added Alexa Fluor® 488 5-carboxylic acid, 2,3,5,6-tetrafluorophenyl ester, bis(triethylammonium salt) (200 mg, 0.22 mmol). After stirring the solution at RT for 1 h, the solution was concentrated in vacuo. HPLC (Phenomenex Prodigy ODS, internal diameter 21.2 mm, eluent 0-60% CH$_3$CN (over 30 min) in 25 mM TEAA, pH=4.7, flow rate of 20 mL/min) gave 58.1 mg of product (30%) t$_R$=23-27 min; TLC (CH$_3$CN:H$_2$O, 8:2) R$_f$=0.58, fluorescent yellow spot; ESI-neg m/z 657 (M$^-$, C$_{27}$H$_{25}$N$_6$O$_{10}$S$_2^-$ requires 657).

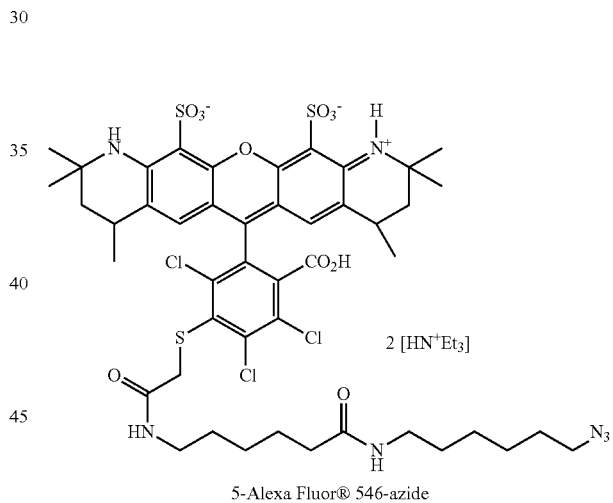

5-Alexa Fluor® 546-azide

Alexa Fuor® 546 azide. To a solution of 6-(amino)-hexanyl-1-azide trifluoroacetic acid salt (see Scheme 1 for synthesis, 0.093 mmol) in DMF (0.5 mL) and DIEA (32 µL, 0.19 mmol) was added Alexa Fluor® 546 carboxylic acid, succinimidyl ester, (50 mg, 0.05 mmol). After stirring the solution at RT for 2 h, the solution was concentrated in vacuo.

HPLC (Phenomenex Prodigy ODS, internal diameter 21.2 mm, eluent 10-60% CH$_3$CN (over 60 min) in 25 mM TEAA, pH=4.7, flow rate of 20 mL/min) gave 27.2 mg of product (54%) t$_R$=48-52 min; TLC (CH$_3$CN:H$_2$O, 9:1) R$_f$=0.24, fluorescent pink spot; ESI-neg m/z 1084 (M$^-$, C$_{46}$H$_{55}$Cl$_3$N$_7$O$_{11}$S$_3^-$ requires 1084).

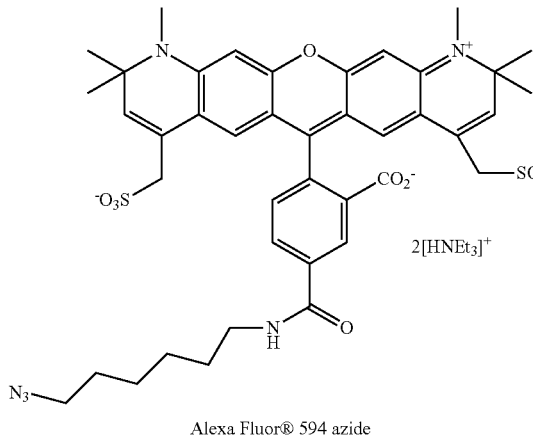

Alexa Fluor® 594 azide

Alexa Fluor® 594 azide (5 isomer). To a solution of 6-(amino)-hexanyl-1-azide trifluoroacetic acid salt (see Scheme 1 for synthesis, 0.12 mmol) in DMF (0.5 mL) and DIEA (42 μL, 0.24 mmol) was added Alexa Fluor® 594 carboxylic acid, succinimidyl ester *5-isomer* (50 mg, 0.06 mmol). After stirring the solution at RT for 2 h, the solution was concentrated in vacuo. HPLC (Phenomenex Prodigy ODS, internal diameter 21.2 mm, eluent 25-60% $CH_3CN$ (over 30 min) in 25 mM TEAA, pH=4.7, flow rate of 20 mL/min) gave 16.5 mg of product (32%) $t_R$=23-25 min; TLC ($CH_3CN:H_2O$, 9:1) $R_f$=0.36, fluorescent red spot; ESI-neg m/z 845 ($M^-$, $C_{41}H_{45}N_6O_{10}S_2^-$ requires 845).

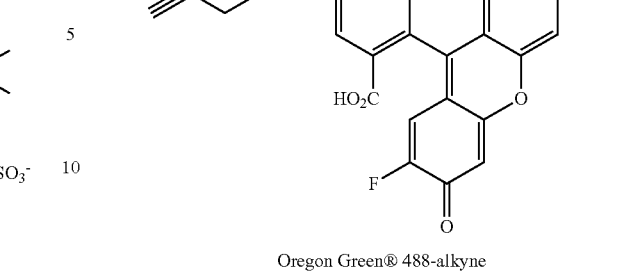

Oregon Green® 488-alkyne

Oregon Green® 488-alkyne. To a solution of Oregon Green® 488 carboxylic acid, succinimidyl ester (50 mg, 0.98 mmol) in DMF (0.5 mL) was added propargylamine (0.26 μL, 0.40 mmol) and $H_2O$ (0.1 mL). After stirring at RT for 15 min, the solution was concentrated. HPLC (Phenomenex Prodigy ODS, internal diameter 21.2 mm, eluent 15-30% CH3Cn in 25 mM TEAA pH 4.7, flow rate of 15 mL/min) gave 44.5 mg of product (99%) $t_R$=5-13 min; TLC ($CH_3CN:H_2O$, 8:2) $R_f$=0.60, fluorescent yellow spot; ESI-neg m/z 448 ($M-H^+$, $C_{24}H_{12}F_2NO_6^-$ requires 448).

Alkyne Biotin Compounds

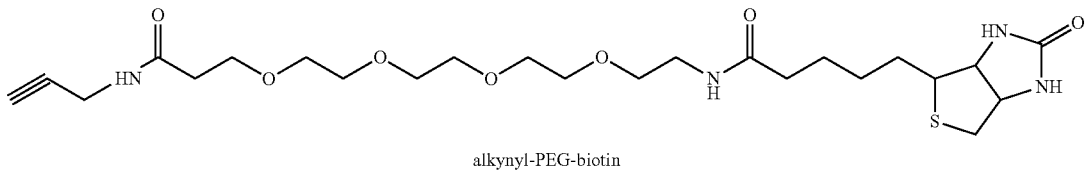

alkynyl-PEG-biotin

Alkynyl-PEG-biotin. To a solution of NHS-PEO$_4$-biotin (Pierce, 25 mg, 0.004 mmol) in DMF (0.1 mL) at RT was added propargylamine (0.3 mL, 4.5 mmol). After stirring for 3 h, the solution was concentrated in vacuo and re-evaporated twice from toluene. HPLC (Phenomenex Prodigy ODS, internal diameter 21.2 mm, eluent 35-50% MeOH in 25 mM $NH_4Ac$, pH 6.5, flow rate of 15 mL/min) gave 14.4 mg, (64%, a white solid) $t_R$=26-30 min; TLC ($CHCl_3$:MeOH, 7:1) $R_f$=0.20, UV active spot; ESI m/z 529 ($M+H^+$, $C_{24}H_{40}N_4O_7S$ requires 529).

Alkyne Dyes:

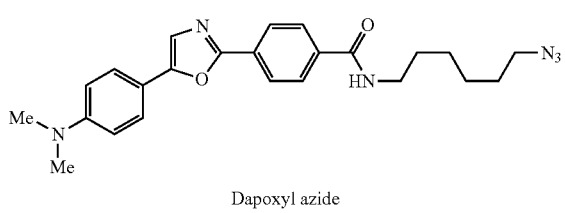 [SMILES: CN(C)c1ccc(-c2cnc(-c3ccc(C(=O)NCCCCCCN=[N+]=[N-])cc3)o2)cc1]

Dapoxyl azide

Dapoxyl azide. To a solution of 6-(amino)-hexanyl-1-azide trifluoroacetic acid salt (see Scheme 1 for synthesis, 0.25 mmol) in DMF (0.5 mL) and DIEA (43 μL, 0.25 mmol) was added Dapoxyl® carboxylic acid, succinimidyl ester (50 mg, 0.12 mmol). After stirring the solution at RT for 1 h, the solution was concentrated in vacuo. Purified by SPE (Supelco C18 DSC) to give 41.6 mg of product (78%); ESI-pos m/z 433 ($M^+$, $C_{24}H_{28}N_6O_2$ requires 433).

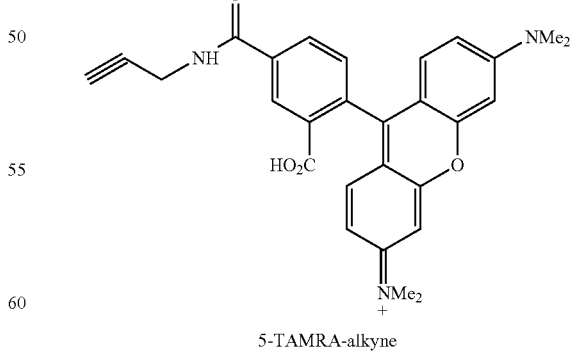

5-TAMRA-alkyne

5-TAMRA-alkyne. To a solution of 5-carboxytetramethyl rhodamine, succinimidyl ester (5-TAMRA-SE, 0.10 g, 0.19 mmol) in DMF (0.5 mL) was added propargylamine (25 μL, 0.38 mmol) and $H_2O$ (0.5 mL). After stirring the solution for 30 min at RT, the solution was concentrated in vacuo. HPLC (Phenomenex Prodigy ODS, internal diameter 21.2 mm, eluent 25-40% CH$_3$CN in 25 mM TEAA, pH 4.7, flow rate of 15 mL/min) gave 68 mg of product (82%, a purple solid) $t_R$=23-33 min; TLC (CH$_3$CN:H$_2$O, 8:2) R$_f$=0.67, fluorescent orange spot; ESI m/z 469 (M+H$^+$, C$_{28}$H$_{26}$N$_3$O$_4$ requires 469).

eluent 25-40% CH$_3$CN in 25 mM NH$_4$Ac, pH 4.7, flow rate of 15 mL/min) gave 30 mg of product (65%, a red solid) $t_R$=23-30 min; TLC (CH$_3$CN:H$_2$O, 1:1) R$_f$=0.58, fluorescent red spot; ESI m/z 664 (M$^+$, C$_{33}$H$_{34}$N$_3$O$_8$S$_2$ requires 664).

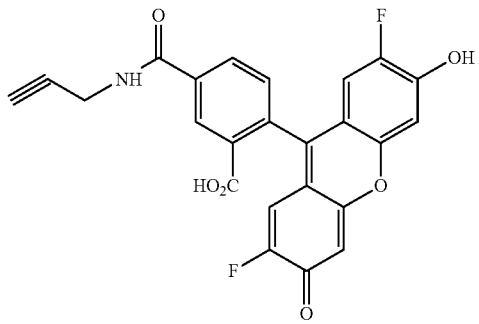

Oregon Green® 488-alkyne

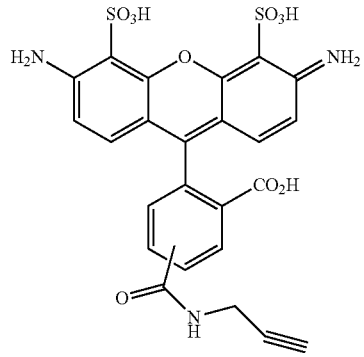

Alexa Fluor® 488-alkyne

Oregon Green® 488-alkyne. To a solution of Oregon Green® 488 carboxylic acid, succinimidyl ester (50 mg, 0.98 mmol) in DMF (0.5 mL) was added propargylamine (0.26 µL, 0.40 mmol) and H$_2$O (0.1 mL). After stirring at RT for 15 min, the solution was concentrated. HPLC (Phenomenex Prodigy ODS, internal diameter 21.2 mm, eluent 15-30% CH3Cn in 25 mM TEAA pH 4.7, flow rate of 15 mL/min) gave 44.5 mg of product (99%) $t_R$=5-13 min; TLC (CH$_3$CN:H$_2$O, 8:2) R$_f$=0.60, fluorescent yellow spot; ESI-neg m/z 448 (M–H$^+$, C$_{24}$H$_{12}$F$_2$NO$_6^-$ requires 448).

Alexa Fluor® 488-alkyne. To a solution of Alexa Fluor® 488 carboxylic acid, succinimidyl ester, dilithium salt, mixed isomers, (51 mg, 0.08 mmol) in DMF (2.0 mL) was added propargylamine (54 µL, 0.80 mmol). The solution was stirred at RT for 4 h then concentrated in vacuo. The crude product was purified using column chromatography on silica gel (CH$_3$CN:H$_2$O, 8:2) to afford 20 mg (44%, an orange solid). TLC (CH$_3$CN:H$_2$O, 3:1) R$_f$=0.68; ESI-neg m/z 570 (M–2, C$_{24}$H$_{16}$N$_3$O$_{10}$S$_2^{2-}$ requires 570).

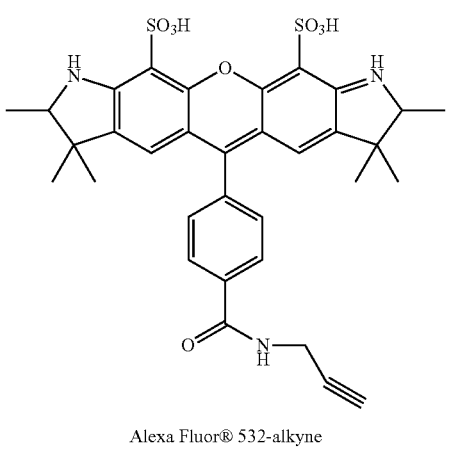

Alexa Fluor® 532-alkyne

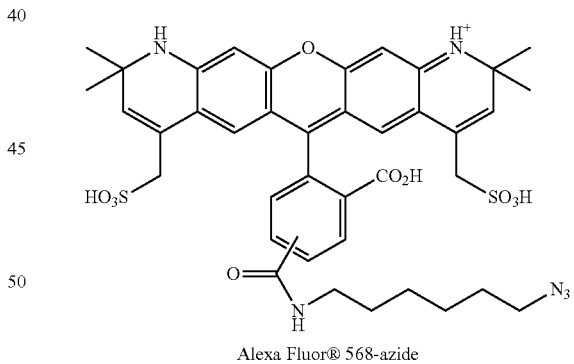

Alexa Fluor® 568-azide

Alexa Fluor® 532-alkyne. To a solution of Alexa Fluor® 532 carboxylic acid, succinimidyl ester (51 mg, 0.07 mmol) in DMF (4.0 mL) was added propargylamine (0.1 mL) and H$_2$O (1.0 mL). The solution was stirred at RT for 1 h then concentrated in vacuo to afford the crude product. HPLC (Phenomenex Prodigy ODS, internal diameter 21.2 mm, Alexa Fluor® 568-azide.
To a solution of 6-(amino)-hexanyl-1-azide (see Scheme 1 for synthesis, 0.04 mmol) in DMF (0.2 mL) and DIEA (7 µL, 0.04 mmol) was added Alexa Fluor® 568 carboxylic acid, succinimidyl ester (mix of isomers, 25 mg, 0.02 mmol). After stirring the solution at RT for 2.5 h, H$_2$O (0.2 mL) was added and the solution was concentrated in vacuo. HPLC (Phenomenex Prodigy ODS, internal diameter 21.2 mm, eluent 20-35% CH$_3$CN in 25 mM NH$_4$Ac, pH 4.7, flow rate of 15 mL/min) gave 15.3 mg of product (99%) $t_R$=24-30 min; TLC (CH$_3$CN:H$_2$O, 8:2) R$_f$=0.63, fluorescent pink spot; ESI-neg m/z 817 (M–2, C$_{39}$H$_{41}$N$_6$O$_{10}$S$_2^-$ requires 817).

Example 44

Triarylphosphine Dye

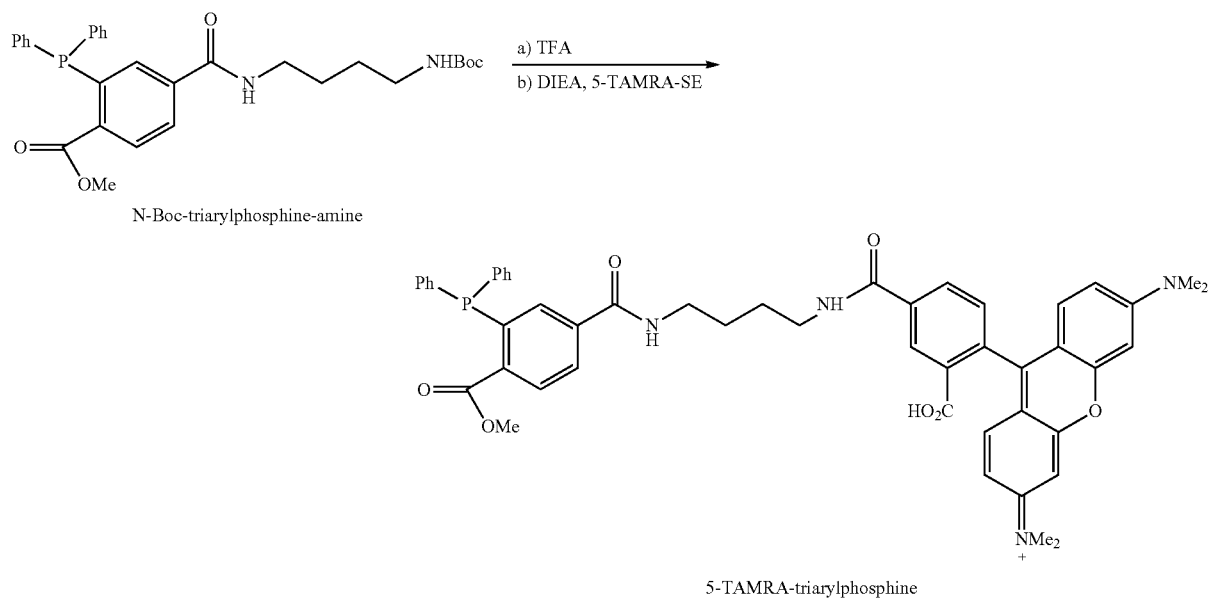

5-TAMRA-triarylphosphine. To a solution of N-Boc-triarylphosphine-amine (see Scheme 2 for synthesis, 10 mg, 0.018 mmol) in $CH_2Cl_2$ (1.0 mL) was added TFA (0.5 mL). The reaction solution was stirred at RT for 30 min, concentrated in vacuo, and re-evaporated twice from toluene. The crude amine (0.018 mmol, 99%) was used directly in the next reaction without further purification.

To a solution of triarylphosphine-amine (0.018 mmol) in DMF (0.2 mL) and DIEA (12 µL, 0.089 mmol) was added 5-carboxytetramethyl rhodamine, succinimidyl ester (5-TAMRA-SE, 9 mg, 0.022 mmol). After stirring the solution at RT for 2.5 h, the solution was concentrated in vacuo. HPLC (Phenomenex Luna C18(2), internal diameter 10 mm, eluent 40-55% $CH_3CN$ in 25 mM $NH_4Ac$, pH=7, flow rate of 5.0 mL/min) gave 4.1 mg of product (27%) $t_R$=32-34 min; TLC (MeOH:$CHCl_3$, 1:9) $R_f$=0.67, fluorescent pink spot; ESI m/z 848 (M+H$^+$, $C_{50}H_{48}N_4O_7P$ requires 848).

The reagents employed in the examples are commercially available or can be prepared using commercially available instrumentation, methods, or reagents known in the art. All references cited herein are incorporated by reference in their entireties. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

U.S. patent applications with attorney docket numbers IVGN 745.1 and IVGN 745.2, both filed on Feb. 12, 2007, claiming priority to U.S. Provisional Application Nos. 60/772,221 and 60/804,640 are hereby incorporated by reference.

We claim:
1. A method of detecting an azido modified protein or peptide, comprising:
   a) forming an azide-alkyne cycloaddition reaction mixture by adding the followings in a reaction mixture:
      a reporter molecule that comprises a terminal alkyne moiety:
      the azido modified protein or peptide;
      copper (II) ions;
      at least one reducing agent; and
      a copper chelator selected from the group consisting of N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), trientine, glutathione, histadine, polyhistadine or tetra-ehylenepolyamine (TEPA), 1,10 phenanthroline, bathophenanthroline disulfonic acid (4,7-diphenyl-1,10-phenanthroline disulfonic acid) and bathocuproine disulfonic acid (2,9-dimethyl-4,7-diphenyl-1,10-phenanthroline disulfonate), wherein the copper chelator is added to the reaction mixture after the copper (II) ions have been contacted with the at least one reducing agent, and wherein the at least on reducing agent is selected from the group consisting of acorbate, Tris(2-Carboxyethyl) Phosphine (TCEP), TCP (2,4,6-trichlorophenol), NADH, NADPH, thiosulfate, 2-mercaptoethanol, dithiothreotol, glutathione, cysteine, metallic copper, quinone, hydroquinone, vitamin $K_1$, $Fe^{2+}$, and $Co^{2+}$;
   b) incubating the azide-alkyne cycloaddition reaction mixture for a sufficient amount of time to form a protein or peptide-reporter molecule conjugate;

c) separating the protein or peptide-reporter molecule conjugate by size and/or weight of the protein or peptide-reporter molecule conjugate to form a separated protein or peptide-reporter molecule conjugate;

d) illuminating the separated protein or peptide-reporter molecule conjugate with an appropriate wavelength to form an illuminated protein or peptide-reporter molecule conjugate;

e) observing the illuminated protein or peptide-reporter molecule conjugate wherein the azido modified protein or peptide is detected.

2. The method according to claim 1, wherein the protein is a glycoprotein.

3. The method according to claim 1, wherein the copper chelator is N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, trientine, glutathione, histadine, polyhistadine or tetra-ethylenepolyamine (TEPA).

4. The method according to claim 1, wherein the copper chelator is 1,10 phenanthroline, bathophenanthroline disulfonic acid (4,7diphenyl-1,10-phenanthroline disulfonic acid) or bathocuproine disulfonic acid (2,9-dimethyl-4,7-diphenyl-1,10-phenanthroline disulfonate).

5. The method according to claim 1, wherein the reducing agent is ascorbate.

6. The method according to claim 1, wherein the separating step comprises chromatography or electrophoresis.

7. The method according to claim 1, wherein the reporter molecule is a xanthene, a cyanine, a coumarin, a borapolyazaindacene, an oxazine, or a pyrene dye.

8. The method according to claim 1, wherein the reporter molecule is an enzyme substrate, a fluorescent protein, a particle, or a hapten.

* * * * *

UNITED STATES PATENT AND TRADEMARK OFFICE
CERTIFICATE OF CORRECTION

PATENT NO.         : 9,645,140 B2
APPLICATION NO.    : 14/330727
DATED              : May 9, 2017
INVENTOR(S)        : Brian Agnew et al.

It is certified that error appears in the above-identified patent and that said Letters Patent is hereby corrected as shown below:

In the Claims

In Claim 1, Line 49 "tetra-ehylenepolyamine" should be corrected to "tetra-ethylenepolyamine".

In Claim 1, Line 59 "acorbate" should be corrected to "ascorbate".

Signed and Sealed this
Third Day of April, 2018

Andrei Iancu
*Director of the United States Patent and Trademark Office*